(12) United States Patent
Xia et al.

(10) Patent No.: US 9,371,292 B2
(45) Date of Patent: Jun. 21, 2016

(54) QUINAZOLINE DERIVATIVE, PREPARATION METHOD THEREFOR, INTERMEDIATE, COMPOSITION AND APPLICATION THEREOF

(75) Inventors: Guangxin Xia, Shanghai (CN); Jingkang Shen, Shanghai (CN); Yongping Yu, Hangzhou (CN); Wenteng Chen, Hangzhou (CN); Chunchun Zhang, Shanghai (CN); Yu Hao, Shanghai (CN); Jing Zhang, Shanghai (CN); Bojun Li, Shanghai (CN); Xuejun Liu, Shanghai (CN)

(73) Assignees: SHANGHAI PHARMACEUTICALS HOLDINGS CO., LTD., Shanghai (CN); ZHEJIANG UNIVERSITY, Zhejiang (CN)

( * ) Notice: Subject to any disclaimer, the term of this patent is extended or adjusted under 35 U.S.C. 154(b) by 12 days.

(21) Appl. No.: 14/234,514

(22) PCT Filed: Jul. 27, 2012

(86) PCT No.: PCT/CN2012/079238
§ 371 (c)(1),
(2), (4) Date: Mar. 26, 2014

(87) PCT Pub. No.: WO2013/013640
PCT Pub. Date: Jan. 31, 2013

(65) Prior Publication Data
US 2014/0206687 A1    Jul. 24, 2014

(30) Foreign Application Priority Data
Jul. 27, 2011 (CN) .......................... 2011 1 0213997

(51) Int. Cl.
*C07D 239/94* (2006.01)
*A61K 31/517* (2006.01)
*A61P 35/00* (2006.01)
*C07D 401/12* (2006.01)
*C07D 403/12* (2006.01)
*C07D 405/12* (2006.01)
*C07D 413/12* (2006.01)

(52) U.S. Cl.
CPC ............ *C07D 239/94* (2013.01); *C07D 401/12* (2013.01); *C07D 403/12* (2013.01); *C07D 405/12* (2013.01); *C07D 413/12* (2013.01)

(58) Field of Classification Search
USPC ........ 514/234.5, 252.17, 266.4; 544/116, 293
See application file for complete search history.

(56) References Cited

U.S. PATENT DOCUMENTS

| 6,127,374 A * | 10/2000 | Bridges .................... 514/217.06 |
| 2002/0173509 A1 | 11/2002 | Himmelsbach et al. | |
| 2004/0158065 A1 | 8/2004 | Barth et al. | |
| 2008/0056990 A1 | 3/2008 | Mishani et al. | |
| 2008/0300248 A1 | 12/2008 | Guo et al. | |
| 2008/0318950 A1 | 12/2008 | Ahn et al. | |
| 2014/0128417 A1 * | 5/2014 | Shen ..................... C07D 405/06 514/266.24 |
| 2016/0039838 A1 * | 2/2016 | Zhang .................. A61K 31/196 424/85.7 |

FOREIGN PATENT DOCUMENTS

| CA | 2774099 A1 | 3/2011 |
| CN | 1745073 A | 3/2006 |
| CN | 102146084 A * | 8/2011 |
| CN | 102382065 A * | 3/2012 |
| CN | 102898386 A | 1/2013 |
| CN | 103965120 A * | 8/2014 |
| JP | 2006-517959 A | 8/2006 |
| JP | 2009-514947 A | 4/2009 |
| WO | WO 99/06396 A1 | 2/1999 |
| WO | WO 2004/069791 A2 | 8/2004 |
| WO | WO 2006/071017 A1 | 7/2006 |
| WO | WO 2007/085638 A1 | 8/2007 |
| WO | WO 2008/033747 A2 | 3/2008 |
| WO | WO 2011/029265 A1 | 3/2011 |
| WO | WO 2011/126903 A2 | 10/2011 |

OTHER PUBLICATIONS

Patani et al. "Bioisosterism: A Rational Approach in Drug Design" Chem. Rev. 1996, 96, 3147-3176.*
Tsou et al. "6-Substituted-4-(3-bromophenylamino) quinazolines as Putative Irreversible Inhibitors of the Epidermal Growth Factor Receptor (EGFR) and Human Epidermal Growth Factor Receptor (HER-2) Tyrosine Kinases with Enhanced Antitumor Activity" J. Med. Chem. 2001, 44, 2719-2734.*
Nov. 15, 2012 International Search Report issued in International Patent Application No. PCT/CN2012/079238 (with translation).
Nov. 15, 2012 Written Opinion of the International Searching Authority issued in International Patent Application No. PCT/CN2012/079238 (with translation).
(Continued)

*Primary Examiner* — Nyeemah A Grazier
*Assistant Examiner* — Amanda L Aguirre
(74) *Attorney, Agent, or Firm* — Oliff PLC

(57) ABSTRACT

Disclosed are as represented by Formula (I) a quinazoline derivative and a pharmaceutical acceptable salt thereof, or, an enantiomer, a non-enantiomer, a tautomer, a racemate, a solvate, a metabolic precursor, or a prodrug of both. Also disclosed are a preparation method therefor, an intermediate, a pharmaceutical composition having the quinazoline derivative, and an application thereof. The quinazoline derivative of the present invention is provided with improved anti-tumor activity.

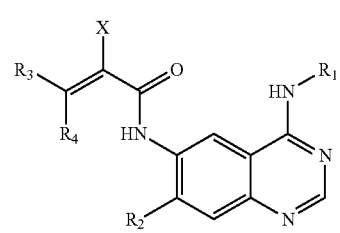

4 Claims, No Drawings

(56) References Cited

OTHER PUBLICATIONS

Apr. 17, 2014 Chinese Office Action issued in Chinese Patent Application No. CN201210279708.6 (with translation).

Ray et al., "The Role of EGFR Inhibition in the Treatment of Non-Small Cell Lung Cancer" *The Oncologist*, 2009, vol. 14, pp. 1116-1130.

Cha, et al., "Discovery of a Novel Her-1/Her-2 Dual Tyrosine Kinase Inhibitor for the Treatment of Her-1 Selective Inhibitor-Resistant Non-small Cell Lung Cancer" *Journal of Medicinal Chemistry*, 2009, vol. 52, pp. 6880-6888.

Wissner, et al., "Dual Irreversible Kinase Inhibitors: Quinazoline-based Inhibitors Incorporating Two Independent Reactive Centers with Each Targeting Different Cysteine Residues in the Kinase Domains of EGFR and Veger-2" *Bioorganic & Medicinal Chemistry*, 2007, vol. 15, pp. 3635-3648.

Kaila, et al. "Identification of a Novel Class of Selective Tpl2 Kinase Inhibitors: 4-Alkylamino-[1,7]naphthyridine-3-carbonitriles," *Bioorganic & Medicinal Chemistry*, 2007, vol. 15, pp. 6425-6442.

Diederich et al., "Diastereoselective Zwitterionic Aza-Claisen Rearrangement: Synthesis of Nine-Membered Ring Lactams and Transannular Ring Contraction," *Chemistry—A European Journal*, 1996, vol. 2, pp. 894-900.

Bridges, et al. "Tyrosine Kinase Inhibitors. 8. An Unusually Steep Structure-Activity Relationship for Analogues of 4-(3-Bromoanilino)-6,7-dimethoxyquinazoline (PD 153035), a Potent Inhibitor of the Epidermal Growth Factor Receptor" *Journal of Medicinal Chemistry*, 1996, vol. 39, pp. 267-276.

Ma et al., "The Challenge of Selecting Protein Kinase Assays for Lead Discovery Optimization," *Expert Opin Drug Discov.*, 2008, vol. 3, No. 6, pp. 1-22.

Chinese Patent Application No. 201110213997.5 (with translation), Jul. 27, 2011.

Nov. 27, 2014 Office Action issued in Chinese Application No. 201210279708.6.

Feb. 9, 2016 Office Action issued in Japanese Patent Application No. 2014-521929.

* cited by examiner

QUINAZOLINE DERIVATIVE, PREPARATION METHOD THEREFOR, INTERMEDIATE, COMPOSITION AND APPLICATION THEREOF

FIELD OF INVENTION

Specifically the present invention relates to a quinazoline derivative, preparation method therefor, intermediate, composition and application thereof.

PRIOR ARTS

Protein kinases plays an important role in cell signaling. It can trigger a series of biochemical reactions through transferring phosphate groups from ATP to specific amino acid residues of functional protein. According to the type of the amino acid which acts as a substrate in the process of phosphorylation, protein kinases can be categorized as serine-threonine kinases (STKs) and tyrosine kinases (PTKs). PTKs can be divided into three types: ① receptor protein tyrosine kinases (RPTKs), single transmembrance protein, more than 50 kinds of which have been found in vertebrates; ② cytoplasmic tyrosine kinases, such as Src family, Tec family, JAK family and so on; ③ intranuclear tyrosine kinases, for example Abl and Wee.

The extracellular domain of the RPTKs is ligand binding domain, the ligand is a soluble or membrane bound polypeptide or protein hormone, including many kinds of cell growth factors (such as EGF). The intracellular domain is catalytic site of tyrosine protein kinases, having autophosphorylation site. In extracellular domain, a ligand binds to a receptor and arouses change of conformation, which leads to dimerization of the receptor and fomation of homodimer or heterodimer. The residues of the intracellular domain of tyrosine in the dimer are phosphorylated with each other, and activate the activity of tyrosine protein kinase in the receptor. Most receptor as cell growth factor contains peptide sequences mainly including EGFR, PDGFR, FGFR, VEGFR etc. of tyrosine kinase. It can be seen that in many tumors, different receptors of tyrosine kinase are over-expressed or excessive activated. According to similarity of peptide sequences and other characteristics of structure, these receptors are divided into several families: ① epidermal growth factor (EGFR) family; ② insulin receptor family; ③ platelet-derived growth factor receptor (PDGFR) family; ④ fibroblast growth factor receptor (FGFR) family; ⑤ vascular endothelial growth factor receptor (VEGFR) family; ⑥ Fibronectin III receptors; ⑦ hepatocyte growth factor receptor (HGFR), etc. Overexpression of these receptors respectively in different kinds of tumors induce the abnormal activation of intracellular signal, which results in transformation and continuous proliferation of cells, promotes tumorigenesis and development. Therefore, it can play an anti-tumor effect when the inhibitor of above-mentioned protein kinase, in particular the tyrosine kinase, is used. For example EGFR family, including EGFR, HER2, HER3, HER4 etc., is one kind of tyrosine kinase that has been studied a lot, and highly expresses in a variety of tumors, which is related to the proliferation, metastasis and other phenomena of cancer cells. To look for an inhibitor targeting EGFR has become one of the most important direction for research of anti-cancer drugs in recent years.

EGFR tyrosine kinase inhibitors can be divided into reversible inhibitors and irreversible inhibitors. Gefitinib and Erlotinib which have been already for sale are reversible inhibitors, and with their use in the clinical, reversible inhibitors gradually shows the problem of resistance. Irreversible inhibitors can be bonded to EGFR tyrosine kinase by covalent bonding. Many pre-clinical studies show that the irreversible inhibitors which are in the development recently can be against the T790M mutation and overcome drug resistance caused by T790M; meanwhile, irreversible inhibitors that are in the clinical development stage (for example BMW 2992 and PF00299804 and so on) can inhibit several members of the EGFR receptor family, especially EGFR and HER-2. This may be caused by blocking collaborative signaling pathway activated by homodimer and heterodimer, which results in the improvement of inhibitory effect (Oncologist, 2009, 14(11): 1116-1130).

CONTENT OF THE PRESENT INVENTION

The technical problem to be solved in the present invention is to provide a quinazoline derivative and a pharmaceutical acceptable salt thereof, or, an enantiomer, a non-enantiomer, a tautomer, a racemate, a solvate, a metabolic precursor, or a prodrug of both, a preparation method therefor, an intermediate, a pharmaceutical composition having the quinazoline derivative, and use thereof that are completely different from prior arts. The quinazoline derivative of the present invention is provided with improved anti-tumor activity.

Thus, the present invention relates to a quinazoline derivative represented by formula (I) and a pharmaceutical acceptable salt thereof, or, an enantiomer, a non-enantiomer, a tautomer, a racemate, a solvate, a metabolic precursor, or a prodrug of both;

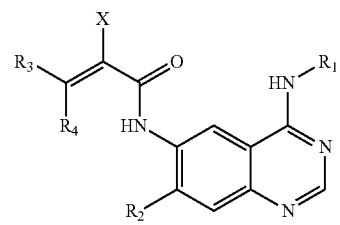

I wherein, $R_1$ is a substituted or unsubstituted $C_6$~$C_{10}$ aryl (preferably phenyl) or a substituted or unsubstituted $C_3$~$C_{12}$ heteroaryl (the $C_3$~$C_{12}$ heteroaryl can be the fusion of benzene and heterocycle, preferably benzo[d][1,3]dioxolane, wherein the benzene is connected to NH which is connected to $R_1$ in formula I, more preferably benzo[d][1,3]dioxolane-4-yl; alternatively, the $C_3$~$C_{12}$ heteroaryl can be indazolyl, such as indazole-5-yl), the substituent is selected from the group consisting of $C_1$~$C_6$ alkyl, halogen (such as F, Cl, and Br), hydroxy, amino, $C_2$~$C_6$ alkynyl (such as ethynyl), $C_2$~$C_6$ alkenyl, $C_1$~$C_6$ (preferably $C_1$~$C_3$) alkyloxy (such as methoxy), cyano, nitro, trifluoromethyl, benzyl, halobenzyl (such as 3-fluorobenzyl), $C_3$~$C_6$ cycloalkyl, $C_2$~$C_6$ heterocycloalkyl, carboxyl, $C_1$~$C_6$ alkyloxy-carbonyl and -L-B;

wherein:

L is selected from $-O(CH_2)_r-$, $-N(CH_2)_r-$ or $-S(CH_2)_r-$, r is 0, 1 or 2;

B is $C_3$~$C_6$ cycloalkyl (such as cyclopropyl), substituted or unsubstituted $C_6$~$C_{10}$ aryl (such as phenyl), or substituted or unsubstituted $C_3$~$C_{12}$ heteroaryl (such as pyridyl, preferably pyridin-2-yl), the substituent is independently selected from the group consisting of $C_1$~$C_6$ alkyl, halogen (such as F), hydroxy, amino, $C_2$~$C_6$ alkynyl, $C_2$~$C_6$ alkenyl, $C_1$~$C_6$ alkyloxy, cyano, nitro, trifluoromethyl, $C_3$~$C_6$ cycloalkyl and $C_3$~$C_6$ heterocycloalkyl.

$R_2$ is hydrogen, halogen, hydroxy, amino, $C_1$~$C_6$ alkyl, $C_1$~$C_6$ haloalkyl, $C_2$~$C_6$ chain alkenyl, $C_2$~$C_6$ alkynyl, C₁~C₆ (preferably C₁~C₃) alkoxy (such as methoxy or ethoxy), C₁~C₆ (preferably C₁~C₃) alkoxy substituted by C₁~C₆ (preferably C₁~C₃) alkoxy, 3-8 membered cycloalkyloxy, C₂~C₆ chain alkenyloxy, C₂~C₆ alkynyloxy, alkoxymethyl that having 2-7 carbon atoms, C₁~C₆ alkylthio, alkylsulfinyl, C₁~C₆ alkylsulfonyl, C₁~C₆ alkylsulfinamido, cyano, carboxyl, alkoxycarbonyl alkoxy that having 2-7 carbon atoms, alkoxycarbonylalkyl that having 2-7 carbon atoms, C₁~C₆ alkylamino, dialkylamino that having 2-12 carbon atoms, N-alkylcarbamoyl that having 1-6 carbon atoms, N,N-dialkylcarbamoyl that having 2-12 carbon atoms, R₅—(CH₂)$_a$—Y—, R₅—(CH₂)$_b$—Z—(CH₂)$_a$—Y— or Het-W—(CH₂)—Y—;

X is a halogen atom (such as F or Cl);

R₃ and R₄ are independently selected from hydrogen, C₁~C₆ alkyl (preferably C₁~C₃ alkyl), R₆R₇N—(CH₂)$_c$—, R₆R₇N—(CH₂)$_c$—Y—(CH₂)$_b$— or Het-W—(CH₂)$_d$—;

R₅ is C₃~C₅ cycloalkyl (such as cyclopropyl or cyclobutyl), —NR₆R₇ or —OR₈;

R₆ and R₇ are independently selected from hydrogen, C₁~C₆ alkyl (preferably C₁~C₃ alkyl, such as methyl), Het-W—(CH₂)$_d$— or R₈—W—(CH₂)$_b$—;

R₈ is hydrogen, or C₁~C₆ (preferably C₁~C₃) alkyl;

Y is —O—, —S— or —N(R₆)—, preferably —O—;

Z is —N(R₆)— or —O—, preferably —O—;

W is —N(R₆)—, —O— or a single bond, preferably —O— or a single bond;

Het is 3~6 membered heterocycl or 5 membered heteroaryl that containing nitrogen, wherein the 3~6 membered heterocyclo can be morpholin-4-yl, 4-C₁~C₃ alkylmorpholine-3-yl (wherein 3-carbon may be racemic, or have an absolute configuration of R or S), 4-C₁~C₃ alkylmorpholine-2-yl (wherein 2-carbon may be racemic, or have an absolute configuration of R or S), thiomorpholin-4-yl, thiomorpholin-5-oxide-4-yl, thiomorpholin-S,S-dioxide-4-yl, tetrahydrofuran-3-yl (such as tetrahydrofuran-3(S)-yl or tetrahydrofuran-3(R)-yl), tetrahydrofuran-2-yl, piperidine-1-yl, N—C₁~C₃ alkylpiperidine-4-yl, 1~C₁~C₃ alkylpiperidine-3-yl (wherein 3-carbon may be racemic, or have an absolute configuration of R or S), 1~C₁~C₃ alkylpiperidine-2-yl (wherein 2-carbon may be racemic, or have an absolute configuration of R or S), 4-C₁~C₆ alkylpiperazin-1-yl (wherein C₁~C₆ alkyl is preferably C₁~C₃ alkyl, such as methyl), pyrrolidin-1-yl, N—C₁~C₃ alkylpyrrolidine-2-yl (such as (S)—N-methylpyrrolidine-2-yl or (R)—N-methylpyrrolidine-2-yl), N—C₁~C₃ alkylpyrrolidine-3-yl (such as (S)—N—C₁~C₃ alkylpyrrolidine-3-yl or (R)—N—C₁~C₃ alkylpyrrolidine-3-yl), aziridine-1-yl, tetrahydropyran-2-yl, tetrahydropyran-3-yl and tetrahydropyran-4-yl, the 5 membered heteroaryl that containing nitrogen can be imidazole-1-yl, pyrazole-1-yl, 1,2,3-triazole-1-yl, 1,2,3-triazole-2-yl, 1,2,4-triazole-1-yl, 1,2,4-triazole-4-yl, tetrazole-1-yl or tetrazole-5-yl;

a is 0~6 (such as 0, 1, 2, 3 or 4), b is 0~4 (such as 0, 1 or 2), c is 1~3 (such as 1, 2), d is 0~2 (such as 1).

In the present invention, when R₁ is phenyl substituted by halogen, the halogen may substitute at position 3 and 4 simultaneously, such as 3-chloro-4-fluorophenyl; alternatively at position 2 and 4 simultaneously, such as 4-bromo-2-fluorophenyl or 2,4-difluorophenyl; alternatively at position 2, 3 and 4 simultaneously, such as 3-chloro-2,4-difluorophenyl, 3,4-dichloro-2-fluorophenyl, 2,3,4-trifluorophenyl or 4-bromo-3-chloro-2-fluorophenyl; alternatively at position 2 and 3 simultaneously, such as 3-chloro-2-fluorophenyl; alternatively at position 3, such as 3-bromophenyl.

When B is phenyl substituted by halogen, the halogen may substitute at position 3, such as 3-fluorophenyl.

When R₁ is phenyl substituted by halogen or -L-B, the halogen or -L-B may substitute at position 3 and 4, such as 3-chloro-4-(pyridine-2-ylmethoxy)phenyl, 3-chloro-4-(cyclopropyl benzyloxy)phenyl or 3-chloro-4-(3-fluorobenzyloxy)phenyl.

When R₁ is phenyl substituted by halogen and C₁~C₃ alkoxy, the halogen and C₁~C₃ alkoxy may substitute at position 2, 4 and 5, such as 2,4-dichloro-5-methoxyphenyl; alternatively, at position 2, 3 and 4, such as 2,4-difluoro-3-methoxyphenyl; alternatively, at position 3 and 4, such as 4-chloro-3-methoxyphenyl.

When R₁ is phenyl substituted by halogen and trifluoromethyl, the halogen and trifluoromethyl may substitute at position 3 and 4, such as 4-chloro-3-(trifluoromethyl)phenyl.

In the present invention, the pharmaceutically acceptable salt of compound I is preferably a salt formed by compound I and acid. The acid can be hydrochloric acid, sulfuric acid, phosphoric acid, methanesulfonic acid, p-toluenesulphonic acid, maleic acid, fumaric acid, citric acid, tartaric acid, malic acid, lactic acid, formic acid, acetic acid, propionic acid, trifluoroacetic acid, oxalic acid, succinic acid, benzoic acid or salicylic acid.

In the present invention, the compound I is preferably selected from any one of the following compounds:

N-(4-((3-chloro-4-fluorophenyl)amino)-7-methoxyquinazolin-6-yl)-4-(dimethylamino)-2-fluorobut-2-enamide (compound 1);

(Z)—N-(4-((3-chloro-4-fluorophenyl)amino)-7-methoxyquinazolin-6-yl)-4-(dimethylamino)-2-fluorobut-2-enamide (compound 2-1);

(E)-N-(4-((3-chloro-4-fluorophenyl)amino)-7-methoxyquinazolin-6-yl)-4-(dimethylamino)-2-fluorobut-2-enamide (compound 2-2);

N-(4-((3-chloro-4-fluorophenyl)amino)-7-(2-methoxy)ethoxyquinazolin-6-yl)-4-(dimethylamino)-2-fluorobut-2-enamide (compound 3-1);

N-(4-((3-chloro-4-fluorophenyl)amino)-7-ethoxyquinazolin-6-yl)-4-(dimethylamino)-2-fluorobut-2-enamide (compound 3-2);

N-(4-((3-chloro-4-fluorophenyl)amino)-7-(2-methoxyethoxy)quinazolin-6-yl)-2-fluoro-4-morpholinobut-2-enamide (compound 3-3);

N-(4-((3-chloro-4-fluorophenyl)amino)-7-((3R)-tetrahydrofuran-3-yloxy)quinazolin-6-yl)-4-(dimethylamino)-2-fluorobut-2-enamide (compound 3-4);

N-(4-((3-chloro-4-fluorophenyl)amino)-7-((tetrahydro-2H-pyran-4-yl)methoxy)quinazolin-6-yl)-4-(dimethylamino)-2-fluorobut-2-enamide (compound 3-5);

N-(4-((3-chloro-4-fluorophenyl)amino)-7-methoxyquinazolin-6-yl)-4-(diethylamino)-2-fluorobut-2-enamide (compound 3-6);

N-(4-((3-chloro-4-fluorophenyl)amino)-7-(2-methoxyethoxy)quinazolin-6-yl)-2-fluoro-4-(4-methylpiperazin-1-yl)but-2-enamide (compound 3-7);

N-(4-((3-chloro-4-fluorophenyl)amino)-7-methoxyquinazolin-6-yl)-2-fluoro-4-((2-methoxyethyl)(methyl)amino)but-2-enamide (compound 3-8);

N-(4-((3-chloro-4-fluorophenyl)amino)-7-methoxyquinazolin-6-yl)-2-fluoro-4-(4-methyl piperazin-1-yl)but-2-enamide (compound 3-9);

N-(4-((3-chloro-4-fluorophenyl)amino)-7-methoxyquinazolin-6-yl)-2-fluoro-4-(methyl)(tetrahydrofuran-3-yl)amino)but-2-enamide (compound 3-10);

N-(4-((3-chloro-4-fluorophenyl)amino)-7-methoxyquinazolin-6-yl)-4-(2-(dimethylamino)ethoxy)-2-fluorobut-2-enamide (compound 3-11);

N-(4-((3-chloro-4-fluorophenyl)amino)-7-methoxyquinazolin-6-yl)-2-fluoro-3-(1-methyl pyrrolidine-2(S)-yl)acrylamide (compound 3-12);

N-(4-((3-chloro-4-(pyridin-2-ylmethoxy)phenyl)amino)-7-methoxyquinazolin-6-yl)-4-(dimethylamino)-2-fluorobut-2-enamide (compound 3-13);

N-(4-(4-((3-fluorobenzyloxy)-3-chlorophenyl)amino)-7-methoxyquinazolin-6-yl)-4-(dim ethylamino)-2-fluorobut-2-enamide (compound 3-14);

N-(4-(1-(3-fluorobenzyl)-1H-indazol-5-ylamino)-7-methoxyquinazolin-6-yl)-4-(dimethylamino)-2-fluorobut-2-enamide (compound 3-15);

4-(dimethylamino)-N-(4-((3-ethynylphenyl)amino)-7-methoxyquinazolin-6-yl)-2-fluorobut-2-enamide (compound 3-16);

N-(4-((2,4-dichloro-5-methoxyphenyl)amino)-7-methoxyquinazolin-6-yl)-4-(dimethylamino)-2-fluorobut-2-enamide (compound 3-17);

N-(4-((5-chlorobenzo[d][1,3]dioxol-4-yl)amino)-7-methoxyquinazolin-6-yl)-4-(dimethyl amino)-2-fluorobut-2-enamide (compound 3-18);

N-(4-((4-chloro-3-(trifluoromethyl)phenyl)amino)-7-methoxyquinazolin-6-yl)-4-(dimeth ylamino)-2-fluorobut-2-enamide (compound 3-19);

N-(4-((3-bromophenyl)amino)-7-methoxyquinazolin-6-yl)-4-(dimethylamino)-2-fluorobut-2-enamide (compound 3-20);

N-(4-((3-chloro-2-fluorophenyl)amino)-7-methoxyquinazolin-6-yl)-4-(dimethylamino)-2-fluorobut-2-enamide (compound 3-21);

N-(4-((4-bromo-2-fluorophenyl)amino)-7-methoxyquinazolin-6-yl)-4-(dimethylamino)-2-fluorobut-2-enamide (compound 3-22);

N-(4-((3-chloro-2,4-difluorophenyl)amino)-7-methoxyquinazolin-6-yl)-4-(dimethylamino)-2-fluorobut-2-enamide (compound 3-23);

N-(4-((3,4-dichloro-2-fluorophenyl)amino)-7-methoxyquinazolin-6-yl)-4-(dimethylamino)-2-fluorobut-2-enamide (compound 3-24);

N-(4-((4-bromo-3-chloro-2-fluorophenyl)amino)-7-methoxyquinazolin-6-yl)-4-(dimethylamino)-2-fluorobut-2-enamide (compound 3-25);

(Z)—N-(4-((3-chloro-4-(pyridin-2-ylmethoxy)phenyl)amino)-7-methoxyquinazolin-6-yl)-4-(dimethylamino)-2-fluorobut-2-enamide (compound 4-1);

(E)-N-(4-((3-chloro-4-(pyridin-2-ylmethoxy)phenyl)amino)-7-methoxyquinazolin-6-yl)-4-(dimethylamino)-2-fluorobut-2-enamide (compound 4-2);

N-(4-((3-chloro-4-fluorophenyl)amino)-7-(3-morpholinopropoxy)quinazolin-6-yl)-2-fluoroacrylamide (compound 5);

N-(4-((3-chloro-2,4-difluorophenyl)amino)-7-((1-methylpiperidin-4-yl)methoxy)quinazolin-6-yl)-2-fluoroacrylamide (compound 6);

N-(4-((3-chloro-4-fluorophenyl)amino)-7-methoxyquinazolin-6-yl)-2-fluoro-4-(piperidin-1-yl)but-2-enamide (compound 7);

(Z)—N-(4-((3-chloro-4-fluorophenyl)amino)-7-methoxyquinazolin-6-yl)-2-fluoro-4-(piperidin-1-yl)but-2-enamide (compound 8-1);

(E)-N-(4-((3-chloro-4-fluorophenyl)amino)-7-methoxyquinazolin-6-yl)-2-fluoro-4-(piperidin-1-yl)but-2-enamide (compound 8-2);

N-(4-((3-chloro-4-(pyridin-2-ylmethoxyl)phenyl)amino)-7-ethoxyquinazolin-6-yl)-4-(dimethylamino)-2-fluorobut-2-enamide (compound 9);

(S)—N-(4-((3-chloro-4-fluorophenyl)amino)-7-(tetrahydrofuran-3-yl)oxy)quinazolin-6-yl)-2-fluoro-4-morpholinobut-2-enamide (compound 10);

(S)—N-(4-((3-chloro-4-fluorophenyl)amino)-7-((tetrahydrofuran-3-yl)oxy)quinazolin-6-yl)-4-(dimethylamino)-2-fluorobut-2-enamide (compound 11);

N-(4-((3-chloro-4-fluorophenyl)amino)-7-methoxyquinazolin-6-yl)-2-fluoro-4-morpholinobut-2-enamide (compound 12);

N-(4-((3-bromophenyl)amino)-7-ethoxyquinazolin-6-yl)-2-fluoro-4-(piperidin-1-yl)but-2-enamide (compound 13);

N-(4-((3-chloro-4-fluorophenyl)amino)-7-(2-methoxyethoxy)quinazolin-6-yl)-2-fluoro-4-(piperidin-1-yl)but-2-enamide (compound 14);

N-(4-((3-chloro-4-(pyridin-2-ylmethoxy)phenyl)amino)-7-ethoxyquinazolin-6-yl)-2-fluoro-4-(piperidin-1-yl)but-2-enamide (compound 15);

N-(4-((3-bromophenyl)amino)-7-ethoxyquinazolin-6-yl)-4-(dimethylamino)-2-fluorobut-2-enamide (compound 16);

N-(4-((3-bromophenyl)amino)-7-ethoxyquinazolin-6-yl)-2-fluoro-4-morpholinobut-2-enamide (compound 17);

N-(4-((3-chloro-4-fluorophenyl)amino)-7-methoxyquinazolin-6-yl)-2-fluoro-4-(pyrrolidin-1-yl)but-2-enamide (compound 18);

(Z)—N-(4-((3-chloro-4-(pyridin-2-ylmethoxy)phenyl)amino)-7-ethoxyquinazolin-6-yl)-4-(dimethylamino)-2-fluorobut-2-enamide (compound 19-1);

(E)-N-(4-((3-chloro-4-(pyridin-2-ylmethoxy)phenyl)amino)-7-ethoxyquinazolin-6-yl)-4-(dimethylamino)-2-fluorobut-2-enamide (compound 19-2);

(S,Z)—N-(4-((3-chloro-4-fluorophenyl)amino)-7-((tetrahydrofuran-3-yl)oxy)quinazolin-6-yl)-2-fluoro-4-morpholinobut-2-enamide (compound 20-1);

(S,E)-N-(4-((3-chloro-4-fluorophenyl)amino)-7-((tetrahydrofuran-3-yl)oxy)quinazolin-6-yl)-2-fluoro-4-morpholinobut-2-enamide (compound 20-2);

(S,Z)—N-(4-((3-chloro-4-fluorophenyl)amino)-7-((tetrahydrofuran-3-yl)oxy)quinazolin-6-yl)-4-(dimethylamino)-2-fluorobut-2-enamide (compound 21-1);

(S,E)-N-(4-((3-chloro-4-fluorophenyl)amino)-7-((tetrahydrofuran-3-yl)oxy)quinazolin-6-yl)-4-(dimethylamino)-2-fluorobut-2-enamide (compound 21-2);

(Z)—N-(4-((3-chloro-4-fluorophenyl)amino)-7-methoxyquinazolin-6-yl)-2-fluoro-4-morpholinobut-2-enamide (compound 22-1);

(E)-N-(4-((3-chloro-4-fluorophenyl)amino)-7-methoxyquinazolin-6-yl)-2-fluoro-4-morpholinobut-2-enamide (compound 22-2);

N-[4-(4-bromo-2-fluorophenylamino)-7-(3-morpholinopropoxy)quinazolin-6-yl]-2-fluoroacrylamide (compound 23);

N-[4-((3-chloro-2,4-difluorophenyl)amino)-7-(3-morpholinopropoxy)quinazolin-6-yl]-2-fluoroacrylamide (compound 24);

N-[4-(3-ethynylphenylamino)-7-(3-morpholinopropoxy)quinazolin-6-yl]-2-fluoroacrylamide (compound 25);

N-[4-((3-chloro-2-fluorophenyl)amino)-7-(3-morpholinopropoxy)quinazolin-6-yl]-2-fluoroacrylamide (compound 26);

N-[4-((2,4-dichloro-5-methoxyphenyl)amino)-7-(3-morpholinopropoxy)quinazolin-6-yl]-2-fluoroacrylamide (compound 27);

N-[4-((3-bromophenyl)amino)-7-(3-morpholinopropoxy)quinazolin-6-yl]-2-fluoroacrylamide (compound 28);

N-[4-((3-chloro-4-((3-fluorobenzyl)oxy)phenyl)amino)-7-(3-morpholinopropoxy)quinazolin-6-yl]-2-fluoroacrylamide (compound 29);

N-[4-((3,4-dichloro-2-fluorophenyl)amino)-7-(3-morpholinopropoxy)quinazolin-6-yl]-2-fluoroacrylamide (compound 30);
N-[4-((2,4-difluorophenyl)amino)-7-(3-morpholinopropoxy)quinazolin-6-yl]-2-fluoroacrylamide (compound 31);
2-fluoro-N-(7-(3-morpholinopropoxy)-4-((2,3,4-trifluorophenyl)amino)quinazolin-6-yl]acrylamide (compound 32);
N-[4-((2,4-dichlorophenyl)amino)-7-(3-morpholinopropoxy)quinazolin-6-yl]-2-fluoroacrylamide (compound 33);
2-chloro-N-(4-((3-chloro-2,4-difluorophenyl)amino)-7-(3-morpholinopropoxy)quinazolin-6-yl)acrylamide (compound 34);
2-chloro-N-(4-((3-chloro-4-fluorophenyl)amino)-7-(3-morpholinopropoxy)quinazolin-6-yl)acrylamide (compound 35);
N-(4-((2,4-difluoro-3-methoxyphenyl)amino)-7-(3-morpholinopropoxy)quinazolin-6-yl)-2-fluoroacrylamide (compound 36);
N-(4-((4-chloro-3-methoxyphenyl)amino)-7-(3-morpholinopropoxy)quinazolin-6-yl)-2-fluoroacrylamide (compound 37);
N-(4-((4-bromo-3-chloro-2-fluorophenyl)amino)-7-(3-morpholinopropoxy)quinazolin-6-yl)-2-fluoroacrylamide (compound 38);
N-(4-((3-chloro-4-((3-fluorobenzyl)oxy)phenyl)amino)-7-ethoxyquinazolin-6-yl)-2-fluoroacrylamide (compound 39);
N-(4-((3-chloro-4-fluorophenyl)amino)-7-(3-(piperidine-1-yl)propoxy)quinazolin-6-yl)-2-fluoroacrylamide (compound 40);
2-chloro-N-(4-((3-chloro-4-fluorophenyl)amino)-7-(3-morpholinopropoxy)quinazolin-6-yl)acrylamide (compound 41);
N-(4-((3-chloro-4-fluorophenyl)amino)-7-(3-(dimethylamino)propoxy)quinazolin-6-yl)-2-fluoroacrylamide (compound 42);
N-(4-((3-chloro-4-fluorophenyl)amino)-7-(3-(pyrrolidin-1-yl)propoxy)quinazolin-6-yl)-2-fluoroacrylamide (compound 43);
N-(4-((3-chloro-4-fluorophenyl)amino)-7-(3-(4-methylpiperazin-1-yl)propoxy)quinazolin-6-yl)-2-fluoroacrylamide (compound 44);
(R)—N-(4-((3-chloro-2,4-difluorophenyl)amino)-7-((tetrahydrofuran-3-yl)methoxy)quinazolin-6-yl)-2-fluoroacrylamide (compound 45);
(R)—N-(4-((3-chloro-2,4-difluorophenyl)amino)-7-((tetrahydrofuran-3-yl)methoxy)quinazolin-6-yl)-2-fluoroacrylamide (compound 46);
N-(4-((3-chloro-2,4-difluorophenyl)amino)-7-(cyclobutylmethoxy)quinazolin-6-yl)-2-fluoroacrylamide (compound 47);
N-(4-((3-chloro-2,4-difluorophenyl)amino)-7-(cyclopropylmethoxy)quinazolin-6-yl)-2-fluoroacrylamide (compound 48);
N-(4-((3-chloro-4-fluorophenyl)amino)-7-((1-methylpiperidin-4-yl)oxy)quinazolin-6-yl)-2-fluoroacrylamide (compound 49);
(R)—N-(4-((3-chloro-2,4-difluorophenyl)amino)-7-((1-methylpyrrolidin-3-yl)oxy)quinazolin-6-yl)-2-fluoroacrylamide (compound 50);
(S)—N-(4-((3-chloro-2,4-difluorophenyl)amino)-7-((1-methylpyrrolidin-3-yl)oxy)quinazolin-6-yl)-2-fluoroacrylamide (compound 51);
N-(4-((3-bromophenyl)amino)-7-methoxyquinazolin-6-yl)-2-fluoroacrylamide (compound 52);
N-(4-((3-bromophenyl)amino)-7-ethoxyquinazolin-6-yl)-2-fluoroacrylamide (compound 53);
2-fluoro-N-(7-methoxy-4-((3-(trifluoromethyl)phenyl)amino)quinazolin-6-yl)acrylamide (compound 54);
N-(7-ethoxy-4-((3-(trifluoromethyl)phenyl)amino)quinazolin-6-yl)-2-fluoroacrylamide (compound 55);
N-(4-((3-chloro-4-fluorophenyl)amino)-7-methoxyquinazolin-6-yl)-2-fluoroacrylamide (compound 56);
2-chloro-N-(4-((3-chloro-4-fluorophenyl)amino)-7-methoxyquinazolin-6-yl)acrylamide (compound 57);
2-chloro-N-(7-ethoxy-4-((3-(trifluoromethyl)phenyl)amino)quinazolin-6-yl)acrylamide (compound 58);
N-(4-((3-bromophenyl)amino)-7-ethoxyquinazolin-6-yl)-2-chloroacrylamide (compound 59);
2-chloro-N-(4-((3-chloro-4-((3-fluorobenzyl)oxy)phenyl)amino)-7-ethoxyquinazolin-6-yl)acrylamide (compound 60);
N-(4-((3-chloro-4-(cyclopropylbenzyloxy)phenyl)amino)-7-(3-morpholinopropoxy)quinazolin-6-yl)-2-fluoroacrylamide (compound 61);
2-chloro-N-(4-((3-chloro-4-(cyclopropylbenzyloxy)phenyl)amino)-7-(3-morpholinopropoxy)quinazolin-6-yl)acrylamide (compound 62);
(R)—N-(4-((3-chloro-4-fluorophenyl)amino)-7-((1-methylpyrrolidin-3-yl)oxy)quinazolin-6-yl)-2-fluoroacrylamide (compound 63);
(S)—N-(4-((3-chloro-4-fluorophenyl)amino)-7-((1-methylpyrrolidin-3-yl)oxy)quinazolin-6-yl)-2-fluoroacrylamide (compound 64);
(R)—N-(4-((3-chloro-4-fluorophenyl)amino)-7-((4-methylmorpholin-3-yl)methoxy)quinazolin-6-yl)-2-fluoroacrylamide (compound 65);
(R)-2-chloro-N-(4-((3-chloro-4-fluorophenyl)amino)-7-((4-methylmorpholin-3-yl)methoxy)quinazolin-6-yl)acrylamide (compound 66);
N-(4-((3-chloro-4-fluorophenyl)amino)-7-(2-(piperidin-1-yl)ethoxy)quinazolin-6-yl)-2-fluoroacrylamide (compound 67);
2-chloro-N-(4-((3-chloro-4-fluorophenyl)amino)-7-(2-(piperidin-1-yl)ethoxy)quinazolin-6-yl)acrylamide (compound 68);
2-chloro-N-(4-((3-chloro-4-(pyridin-2-ylmethoxy)phenyl)amino)-7-ethoxyquinazolin-6-yl)acrylamide (compound 69);
2-chloro-N-(4-((3-chloro-4-(cyclopropylmethoxy)phenyl)amino)-7-((1-methylpiperidin-4-yl)methoxy)quinazolin-6-yl)acrylamide (compound 70);
N-(4-((3-chloro-4-(cyclopropylmethoxy)phenyl)amino)-7-((1-methylpiperidin-4-yl)methoxy)quinazolin-6-yl)-2-fluoroacrylamide (compound 71);
(S)—N-(4-((3-chloro-4-fluorophenyl)amino)-7-(4-methylmorpholin-3-yl)methoxy)quinazolin-6-yl)-2-fluoroacrylamide (compound 72);
(S)—N-(4-((3-chloro-4-fluorophenyl)amino)-7-((1-methylpiperidin-3-yl)methoxy)quinazolin-6-yl)-2-fluoroacrylamide (compound 73);
(R)—N-(4-((3-chloro-4-fluorophenyl)amino)-7-(1-methylpiperidin-3-yl)methoxy)quinazolin-6-yl)-2-fluoroacrylamide (compound 74);
(S)—N-(4-((3-chloro-4-fluorophenyl)amino)-7-((4-methylmorpholin-2-yl)methoxy)quinazolin-6-yl)-2-fluoroacrylamide (compound 75);
(R)—N-(4-((3-chloro-4-fluorophenyl)amino)-7-((4-methylmorpholin-2-yl)methoxy)quinazolin-6-yl)-2-fluoroacrylamide (compound 76);

N-(4-((3-chloro-4-fluorophenyl)amino)-7-(2-(1-methylpiperidin-4-yl)ethoxy)quinazolin-6-yl)-2-fluoroacrylamide (compound 77);

N-(4-((3-chloro-4-fluorophenyl)amino)-7-(2-(4-methylpiperazin-1-yl)ethoxy)quinazolin-6-yl)-2-fluoroacrylamide (compound 78);

N-(4-((3-chloro-4-fluorophenyl)amino)-7-(2-morpholinoethoxy)quinazolin-6-yl)-2-fluoroacrylamide (compound 79);

(R)—N-(4-((3-chloro-4-fluorophenyl)amino)-7-(2-(1-methylpyrrolidin-2-yl)ethoxy)quinazolin-6-yl)-2-fluoroacrylamide (compound 80);

(S)—N-(4-((3-chloro-4-fluorophenyl)amino)-7-(2-(1-methylpyrrolidin-2-yl)ethoxy)quinazolin-6-yl)-2-fluoroacrylamide (compound 81);

(R)—N-(4-((3-chloro-4-fluorophenyl)amino)-7-(2-(1-methylpiperidin-2-yl)ethoxy)quinazolin-6-yl)-2-fluoroacrylamide (compound 82);

(S)—N-(4-((3-chloro-4-fluorophenyl)amino)-7-(2-(1-methylpiperidin-2-yl)ethoxy)quinazolin-6-yl)-2-fluoroacrylamide (compound 83);

(R)—N-(4-((3-chloro-4-fluorophenyl)amino)-7-(2-(1-methylpiperidin-3-yl)ethoxy)quinazolin-6-yl)-2-fluoroacrylamide (compound 84);

(S)—N-(4-((3-chloro-4-fluorophenyl)amino)-7-(2-(1-methylpiperidin-3-yl)ethoxy)quinazolin-6-yl)-2-fluoroacrylamide (compound 85);

N-(4-((3-chloro-4-fluorophenyl)amino)-7-((1-methylpiperidin-4-yl)methoxy)quinazolin-6-yl)-2-fluoroacrylamide (compound 86);

N-(4-((3-bromophenyl)amino)-7-((1-methylpiperidin-4-yl)methoxy)quinazolin-6-yl)-2-fluoroacrylamide (compound 87);

(S)-2-chloro-N-(4-((3-chloro-4-fluorophenyl)amino)-7-(4-methylmorpholin-3-yl)methoxy)quinazolin-6-yl)acrylamide (compound 88).

In the present invention, the description " . . . yl that having x~y carbon atoms" (wherein x and y are numbers) refers to the total number of carbon atoms in the group.

The compound of formula (I) in the present invention can be synthesized by several preparation methods in organic synthesis and pharmaceutical chemistry field and also the methods well known by a skilled person. The compound in the present invention can be synthesized by the method described below together with the synthesis methods known in the field of organic chemistry or the change of them which can be understood by a person skilled in the art.

The preparation of the compound of formula (I) in the present invention can be synthesized with readily available starting materials and by the following general method and procedure. It will be appreciated that when typical or preferred process operating conditions (i.e., reaction temperature, time, mole ratio of reactants, solvent, pressure etc.) are given, it is also possible to use other process operating conditions, unless otherwise specified. Optimum reaction conditions may vary with particular reactants or solvent, but such conditions can be made by a person skilled in the art through conventional process optimization.

As described herein, the preparation of the formula (I) compound can be monitored by any suitable methods known in the art. For example, nuclear magnetic resonance, infrared spectroscopy, spectrophotometry or mass spectrometry, HPLC or thin layer chromatography can monitor the formation of the product.

The preparation of compounds can involve protection and deprotection of multiple chemical functional groups. Whether to carry out protection and deprotection and the selection of appropriate protecting groups can be readily determined by a person skilled in the art. The chemical process of protection can be found for example, in Greene et al., "Protective Groups in Organic Synthesis", Second Edition, Wiley&Sons, 1991, which is hereby incorporated by reference in entirety.

The chemical reactions described may be carried out in a suitable solvent, and the solvent can be readily selected by a person skilled in the art. The suitable solvent does not react with the starting materials, intermediates or products at the temperature that the reaction is carried out at, and the temperature of the reaction can range from the freezing point to the boiling point of the solvent. The given reaction may be carried out in a solvent or a mixture of solvents. Depending on the particular reaction step, suitable solvents can be selected.

Generally, the compounds in the present invention can be prepared by two reaction routes and processes described below, but it is not limited to the reagents and solvents of the reaction conditions.

Thus, the present invention also relates a process for preparing compound I, which is any one of the following methods:

Method 1: in a solvent, in the presence of an inorganic base, the reaction between compound III and II is carried out as follows;

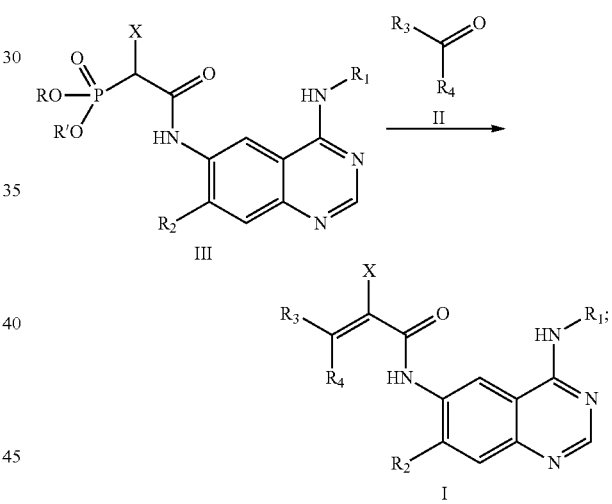

wherein, each group has the meaning given above, R and R' are independently selected from $C_1$~$C_6$ alkyl (preferably $C_1$~$C_3$ alkyl).

Method 2: in a solvent, in the presence of an organic base or an inorganic base, the condensation reaction between compound V and VI is carried out as follows;

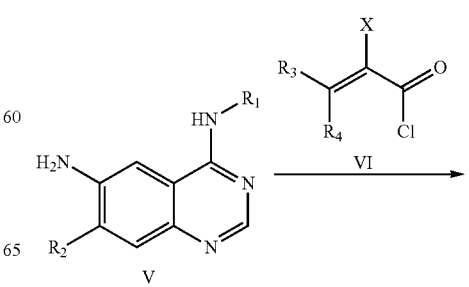

-continued

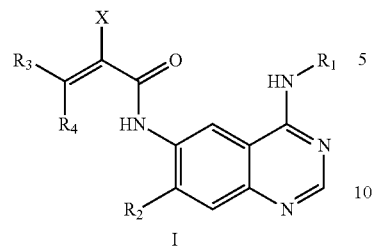

I wherein, each group has the meaning given above.

In the present invention, the methods and conditions used for the method 1 and method 2 can be that commonly used for this two kinds of reactions in this field, while the present invention uses preferably the following conditions:

wherein, in method 1, the inorganic base is preferably selected from the group consisting of alkali metal hydride, alkali metal hydroxide and alkali metal alkoxide. Wherein the alkali metal hydride is preferably selected from sodium hydride and/or potassium hydride and etc. The alkaline metal hydroxide is preferably selected from the group consisting of sodium hydroxide, potassium hydroxide and lithium hydroxide. The alkaline metal alkoxide is preferably selected from the group consisting of sodium methoxide, sodium ethoxide, potassium tert-butoxide and sodium tert-butoxide etc.

The compound II can be purchased directly, or made from a commercially available reagent by methods that have been reported in literatures.

In method 2, the organic base is preferably selected from the group consisting of triethylamine, N,N-diisopropylethylamine, pyridine and 4-dimethylaminopyridine. The inorganic base is preferably selected from the group consisting of potassium carbonate, sodium carbonate, lithium carbonate, cesium carbonate, potassium bicarbonate, sodium bicarbonate, sodium hydroxide, potassium hydroxide and lithium hydroxide.

The compound V and VI can be purchased directly, or made from commercially available reagents by methods that have been reported in literatures.

In method 1, the compound III can be prepared by the following method: in a solvent, in the presence of an organic base or an inorganic base, a condensation reaction between compound V and VI is carried out;

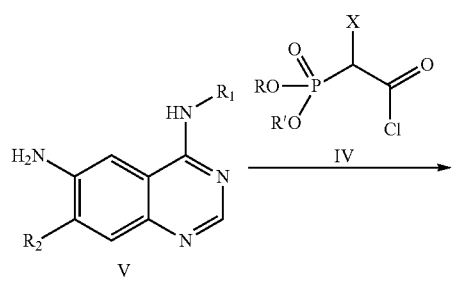

-continued

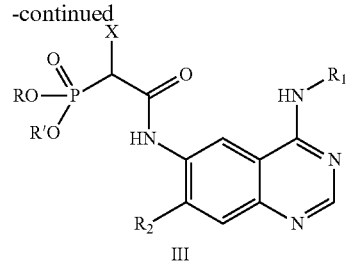

III wherein, each group has the meaning given above, R and R' are independently selected from $C_1$~$C_6$ alkyl (preferably $C_1$~$C_3$ alkyl).

Wherein, the methods and conditions used for the condensation reaction can be that commonly used for this kind of reactions in the field, in the present invention, the organic base is preferably selected from the group consisting of triethylamine, N,N-diisopropylethylamine, pyridine, 4-dimethylaminopyridine and etc. The inorganic base is preferably selected from the group consisting of potassium carbonate, sodium carbonate, lithium carbonate, cesium carbonate, potassium bicarbonate, sodium bicarbonate, sodium hydroxide, potassium hydroxide and lithium hydroxide.

The compound V and VI can be purchased directly, or made from commercially available reagents by methods that have been reported in literatures.

In the present invention, the compound I can be preferably prepared by following method:

Reaction Route 1:

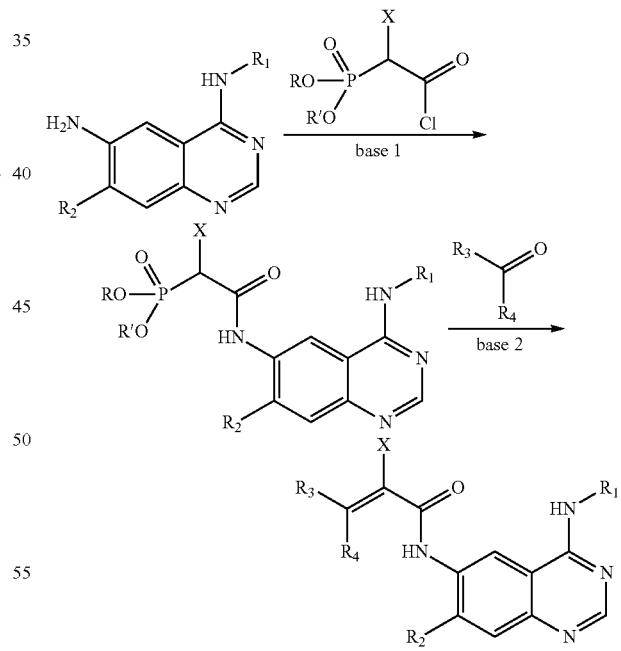

wherein, the base 1 is selected from an organic base such as triethylamine, N,N-diisopropylethylamine, pyridine, 4-dimethylaminopyridine and so on, or from an inorganic base such as sodium hydroxide, potassium hydroxide, lithium hydroxide, potassium carbonate, sodium carbonate, lithium carbonate, cesium carbonate, potassium bicarbonate or sodium bicarbonate and so on. The base 2 is selected from an inorganic base such as sodium hydride, potassium hydride, sodium hydroxide, potassium hydroxide, lithium hydroxide, sodium methoxide, sodium ethoxide, potassium tert-butoxide or sodium tert-butoxide and so on.

Reaction Route 2:

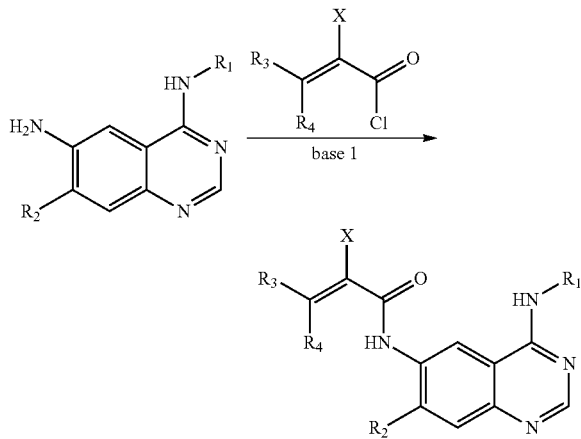

wherein, the base 1 is selected from an organic base such as triethylamine, N,N-diisopropylethylamine, pyridine, 4-dimethylaminopyridine and so on, or from an inorganic base such as sodium hydroxide, potassium hydroxide, lithium hydroxide, potassium carbonate, sodium carbonate, lithium carbonate, cesium carbonate, potassium bicarbonate or sodium bicarbonate and so on. Chloride compounds can be purchased directly, or prepared from the carboxylic acid and thionyl chloride, oxalyl chloride etc.

The present invention also relates to a compound III which is an intermediate for preparing the compound I mentioned-above;

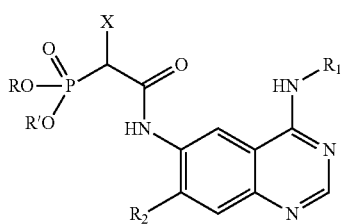

III wherein, each group has the meaning given above, R and R' are independently selected from $C_1$~$C_6$ alkyl (preferably $C_1$~$C_3$ alkyl).

The present invention also relates to a pharmaceutical composition containing the compound of formula I mentioned above or the pharmaceutically acceptable salt thereof; or their solvates.

Wherein, the composition is composed of one or more compounds of formula (I), or the pharmaceutically acceptable salt thereof, or their solvates and at least one kind of a pharmaceutical excipient. The selection of the pharmaceutical excipient depending on the administration route and action features, typically may be fillers, diluents, binders, wetting agents, disintegrants, lubricants, emulsifiers or suspending agents etc.

The pharmaceutical composition in the present invention can be administered by oral, injection (intravenous, intramuscular, subcutaneous and intracoronary), sublingual, buccal, rectal, urethra, vaginal, and nasal, inhalation or topical routes, preferred route is oral.

The present invention also relates to a use of the compounds of formula I or the pharmaceutical composition mentioned-above in preparing EGFR tyrosine kinase inhibitors, HER2 tyrosine kinase inhibitors or HER4 tyrosine kinase inhibitors, or in preparing medicine for treating or preventing tumor diseases.

In the present invention, "alkyl" refers to saturated branched or straight aliphatic hydrocarbon radical having the indicated number of carbonatoms. For example, $C_1$-$C_{10}$, the definition of "$C_1$-$C_{10}$ alkyl" refers to the groups having 1, 2, 3, 4, 5, 6, 7, 8, 9 or 10 carbon atoms in a linear or branched structure. For example, "$C_1$-$C_{10}$ alkyl" specifically includes methyl, ethyl, n-propyl, isopropyl, n-butyl, t-butyl, isobutyl, pentyl, hexyl, heptyl, octyl, nonyl, decyl, and so on.

The term "alkoxy" refers to a non-cyclic alkyl group having indicated number of carbon atoms attached through an oxygen bridge. Thus, "alkoxy" includes the definition of alkyl mentioned above.

The term "heterocyclo" refers to a stable non-aromatic cyclic group which consists of carbon atoms and heteroatoms selected from the group consisting of nitrogen, oxygen and sulfur atoms. The nitrogen, carbon or sulfur atoms in the heterocyclo group can be oxidized optionally. The nitrogen atom can be optionally further substituted by other groups to form a tertiary amine or a quaternary ammonium salt. For example, "3~6 membered heterocyclo" can include aziridinyl, tetrahydrofuran-2-yl, morpholin-4-yl, thiomorpholin-4-yl, thiomorpholin-S-oxide-4-yl, piperidine-1-yl, N-alkylpiperidine-4-yl, pyrrolidin-1-yl, N-alkylpyrrolidin-2-yl, piperazin-1-yl, 4-alkyl-piperazin-1-yl, and so on.

The term "heteroaryl" refers to a stable aromatic group which comprises 1 to 5 heteroatoms selected from the group consisting of nitrogen, oxygen and sulfur atoms. In the present invention, the aromatic group is preferred formed by a benzene ring fused with another ring containing nitrogen, oxygen, sulfur atom etc., wherein the number of heteroatom may be 1, 2 or 3, including indazolyl, iso-indazolyl, indolyl, isoindolo, benzofuryl, benzothienyl, benzo[d][1,3]dioxolanyl, benzothiazolyl, benzooxazolyl, quinolinyl, isoquinolinyl, quinazolinyl and so on.

In the present invention, the mentioned optimized conditions can be optionally combined without departing from the general knowledge in this field to obtain preferred embodiments.

The starting materials or intermediates in the present invention can be purchased directly, or prepared according to methods described in the embodiments section of the literature.

The positive effects of the present invention are that provide a novel kind of quinazoline derivatives, data of pharmacodynamic examples indicate that the quinazoline derivatives have inhibition to EGFR tyrosine kinases at a molecular level, and also have significant inhibition of proliferation to the tumor cells that are associated with the activity of EGFR tyrosine kinases at a cellular level.

DETAILED DESCRIPTION OF THE PREFERRED EMBODIMENT

The invention was further described by embodiments, but the scope of the invention is not intended to be limited by the following embodiments. In the following embodiments, the experimental methods without specific condition, can be carried on by conventional methods and conditions or according to the commodity instruction.

Example 1

The preparation of N-(4-((3-chloro-4-fluorophenyl)amino)-7-methoxyquinazolin-6-yl)-4-(dimethylamino)-2-fluorobut-2-enamide (Compound 1)

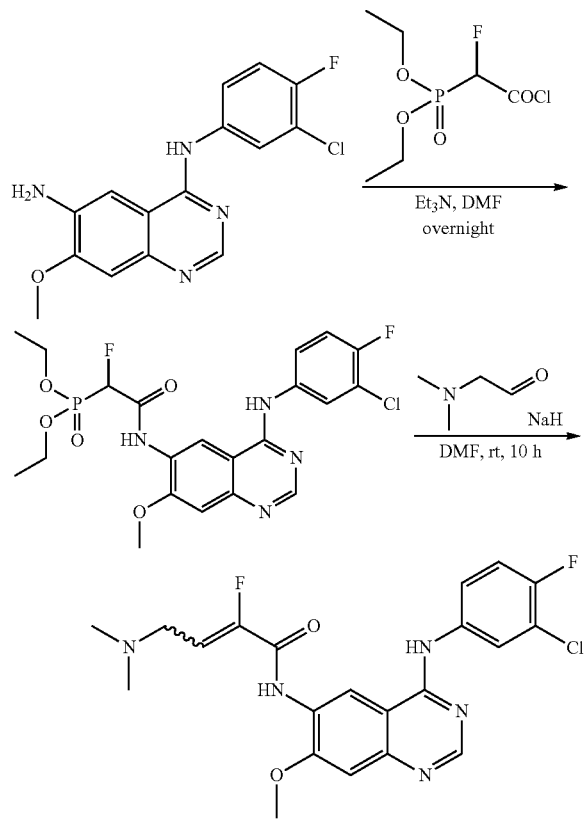

Step 1: The preparation of diethyl (2-((4-((3-chloro-4-fluorophenyl)amino)-7-methoxy-quinazolin-6-yl)amino)-1-fluoro-2-oxoethyl)phosphonate Starting material: 6-amino-4-(3-chloro-4-fluorophenylamino)-7-methoxy-quinazoline was prepared according to the method in *J. Med Chem* 2009, 52, 6880-6888.

Starting material: diethyl (2-chloro-1-fluoro-2-oxoethyl) phosphonate was prepared according to the method in *Heterocycles,* 2004, 63, 699-706.

6-amino-4-(3-chloro-4-fluorophenylamino)-7-methoxy-quinazoline (1.0 eq.) and triethylamine (1.5 eq.) were dissolved in DMF (10 ml), and the mixture was stirred at 0° C. for 30 min. A solution of diethyl (2-chloro-1-fluoro-2-oxoethyl)phosphonate (1.5 eq.) in DMF (5 ml) was added dropwise slowly into the mixture mentioned above, and stirred overnight at room temperature. After the reaction finished, the mixture was quenched with saturated NaHCO$_3$, extracted with EtOAc, and the organic phase was dried over anhydrous sodium sulfate, concentrated to dryness under reduced pressure, then the crude product was purified by column chromatography (mobile phase 40:1 DCM/MeOH) and a light yellow solid of diethyl (2-((4-((3-chloro-4-fluorophenyl)amino)-7-methoxy-quinazolin-6-yl)amino)-1-fluoro-2-oxoethyl)phosphonate was given. (50% yield).

$^1$H NMR (500 MHz, DMSO) δ 9.94 (s, 1H), 9.64 (s, 1H), 8.89 (s, 1H), 8.55 (s, 1H), 8.09 (dd, J$_1$=6.5 Hz, J$_2$=2.5 Hz, 1H), 7.78-7.75 (m, 1H), 7.43 (t, J=9.0 Hz, 1H), 7.34 (s, 1H), 6.02 (dd, J$_1$=45.0 Hz, J$_2$=11.0 Hz, 1H), 4.23-4.18 (m, 4H), 4.03 (s, 3H), 1.32-1.27 (m, 6H). HRMS (ESI): m/z calcd for (C$_{21}$H$_{22}$ClF$_2$N$_4$O$_5$P+H)$^+$: 515.1063. found: 515.1053.

Step 2: The preparation of N-(4-((3-chloro-4-fluorophenyl)amino)-7-methoxyquinazolin-6-yl)-4-(dimethylamino)-2-fluorobut-2-enamide Starting material: 2-(dimethylamino)-acetaldehyde sulfite was prepared according to the method in WO2007/85638.

Diethyl (2-((4-((3-chloro-4-fluorophenyl)amino)-7-methoxyquinazolin-6-yl)amino)-1-fluoro-2-oxoethyl)phosphonate (1 eq.) and NaH (1.5 eq.) were dissolved in DMF (10 ml), and stirred at 0° C. for 30 min, then 2-(dimethylamino)-acetaldehyde sulfite (2.0 eq.) was added, ice bath was removed, and then the mixture warmed to room temperature naturally, and the reaction was stirred for another 3-5 h. After the reaction finished, the mixture was quenched with saturated NaHCO$_3$, extracted with EtOAc, and the organic phase was dried over anhydrous sodium sulfate, concentrated to dryness under reduced pressure, the crude product was purified by column chromatography (mobile phase 30:1 DCM/MeOH) and pale yellow of N-(4-((3-chloro-4-fluorophenyl)amino)-7-methoxyquinazolin-6-yl)-4-(dimethylamino)-2-fluorobut-2-enamide was given. MS (ESI$^+$): m/z=448, 449, 450 [M+H]$^+$.

Rf values: 0.30 (Silica gel, ethyl acetate/methanol=5:1; two isomers were not separated);

0.53, 0.56 (Silica gel, dichloromethane/methanol=10:1; two isomers were separated).

Example 2

The preparation of (Z)—N-(4-((3-chloro-4-fluorophenyl)amino)-7-methoxyquinazolin-6-yl)-4-(dimethylamino)-2-fluorobut-2-enamide and (E)-N-(4-((3-chloro-4-fluorophenyl)amino)-7-methoxyquinazolin-6-yl)-4-(dimethylamino)-2-fluorobut-2-enamide

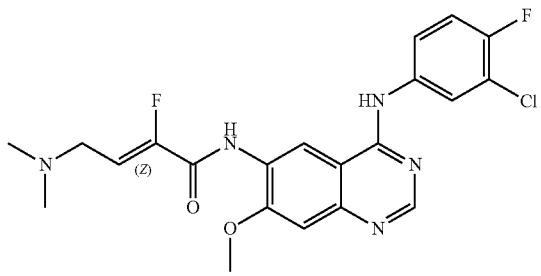

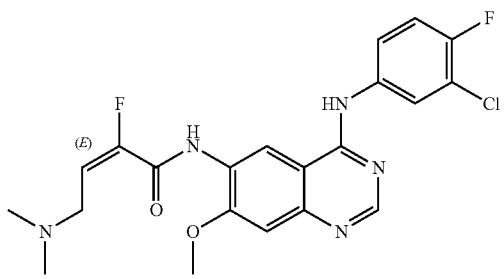

Use Gilson 215 semi-preparative chromatography (322 pump, 156 UV detector) to separate the mixture of cis and trans-isomers obtained in example 1.

Column: Phenomenex Gimini 30×250 mm, 10 μm;

Detection wavelength: 254 nm;

Column temperature: room temperature;

Sample treatment method: sample (a mixture of cis and trans isomers) was dissolved in methanol, filtered. Concentration: 22 mg/ml, the volume of each needle injection was 800 μL.

Mobile phase: water:acetonitrile (with 0.05% aqueous ammonia)=49:51

|  | Time (min) | Water (%) | Acetonitrile(%) |
|---|---|---|---|
| Gradient: | 0 | 49 | 51 |
|  | 15.0 | 29 | 71 |
|  | 15.5 | 0 | 100 |
|  | 18.0 | 0 | 100 |
|  | 18.5 | 49 | 51 |
|  | 20.0 | 49 | 51 |

Collected the component at retention time of 14.5 min to obtain (Z)-isomer (Compound 2-1); and retention time of 16.0 min to obtain (E)-isomer (Compound 2-2).

(Z)-Isomer Hydrochloride

The obtained (Z)-isomer was dissolved in ethyl acetate, and concentrated hydrochloric acid was added dropwise until pH=1.0 to precipitate solid, a little diethyl ether was added dropwise, and the mixture was stirred overnight at room temperature, filtered and the residue was dried under reduced pressure to obtain hydrochloride.

$^1$H NMR [(CD$_3$)$_2$SO]: δ 11.41 (s, 1H), 10.30 (s, 1H), 8.99 (s, 1H), 8.88 (s, 1H), 8.04 (dd, 1H), 7.77-7.70 (m, 1H), 7.58 (s, 1H), 7.56 (dd, 1H), 6.47 (td, 1H), 4.03 (s, 3H), 3.99 (br, 2H), 2.79 (s, 6H).

(E)-Isomer $^1$H NMR (300 MHz, DMSO) δ 10.26 (s, 1H), 10.02 (s, 1H), 8.92 (d, J=2.7 Hz, 1H), 8.88 (d, J=1.5 Hz, 1H), 8.01 (dd, $J_1$=6.6 Hz, $J_2$=2.1 Hz, 1H), 7.70-7.67 (m, 1H), 7.56 (t, J=9.0 Hz, 1H), 7.42 (d, J=2.7 Hz, 1H), 6.34 (dt, $J_1$=33.6 Hz, $J_2$=7.5 Hz, 1H), 4.06 (s, 3H), 4.04 (brs, 2H), 2.33 (s, 6H).

Example 3

The following compounds which were the mixture of cis- and trans-isomer were prepared according to the method in Example 1 with different starting materials.

Compound 3-1: N-(4-((3-chloro-4-fluorophenyl)amino)-7-(2-methoxyethoxy)quinazolin-6-yl)-4-(dimethylamino)-2-fluorobut-2-enamide

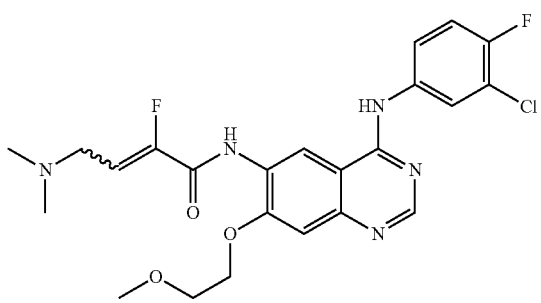 [SMILES: COCCOc1cc2ncnc(Nc3ccc(F)c(Cl)c3)c2cc1NC(=O)C(F)=CCN(C)C]

Starting material: N$^4$-(3-chloro-4-fluorophenyl)-7-(2-methoxyethoxy)quinazoline-4,6-diamine was prepared according to the method in WO2008/33747; other starting materials were prepared as example 1.

MS (ESI$^+$): m/z=492, 493, 494 [M+H]$^+$;

Rf value: 0.38 (silica gel, ethyl acetate/methanol=9:1).

Compound 3-2: N-(4-((3-chloro-4-fluorophenyl)amino)-7-ethoxyquinazolin-6-yl)-4-(dimethylamino)-2-fluorobut-2-enamide

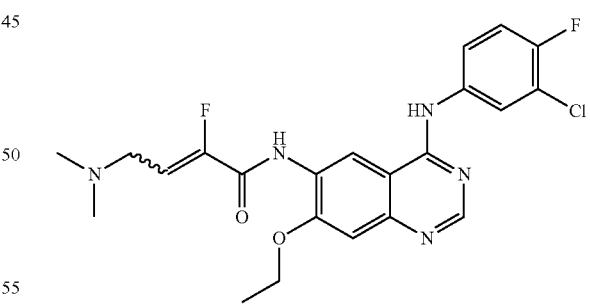

Starting material: N$^4$-(3-chloro-4-fluorophenyl)-7-ethoxyquinazoline-4,6-diamine was prepared according to the same method of the preparation of N$^4$-(3-chloro-4-fluorophenyl)-7-(2-methoxy)ethoxyquinazoline-4,6-diamine in WO2008/33747, but starting material was 4-chloro-7-ethoxy-6-nitro-quinazoline (*Bioorg. Med. Chem,* 2007, 15, 3635-3648); other materials were prepared as example 1.

MS (ESI$^+$): m/z=452, 463, 464 [M+H]$^+$;

Rf value: 0.32 (silica gel, ethyl acetate/methanol=5:1).

Compound 3-3: N-(4-((3-chloro-4-fluorophenyl)amino)-7-(2-methoxyethoxy)quinazolin-6-yl)-2-fluoro-4-morpholinobut-2-enamide

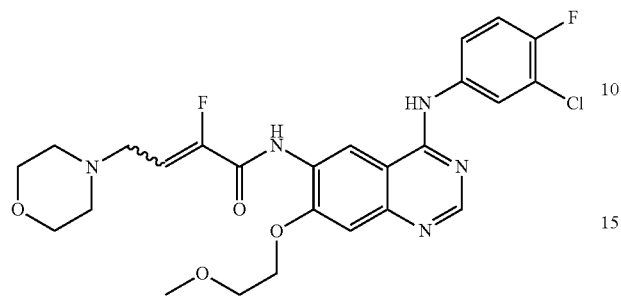

Starting material: N⁴-(3-chloro-4-fluorophenyl)-7-(2-methoxyethoxy)quinazoline-4,6-diamine was prepared according to the method in WO2008/33747; 2-(morpholin-4-yl)acetaldehyde was prepared according to the method in *Bioorg. Med. Chem*, 2007, 15, 6425-6442; other starting materials were prepared as example 1.

MS (ESI⁺): m/z=534, 535, 536 [M+H]⁺

Rf values: 0.76 (silica gel, ethyl acetate/methanol=5:1; two isomers were not separated);

0.60, 0.66 (silica gel, dichloromethane/methanol=10:1; two isomers were separated)

Compound 3-4: (R)—N-(4-((3-chloro-4-fluorophenyl)amino)-7-((tetrahydrofuran-3-yl)oxy)quinazolin-6-yl)-4-(dimethylamino)-2-fluorobut-2-enamide

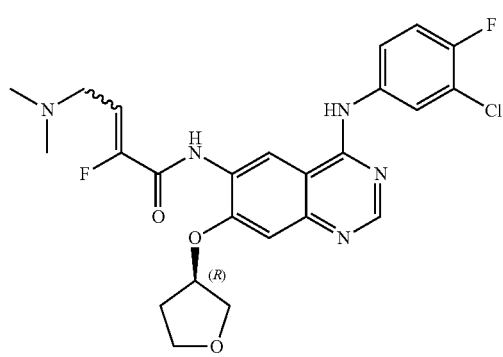

Material:

(R)—N⁴-(3-chloro-4-fluorophenyl)-7-((tetrahydrofuran-3-yl)oxy)quinazoline-4,6-diamine was prepared according to the method in WO2007/85638; other starting materials were prepared as example 1.

MS (ESI⁺): m/z=504, 505, 506 [M+H]⁺;

Rf values: 0.27 (silica gel, ethyl acetate/methanol=5:1; two isomers were not separated);

0.49, 0.54 (silica gel, dichloromethane/methanol=10:1; two isomers were separated).

Compound 3-5: N-(4-((3-chloro-4-fluorophenyl)amino)-7-((tetrahydro-2H-pyran-4-yl)methoxy)quinazolin-6-yl)-4-(dimethylamino)-2-fluorobut-2-enamide

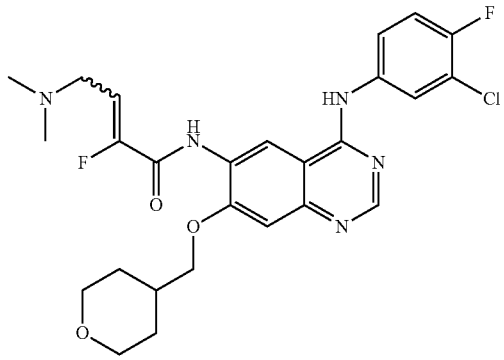 [SMILES: CN(C)CC=C(F)C(=O)Nc1cc2c(Nc3ccc(F)c(Cl)c3)ncnc2cc1OCC1CCOCC1]

Starting material: N⁴-(3-chloro-4-fluorophenyl)-7-((tetrahydro-2H-pyran-4-yl)methoxy)quinazoline-4,6-diamine was prepared according to the method in US2002/173509; other starting materials were prepared as example 1.

MS (ESI⁺): m/z=532, 533, 534 [M+H]⁺

Rf value: 0.42 (silica gel, ethyl acetate/methanol=5:1)

Compound 3-6: N-(4-((3-chloro-4-fluorophenyl)amino)-7-methoxyquinazolin-6-yl)-4-(diethylamino)-2-fluorobut-2-enamide

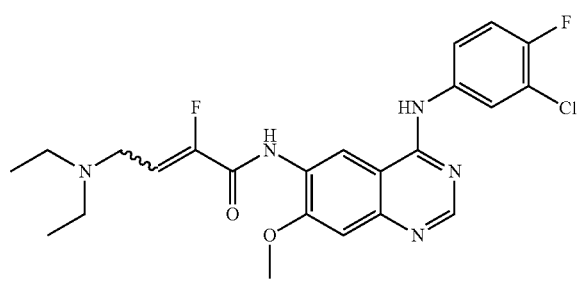 [SMILES: CCN(CC)CC=C(F)C(=O)Nc1cc2c(Nc3ccc(F)c(Cl)c3)ncnc2cc1OC]

Starting material: 2-(diethylamino)-acetaldehyde sulfite was prepared according to the same method of preparation of 2-(dimethylamino)-acetaldehyde sulfite in WO2007/85638, other starting materials were prepared as example 1.

MS (ESI⁺): m/z=476, 477, 478 [M+H]⁺

Rf value: 0.31 (silica gel, ethyl acetate/methanol=5:1)

Compound 3-7: N-(4-((3-chloro-4-fluorophenyl)amino)-7-(2-methoxyethoxy)quinazolin-6-yl)-2-fluoro-4-(4-methylpiperazin-1-yl)but-2-enamide

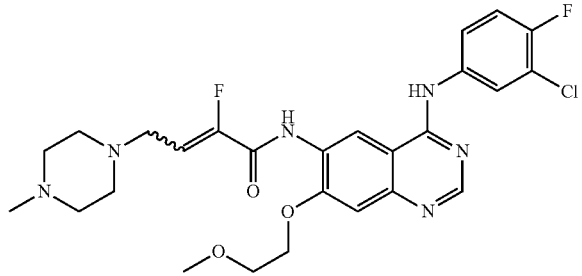 [SMILES: COCCOc1cc2ncnc(Nc3ccc(F)c(Cl)c3)c2cc1NC(=O)C(F)=CCN1CCN(C)CC1]

Starting material: N⁴-(3-chloro-4-fluorophenyl)-7-(2-methoxyethoxy)quinazoline-4,6-diamine was prepared according to the method in WO2008/33747; starting material: 2-(4-methylpiperazin-1-yl)acetaldehyde was prepared according to the same method of preparation of 2-(morpholin-4-yl)acetaldehyde in *Bioorganic. and Medicinal. Chemistry.* 2007, 15, 6425-6442; other starting materials were prepared as example 1.

MS (ESI⁺): m/z=547, 548, 549 [M+H]⁺;

Rf value: 0.35, 0.39 (silica gel, dichloromethane/methanol=10:1; two isomers were separated).

Compound 3-8: N-(4-((3-chloro-4-fluorophenyl)amino)-7-methoxyquinazolin-6-yl)-2-fluoro-4-((2-methoxyethyl)(methyl)amino)but-2-enamide

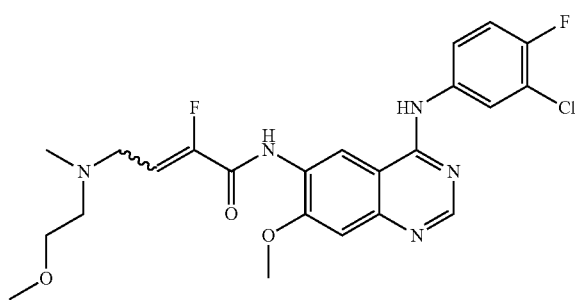 [SMILES: COCCN(C)CC=C(F)C(=O)Nc1cc2c(Nc3ccc(F)c(Cl)c3)ncnc2cc1OC]

Starting material 2-((2-methoxyethyl)(methyl)amino)acetaldehyde was prepared according to the method of preparation of 2-(morpholin-4-yl)acetaldehyde in *Bioorg. Med. Chem.*, 2007, 15, 6425-6442; other starting materials were prepared as example 1.

MS (ESI⁺): m/z=492, 493, 494 [M+H]⁺;

Rf value: 0.48 (silica gel, ethyl acetate/methanol=5:1).

Compound 3-9: N-(4-((3-chloro-4-fluorophenyl)amino)-7-methoxyquinazolin-6-yl)-2-fluoro-4-(4-methylpiperazin-1-yl)but-2-enamide

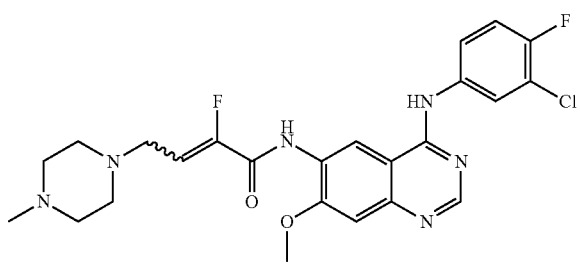 [SMILES: COc1cc2ncnc(Nc3ccc(F)c(Cl)c3)c2cc1NC(=O)C(F)=CCN1CCN(C)CC1]

Starting material: 2-(4-methyl-piperazin-1-yl)acetaldehyde was prepared according to the same method of the preparation of 2-(morpholin-4-yl)-acetaldehyde in *Bioorg. Med. Chem.* 2007, 15, 6425-6442, other starting materials were prepared as example 1.

MS (ESI⁺): m/z=503, 504, 505 [M+H]⁺

Rf value: 0.32, 0.36 (silica gel, dichloromethane/methanol=10:1; two isomers were separated)

Compound 3-10: N-(4-((3-chloro-4-fluorophenyl)amino)-7-methoxyquinazolin-6-yl)-2-fluoro-4-(methyl(tetrahydrofuran-3-yl)amino)but-2-enamide

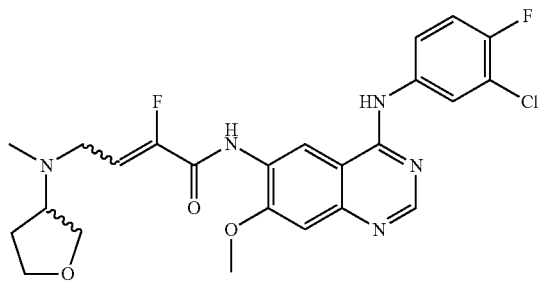 [SMILES: COc1cc2ncnc(Nc3ccc(F)c(Cl)c3)c2cc1NC(=O)C(F)=CCN(C)C1CCOC1]

Starting material: 2-(methyl-(tetrahydrofuran-3-yl)amino)acetaldehyde was prepared according to the same method of the preparation of 2-(morpholin-4-yl)-acetaldehyde in *Bioorg. Med. Chem.* 2007, 15, 6425-6442. Other starting material were prepared as in Example 1.

MS (ESI⁺): m/z=504, 505, 506 [M+H]⁺;

Rf value: 0.65 (silica gel, ethyl acetate/methanol=5:1).

Compound 3-11: N-(4-((3-chloro-4-fluorophenyl)amino)-7-methoxyquinazolin-6-yl)-4-(2-(dimethylamino)ethoxy)-2-fluorobut-2-enamide

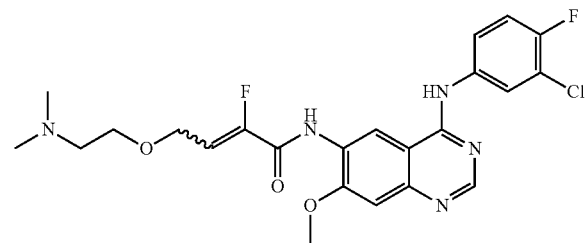 [SMILES: COc1cc2ncnc(Nc3ccc(F)c(Cl)c3)c2cc1NC(=O)C(F)=CCOCCN(C)C]

Starting material: 2-(2-(dimethylamino)ethoxy)acetaldehyde was prepared according to the same method of 2-(morpholin-4-yl)-acetaldehyde in *Bioorg. Med. Chem.* 2007, 15, 6425-6442; other starting materials were prepared as example 1.

MS (ESI⁺): m/z=492, 493, 494 [M+H]⁺;

Rf value: 0.36 (silica gel, ethyl acetate/methanol=5:1).

Compound 3-12: (S)—N-(4-((3-chloro-4-fluorophenyl)amino)-7-methoxyquinazolin-6-yl)-2-fluoro-3-(1-methylpyrrolidin-2-yl)acrylamide

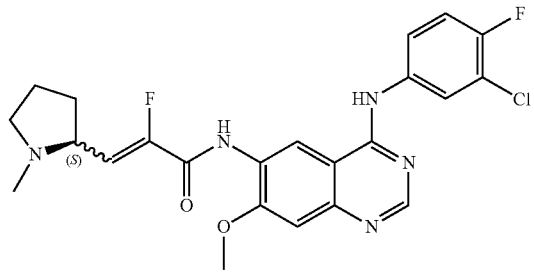

Starting material: (S)—N-methylpyrrolidin-2-carbaldehyde was prepared according to the method in *Chemistry—A European Journal,* 1996, 2, 894-900; other starting materials were prepared as example 1.

MS (ESI⁺): m/z=474, 475, 476 [M+H]⁺

Rf value: 0.28 (silica gel, ethyl acetate/methanol=5:1)

Compound 3-13: N-(4-((3-chloro-4-(pyridin-2-yl-methoxy)phenyl)amino)-7-methoxyquinazolin-6-yl)-4-(dimethylamino)-2-fluorobut-2-enamide

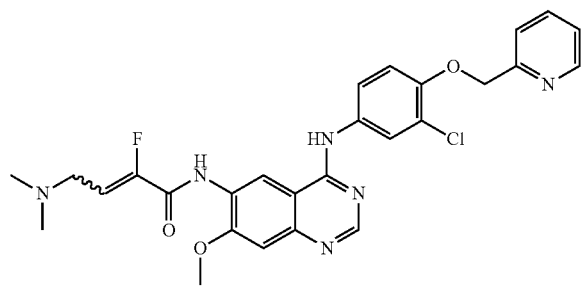 [SMILES: COc1cc2ncnc(Nc3ccc(OCc4ccccn4)c(Cl)c3)c2cc1NC(=O)C(F)=CCN(C)C]

Starting material: N⁴-(3-chloro-4-(pyridin-2-ylmethoxy) phenyl)-7-methoxyquinazoline-4,6-diamine was prepared according to the method in WO2006/71017; other starting materials were prepared as example 1.
MS (ESI⁺): m/z=537, 538, 539 [M+H]⁺;
Rf value: 0.26 (silica gel, ethyl acetate/methanol=5:1).

Compound 3-14: N-(4-((3-chloro-4-((3-fluoroben-zyl)oxy)phenyl)amino)-7-methoxy-quinazolin-6-yl)-4-(dimethylamino)-2-fluorobut-2-enamide

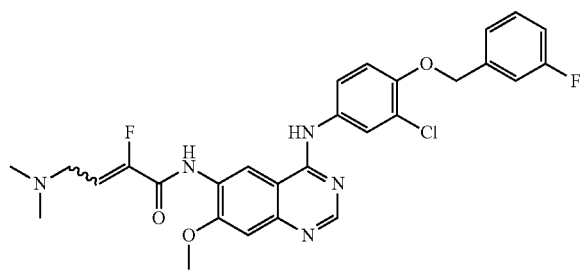 [SMILES: COc1cc2ncnc(Nc3ccc(OCc4cccc(F)c4)c(Cl)c3)c2cc1NC(=O)C(F)=CCN(C)C]

Starting material: N⁴-(3-chloro-4-((3-fluorobenzyl)oxy) phenyl)-7-methoxyquinazoline-4,6-diamine was prepared according to the method in US2008/300248; other starting materials were prepared as example 1.
MS (ESP): m/z=554, 555, 556 [M+H]⁺;
Rf value: 0.31 (silica gel, ethyl acetate/methanol=5:1).

Compound 3-15: 4-(dimethylamino)-2-fluoro-N-(4-((1-(3-fluorobenzyl)-1H-indazol-5-yl)amino)-7-methoxyquinazolin-6-yl)but-2-enamide

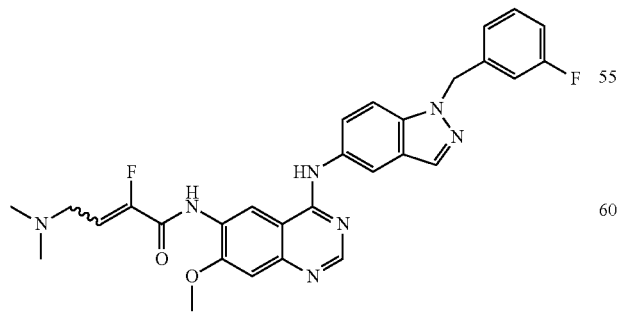

Starting material: N⁴-(1-(3-fluorobenzyl)-1H-indazol-5-yl)-7-methoxyquinazoline-4,6-diamine was prepared according to the method in WO2006/71017; other starting materials were prepared as example 1.
MS (ESI⁺): m/z=544, 545 [M+H]⁺;
Rf value: 0.25 (silica gel, ethyl acetate/methanol=5:1; two isomers were not separated); 0.47, 0.52 (silica gel, dichloromethane/methanol=10:1; two isomers were separated).

Compound 3-16: 4-(dimethylamino)-N-(4-((3-ethynylphenyl)amino)-7-methoxyquinazolin-6-yl)-2-fluorobut-2-enamide

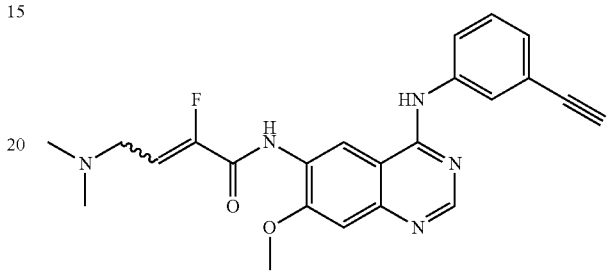

Starting material: N⁴-(3-ethynylphenyl)-7-methoxyquinazoline-4,6-diamine was prepared according to the method in WO2008/33747; other starting materials were prepared as example 1.
MS (ESI⁺): m/z=420, 421 [M+H]⁺;
Rf value: 0.32 (silica gel, ethyl acetate/methanol=5:1).

Compound 3-17: N-(4-((2,4-dichloro-5-methoxyphenyl)amino)-7-methoxyquinazolin-6-yl)-4-(dimethylamino)-2-fluorobut-2-enamide

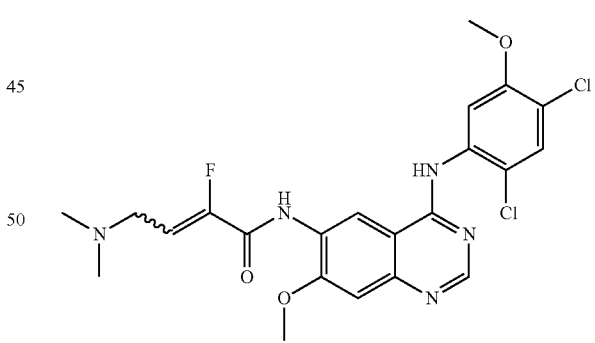

Starting material: N⁴-(2,4-dichloro-5-methoxyphenyl)-7-methoxyquinazoline-4,6-diamine was prepared according to the same method of preparation of N⁴-(3-chloro-4-fluorophenyl)-7-(2-methoxy)ethoxyquinazoline-4,6-diamine in WO2008/33747, but the starting material was 4-chloro-7-methoxy-6-nitro-quinazoline and 2,4-dichloro-5-methoxyaniline; other starting materials were prepared as example 1.
MS (ESI⁺): m/z=494, 495, 496 [M+H]⁺;
Rf value: 0.34 (silica gel, ethyl acetate/methanol=5:1).

Compound 3-18: N-(4-((5-chlorobenzo[d][1,3]di-oxol-4-yl)amino)-7-methoxyquinazolin-6-yl)-4-(dimethylamino)-2-fluorobut-2-enamide

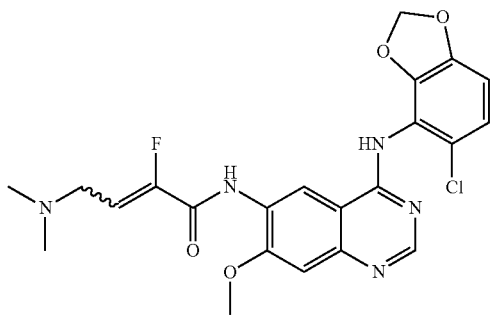 [SMILES: COc1cc2ncnc(Nc3c(Cl)ccc4c3OCO4)c2cc1NC(=O)C(F)=CCN(C)C]

Starting material: N⁴-(5-chlorobenzo[d][1,3]dioxol-4-yl)-7-methoxyquinazoline-4,6-diamine was prepared according to the same method of preparation of N⁴-(3-chloro-4-fluorophenyl)-7-(2-methoxy)ethoxyquinazoline-4,6-diamine in WO2008/33747, but the starting material were 4-chloro-7-methoxy-6-nitroquinazoline and 5-chlorobenzo[d][1,3]dioxolan-4-amine; other starting materials were prepared as example 1.

MS (ESI⁺): m/z=474, 475, 476 [M+H]⁺;
Rf value: 0.36 (silica gel, ethyl acetate/methanol=5:1).

Compound 3-19: N-(4-((4-chloro-3-(trifluoromethyl)phenyl)amino)-7-methoxyquinazolin-6-yl)-4-(dimethylamino)-2-fluorobut-2-enamide

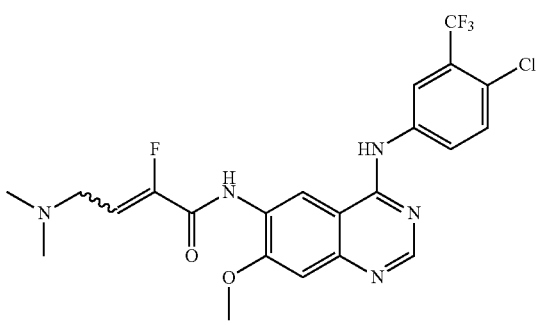 [SMILES: COc1cc2ncnc(Nc3ccc(Cl)c(C(F)(F)F)c3)c2cc1NC(=O)C(F)=CCN(C)C]

Starting material: N⁴-(4-chloro-3-(trifluoromethyl)phenyl)-7-methoxyquinazoline-4,6-diamine was prepared according to the same method of preparation of N⁴-(3-chloro-4-fluorophenyl)-7-(2-methoxy)ethoxyquinazoline-4,6-diamine in WO2008/33747, but the starting materials were 4-chloro-7-methoxy-6-nitro-quinazoline and 4-chloro-3-(trifluoromethyl) aniline; other starting materials were prepared as example 1.

MS (ESI⁺): m/z=498, 499, 500 [M+H]⁺;
Rf value: 0.33 (silica gel, ethyl acetate/methanol=5:1).

Compound 3-20: N-(4-((3-bromophenyl)amino)-7-methoxyquinazolin-6-yl)-4-(dimethylamino)-2-fluorobut-2-enamide

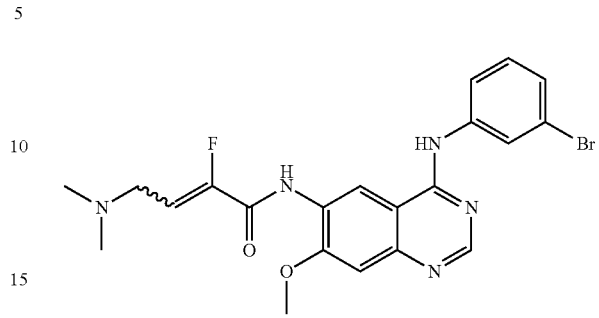

Starting material: N⁴-(3-bromophenyl)-7-methoxyquinazoline-4,6-diamine was prepared according to the method in *Journal of Medicinal Chemistry*, 1996, 39, 267-276; other starting materials were prepared as example 1.

MS (ESI⁺): m/z=474, 476 [M+H]⁺;
Rf value: 0.31 (silica gel, ethyl acetate/methanol=5:1).

Compound 3-21: N-(4-((3-chloro-2-fluorophenyl)amino)-7-methoxyquinazolin-6-yl)-4-(dimethylamino)-2-fluorobut-2-enamide

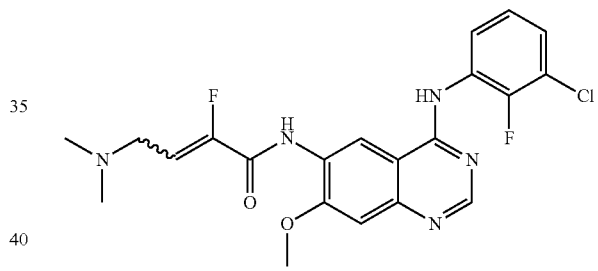

Starting material: N⁴-(3-chloro-2-fluorophenyl)-7-methoxyquinazoline-4,6-diamine was prepared according to the method in *Journal of Medicinal Chemistry*, 2009, 52, 6880-6888; other starting materials were prepared as example 1.

MS (ESI⁺): m/z=448, 449, 450 [M+H]⁺;
Rf value: 0.32 (silica gel, ethyl acetate/methanol=5:1).

Compound 3-22: N-(4-((4-bromo-2-fluorophenyl)amino)-7-methoxyquinazolin-6-yl)-4-(dimethylamino)-2-fluorobut-2-enamide

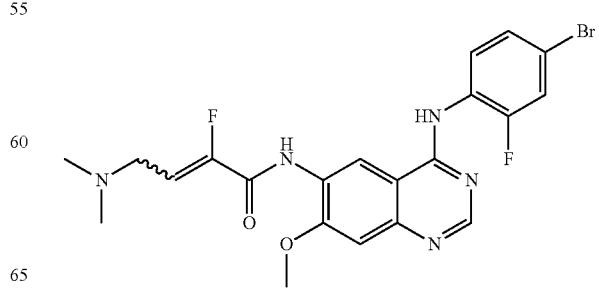

Starting material: $N^4$-(4-bromo-2-fluorophenyl)-7-methoxyquinazoline-4,6-diamine was prepared according to the same method of preparation of $N^4$-(3-chloro-4-fluorophenyl)-7-(2-methoxy)ethoxyquinazoline-4,6-diamine in WO2008/33747, but the starting materials were 4-chloro-7-methoxy-6-nitro-quinazoline and 4-bromo-2-fluoro-aniline; other starting materials were prepared as example 1.

MS (ESI⁺): m/z=492, 494 [M+H]⁺;

Rf value: 0.33 (silica gel, ethyl acetate/methanol=5:1).

Compound 3-23: N-(4-((3-chloro-2,4-difluorophenyl)amino)-7-methoxyquinazolin-6-yl)-4-(dimethylamino)-2-fluorobut-2-enamide

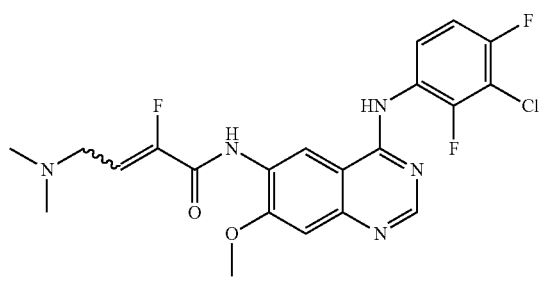

Starting material: $N^4$-(3-chloro-2,4-difluorophenyl)-7-methoxyquinazoline-4,6-diamine was prepared according to the same method of preparation of $N^4$-(3-chloro-4-fluorophenyl)-7-(2-methoxy)ethoxyquinazoline-4,6-diamine in WO2008/33747, but the starting materials were 4-chloro-7-methoxy-6-nitro-quinazoline and 3-chloro-2,4-difluoro-aniline; other starting materials were prepared as example 1.

MS (ESI⁺): m/z=466, 467, 468 [M+H]⁺;

Rf value: 0.35 (silica gel, ethyl acetate/methanol=5:1).

Compound 3-24: N-(4-((3,4-dichloro-2-fluorophenyl)amino)-7-methoxyquinazolin-6-yl)-4-(dimethylamino)-2-fluorobut-2-enamide

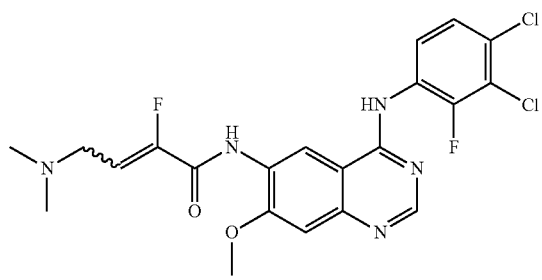 [SMILES: COc1cc2ncnc(Nc3ccc(F)c(Cl)c3F)c2cc1NC(=O)C(F)=CCN(C)C]

Starting material: $N^4$-(3,4-dichloro-2-fluorophenyl)-7-methoxyquinazoline-4,6-diamine was prepared according to the same method of preparation of $N^4$-(3-chloro-4-fluorophenyl)-7-(2-methoxy)ethoxyquinazoline-4,6-diamine in WO2008/33747, but the starting materials were 4-chloro-7-methoxy-6-nitro-quinazoline and 3,4-dichloro-2-fluoro-aniline; other starting materials were prepared as example 1.

MS (ESI⁺): m/z=482, 483, 484 [M+H]⁺;

Rf value: 0.34 (silica gel, ethyl acetate/methanol=5:1).

Compound 3-25: N-(4-((4-bromo-3-chloro-2-fluorophenyl)amino)-7-methoxyquinazolin-6-yl)-4-(dimethylamino)-2-fluorobut-2-enamide

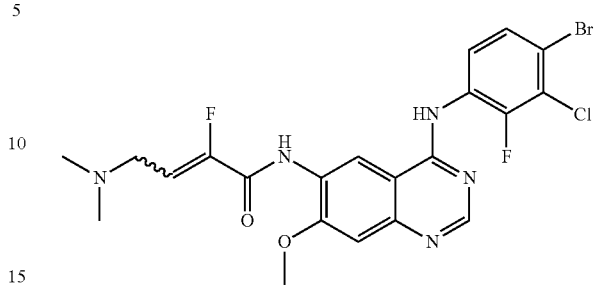

Starting material: $N^4$-(4-bromo-3-chloro-2-fluorophenyl)-7-methoxyquinazoline-4,6-diamine was prepared according to the same method of preparation of $N^4$-(3-chloro-4-fluorophenyl)-7-(2-methoxy)ethoxyquinazoline-4,6-diamine in WO2008/33747, but the starting materials were 4-chloro-7-methoxy-6-nitro-quinazoline and 4-bromo-3-chloro-2-fluoro-aniline; other starting materials were prepared as example 1.

MS (ESI⁺): m/z=526, 528 [M+H]±;

Rf value: 0.35 (silica gel, ethyl acetate/methanol=5:1).

Example 4

According to the method described in example 2, use the same equipment and conditions of HPLC to separate the compounds obtained in examples 3-13 (mixtures of cis and trans isomers), the following compounds were obtained:

Compounds 4-1 and 4-2: (Z)—N-(4-((3-chloro-4-(pyridin-2-yl methoxy)phenyl)amino)-7-methoxyquinazolin-6-yl)-4-(dimethylamino)-2-fluorobut-2-enamide, and (E)-N-(4-((3-chloro-4-(pyridin-2-yl methoxy)phenyl)amino)-7-methoxyquinazolin-6-yl)-4-(dimethylamino)-2-fluorobut-2-enamide

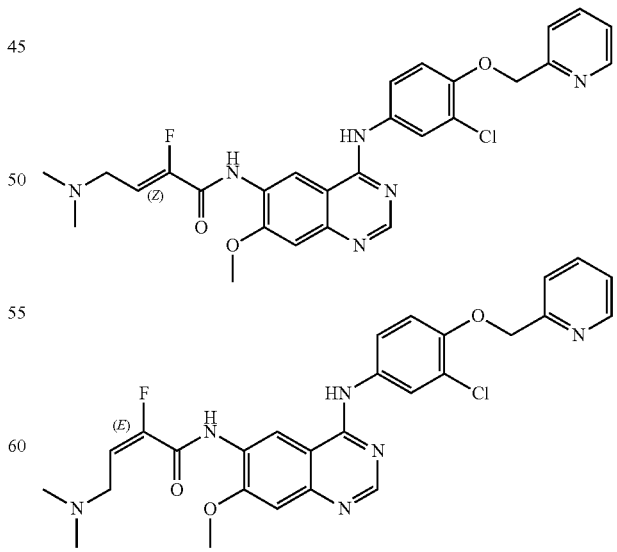

(Z)-isomer (compound 4-1): the retention time was 12.0 min.

$^1$H NMR [(CD$_3$)$_2$SO]: δ 10.73 (s, 1H), 9.68 (s, 1H), 8.53 (s, 1H), 8.57 (d, 1H), 8.51 (s, 1H), 7.92 (s, 1H), 7.80 (dd, 1H), 7.65-7.53 (m, 2H), 7.36 (dd, 1H), 7.24 (dd, 1H), 6.12 (td, 1H), 5.26 (s, 2H), 4.01 (s, 3H), 3.66 (d, 2H), 2.24 (s, 6H).

(E)-isomer (compound 4-2): the retention time was 13.2 min.

$^1$H NMR [(CD$_3$)$_2$SO]: δ 10.89 (s, 1H), 9.73 (s, 1H), 8.78 (s, 1H), 8.60 (d, 1H), 8.50 (s, 1H), 7.99 (s, 1H), 7.88 (dd, 1H), 7.70-7.59 (m, 2H), 7.37 (dd, 1H), 7.29 (dd, 1H), 6.15 (td, 1H), 5.28 (s, 2H), 4.00 (s, 3H), 3.68 (d, 2H), 2.23 (s, 6H).

Example 5

The preparation of N-(4-((3-chloro-4-fluorophenyl)amino)-7-(3-morpholinopropoxy)quinazolin-6-yl)-2-fluoroacrylamide

Step 1: The preparation of N-(3-chloro-4-fluorophenyl)-7-(3-morpholinopropoxy)-6-nitroquinazolin-4-amine Starting material: N-(3-chloro-4-fluorophenyl)-7-fluoro-6-nitroquinazolin-4-amine was prepared according to the method in *J. Med Chem* 2009, 52, 6880-6888.

6-nitro-4-(3-chloro-4-fluorophenylamino)-7-fluoroquinazoline (1 eq.) and morpholine-propanol (1.5 eq.) were dissolved in DMSO (10 ml), the solution was stirred for 5 mins with a water bath. A solution of potassium tert-butoxide (3.0 eq.) in DMSO (5 ml) was added slowly to the solution mentioned-above in drops, the mixture was stirred at room temperature for further 30 mins. After the reaction finished, the mixture was diluted with 100 ml water and pH was adjusted to neutral with concentrated hydrochloric acid, then

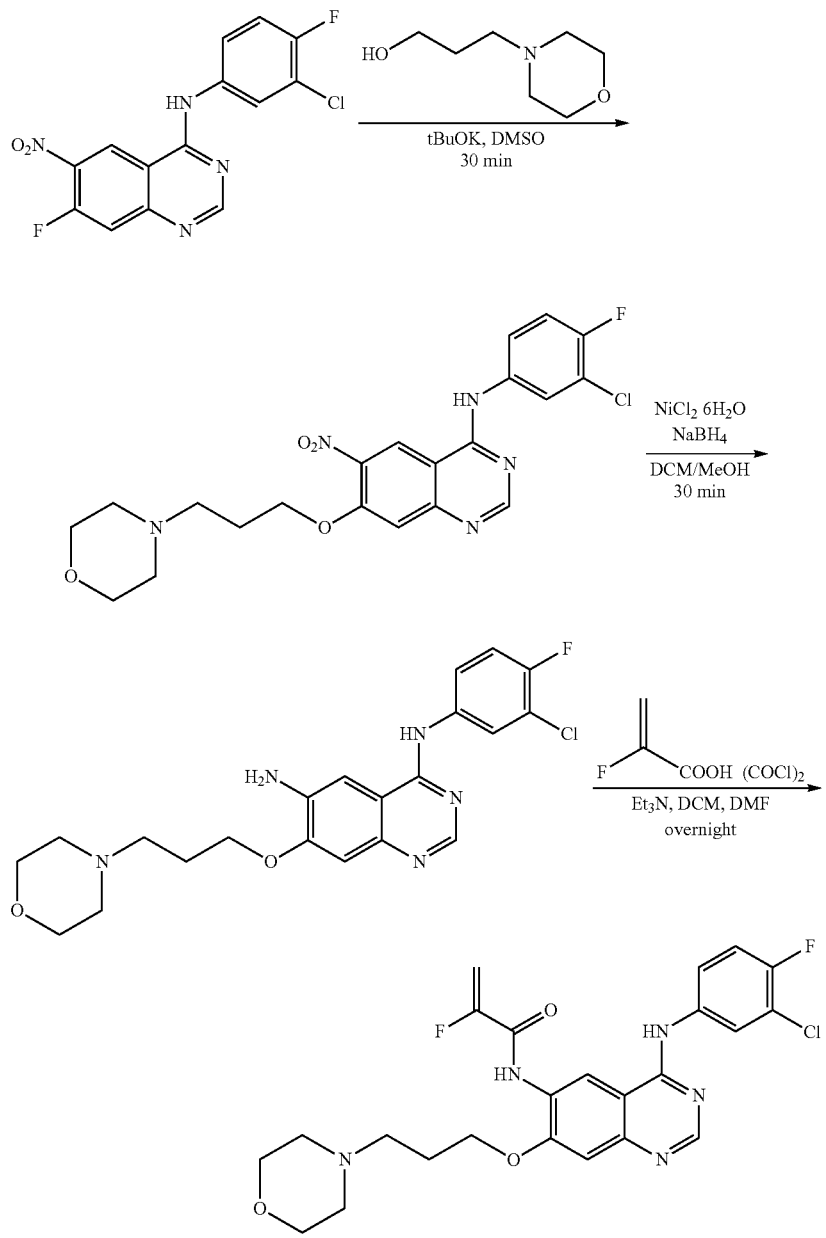

stirred for 30 mins, large amount of yellow solid was precipitated, then filtering, the filter cake was washed with water twice and dried to give yellow solid of N-(3-chloro-4-fluorophenyl)-7-(3-morpholinopropoxy)-6-nitroquinazolin-4-amine (yield 90%).

$^1$H NMR (500 MHz, DMSO) δ 10.15 (s, 1H), 9.21 (s, 1H), 8.67 (s, 1H), 8.16 (dd, J$_1$=7.0 Hz, J$_2$=3.0 Hz, 1H), 7.82-7.78 (m, 1H), 7.49-7.45 (m, 2H), 4.34 (t, J=6.5 Hz, 2H), 3.58 (t, J=4.0 Hz, 4H), 2.46 (t, J=6.5 Hz, 2H), 2.38 (brs, 4H), 1.97-1.92 (m, 2H). HRMS (ESI): m/z calcd for $(C_{21}H_{21}ClFN_5O_4$+H$)^+$: 462.1344. found: 462.1344.

Step 2: The preparation of N-(3-chloro-4-fluorophenyl)-7-(3-morpholinopropoxy)-quinazolin-4,6-diamine N-(3-chloro-4-fluorophenyl)-7-(3-morpholinopropoxy)-6-nitroquinazolin-4-amine (1.0 eq.) obtained in previous step and NiCl$_2$ 6H$_2$O (2.0 eq.) were dissolved in DCM/MeOH (32 ml:8 ml), the mixture was stirred at 0° C. for 5 min, and NaBH$_4$ (4.0 eq.) was added in batches, then ice bath was removed and the mixture was recovered to room temperature naturally, stirred for further 30 mins. After the reaction finished, the mixture was concentrated to dryness under reduced pressure and gave a crude product which was purified by column chromatography (mobile phase 10:1 DCM/MeOH) to give a light yellow solid of N-(3-chloro-4-fluorophenyl)-7-(3-morpholinopropoxy)-quinazolin-4,6-diamine. (50% yield).

$^1$H NMR (500 MHz, DMSO) δ 9.39 (s, 1H), 8.37 (s, 1H), 8.20 (d, J=4.5 Hz, 1H), 7.81 (d, J=8.5 Hz, 1H), 7.41-7.38 (m, 2H), 7.08 (s, 1H), 5.35 (s, 2H), 4.20 (t, J=5.5 Hz, 2H), 3.59 (t, J=4.5 Hz, 4H), 3.18 (d, J=5.0 Hz, 2H), 2.40 (s, 4H), 2.01-1.96 (m, 2H). HRMS (ESI): m/z calcd for $(C_{21}H_{23}ClFN_5O_2$+H$)^+$: 432.1603. found: 432.1613.

Step 3: the preparation of N-(4-((3-chloro-4-fluorophenyl)amino)-7-(3-morpholinopropoxy)quinazolin-6-yl)-2-fluoroacrylamide To a solution of 2-fluoro-acrylic acid (2.0 eq.) in DCM (10 ml) were added 3 drops of DMF, under an ice bath, oxalyl chloride (1.8 eq.) was added dropwise and the mixture reacted under the ice bath for 30 mins, then the ice bath was removed, after the mixture was recovered to room temperature, reacted for 2 hours. A solution of N-(3-chloro-4-fluorophenyl)-7-(3-morpholinopropoxy)-quinazolin-4,6-diamine (1.0 eq.) that was obtained in previous step in DCM (20 ml) stirred at 0° C. for 5 mins, and was added into the acyl chloride solution, and then Et$_3$N (4.0 eq.) was added, the mixture reacted for 30 mins under an ice bath, then the ice bath was removed, after the mixture was recovered to room temperature, stirred overnight. After the reaction finished, the mixture was concentrated to dryness under reduced pressure, and the crude product was purified by column chromatography (mobile phase 10:1 DCM/MeOH) to give a pale yellow solid of N-(4-((3-chloro-4-fluorophenyl)amino)-7-(3-morpholinopropoxy)quinazolin-6-yl)-2-fluoroacrylamide (50% yield).

$^1$H NMR (500 MHz, DMSO): δ 9.83 (s, 1H), 9.76 (d, J=1.5 Hz, 1H), 8.72 (s, 1H), 8.58 (s, 1H), 8.17 (dd, J=6.9, 2.6 Hz, 1H), 7.82 (m, 1H), 7.43 (t, J=9.1 Hz, 1H), 7.31 (s, 1H), 5.77 (dd, J=48.1, 3.7 Hz, 1H), 5.52 (dd, J=15.7, 3.7 Hz, 1H), 4.25 (t, J=6.0 Hz, 2H), 3.58 (t, J=4.4 Hz, 4H), 2.47 (t, J=7.1 Hz, 2H), 2.37 (s, 4H), 1.99-1.92 (m, 2H). HRMS (ESI): m/z calcd for $(C_{24}H_{24}ClF_2N_5O_3$+H$)^+$: 504.1614. found: 504.1625.

Example 6

The preparation of N-(4-((3-chloro-2,4-difluorophenyl)amino)-7-((1-methylpiperidin-4-yl)methoxy)quinazolin-6-yl)-2-fluoroacrylamide

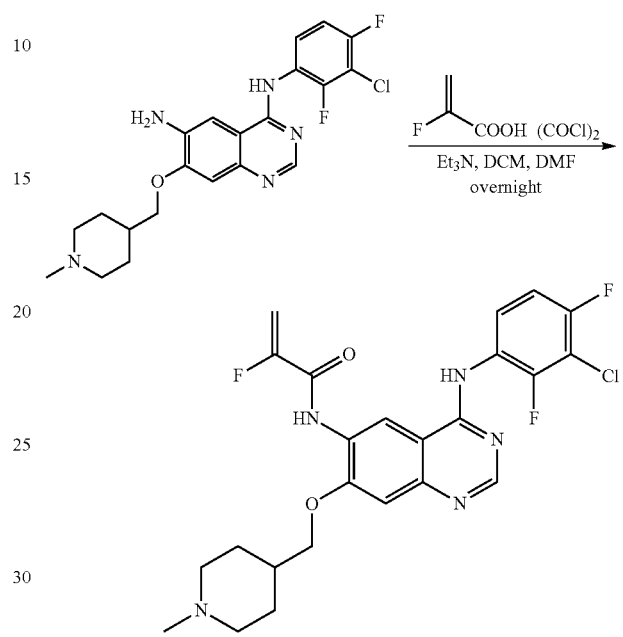

The preparation was the same with step 3 of example 5 and a yellow solid of N-(4-((3-chloro-2,4-difluorophenyl)amino)-7-((1-methylpiperidin-4-yl)methoxy)quinazolin-6-yl)-2-fluoroacrylamide was given. (50% yield).

$^1$H NMR (500 MHz, DMSO) δ 9.92 (s, 1H), 9.66 (s, 1H), 8.72 (s, 1H), 8.44 (s, 1H), 7.56-7.52 (m, 1H), 7.38 (t, J=8.5 Hz, 1H), 7.32 (s, 1H), 5.76 (dd, J=48.3, 3.7 Hz, 1H), 5.52 (dd, J=15.7, 3.7 Hz, 1H), 4.09 (d, J=5.9 Hz, 2H), 2.83 (d, J=11.1 Hz, 2H), 2.19 (s, 1.92 (t, J=11.2 Hz, 2H), 1.78-1.76 (d, 3H), 1.42-1.34 (m, 2H). HRMS (ESI): m/z calcd for $(C_{24}H_{23}ClF_3N_5O_2$+H$)^+$: 506.1570. found: 506.1564.

Example 7

The preparation of N-(4-((3-chloro-4-fluorophenyl)amino)-7-methoxyquinazolin-6-yl)-2-fluoro-4-(piperidin-1-yl)but-2-enamide

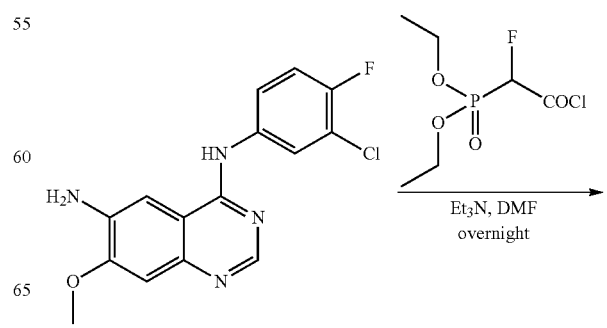

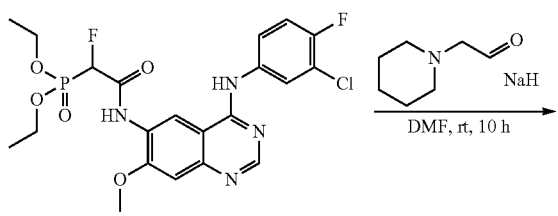

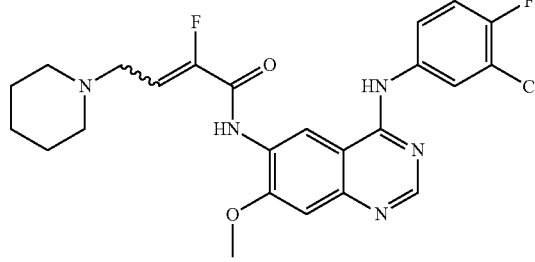

Step 1 the preparation of diethyl (2-((4-((3-chloro-4-fluorophenyl)amino)-7-methoxyquinazolin-6-yl)amino)-1-fluoro-2-oxoethyl)phosphonate Starting materials: 6-amino-4-(3-chloro-4-fluorophenyl)-7-methoxy-quinazoline was prepared according to the method in *J. Med Chem* 2009, 52, 6880-6888.

Starting material: diethyl (2-chloro-1-fluoro-2-oxoethyl) phosphonate was prepared according to the method in *Heterocycles*, 2004, 63, 699-706.

The procedure was the same with step 1 of example 1 and a pale yellow solid of diethyl (2-((4-((3-chloro-4-fluorophenyl)amino)-7-methoxyquinazolin-6-yl)amino)-1-fluoro-2-oxoethyl)phosphonate was given. (56% yield)

$^1$H NMR (500 MHz, DMSO) δ 9.94 (s, 1H), 9.64 (s, 1H), 8.89 (s, 1H), 8.55 (s, 1H), 8.09 (dd, $J_1$=6.5 Hz, $J_2$=2.5 Hz, 1H), 7.78-7.75 (m, 1H), 7.43 (t, J=9.0 Hz, 1H), 7.34 (s, 1H), 6.02 (dd, J=45.0 Hz, $J_2$=11.0 Hz, 1H), 4.23-4.18 (m, 4H), 4.03 (s, 3H), 1.32-1.27 (m, 6H). HRMS (ESI): m/z calcd for $(C_{21}H_{22}ClF_2N_4O_5P+H)^+$: 515.1063. found: 515.1053.

Step 2: the preparation of N-(4-((3-chloro-4-fluorophenyl)amino)-7-methoxyquinazolin-6-yl)-2-fluoro-4-(piperidin-1-yl)but-2-enamide Starting material: 2-(piperidin-amino)-acetaldehyde was prepared according to the method in WO2011/126903.

The procedure was same with step 2 of example 1, and a pale yellow solid of N-(4-((3-chloro-4-fluorophenyl)amino)-7-methoxyquinazolin-6-yl)-2-fluoro-4-(piperidin-1-yl)but-2-enamide was given.

Rf value: 0.53, 0.56 (silica gel, dichloromethane/methanol=10:1; two isomers were separated)

Example 8

The preparation of (Z)—N-(4-((3-chloro-4-fluorophenyl)amino)-7-methoxyquinazolin-6-yl)-2-fluoro-4-(piperidin-1-yl)but-2-enamide, and (E)-N-(4-((3-chloro-4-fluorophenyl)amino)-7-methoxyquinazolin-6-yl)-2-fluoro-4-(piperidin-1-yl)but-2-enamide

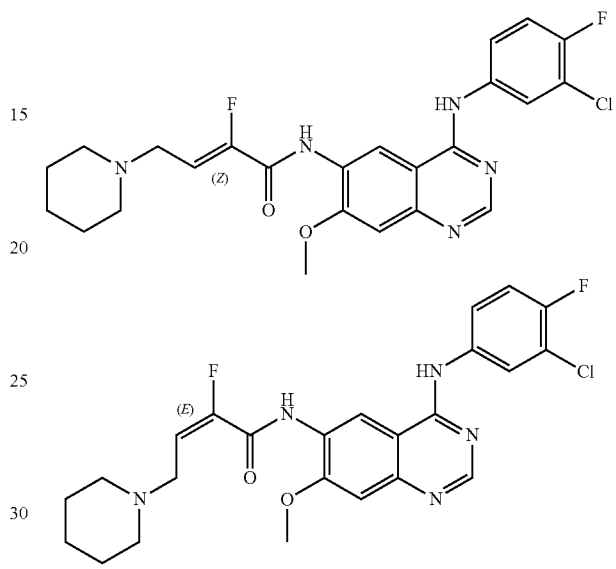

Use Thar SFC Pre80 supercritical chromatography to separate the mixture of cis and trans-isomers obtained in example 7.

Column: AD-H (20×250 mm, 5 μm, Tianjin Agela)
Detection wavelength: 254 nm;
Column Temperature: 38 degrees;
The dissolution of samples: dissolved in methanol and filtered;
Mobile phase: methanol (containing 0.1% DEA):$CO_2$=40:60

Collected the component at retention time of 4.65 min to obtain (E)-isomer (compound 8-2); and retention time of 6.85 min to obtain (Z)-isomer (compound 8-1).

Compound 8-1 $^1$H NMR (400 MHz, CDCl$_3$) δ 9.01 (s, 1H), 8.88 (d, J=4.4 Hz, 1H), 8.66 (s, 1H), 7.95 (dd, $J_1$=6.8 Hz, $J_2$=2.8 Hz, 1H), 7.81 (dd, J=3.2 Hz, $J_2$=0.5 Hz, 1H), 7.55 (ddd, J=9.0 Hz, $J_2$=4.0 Hz, $J_3$=2.8 Hz, 1H), 7.27 (s, 1H), 7.14 (t, J=8.8 Hz, 1H), 6.45 (dt, J=36.0 Hz, $J_2$=7.2 Hz, 1H), 4.07 (s, 3H), 3.34 (d, J=7.2 Hz, 2H), 2.54-2.50 (m, 4H), 1.68-1.64 (m, 4H), 1.50-1.46 (m, 2H). HRMS (ESI): m/z calcd for $(C_{24}H_{24}ClF_2N_5O_2+H)^+$: 488.1665. found: 488.1656.

Compound 8-2 $^1$H NMR (400 MHz, CDCl$_3$) δ 9.23 (s, 1H), 8.96 (s, 1H), 8.67 (s, 1H), 7.93 (dd, $J_1$=6.8 Hz, $J_2$=2.8 Hz, 1H), 7.73 (s, 1H), 7.57 (ddd, =9.0 Hz, $J_2$=4.0 Hz, $J_3$=2.8 Hz, 1H), 7.28 (s, 1H), 7.16 (t, J=8.8 Hz, 1H), 6.20 (dt, $J_1$=22.8 Hz, $J_2$=5.6 Hz, 1H), 4.07 (s, 3H), 3.79-3.74 (m, 2H), 2.64-2.61 (m, 4H), 1.73-1.68 (m, 4H), 1.54-1.47 (m, 2H). HRMS (ESI): m/z calcd for $(C_{24}H_{24}ClF_2N_5O_2+H)^+$: 488.1665. found: 488.1656.

Examples 9 to 18

According to the same method as example 1 or 7, the following compounds which were mixtures of cis and trans isomers were prepared with different starting materials.

| Example | Structure | Name and identification data |
|---|---|---|
| 9 | 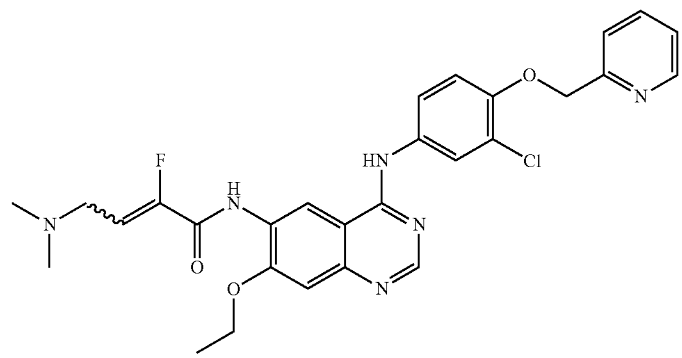 [SMILES: CCOc1cc2ncnc(Nc3ccc(OCc4ccccn4)c(Cl)c3)c2cc1NC(=O)C(F)=CCN(C)C] | N-(4-((3-chloro-4-(pyridin-2-ylmethoxy)phenyl)amino)-7-ethoxyquinazolin-6-yl)-4-(dimethylamino)-2-fluorobut-2-enamide<br>TLC Rf: 0.53, 0.56 (DCM:MeOH = 10:1)<br>LC/MS: Peak 1 $T_R$ = 5.72 min, $[M + H]^+$ = 551.1957<br>Peak 2 $T_R$ = 5.77 min, $[M + H]^+$ = 551.1959 |
| 10 | 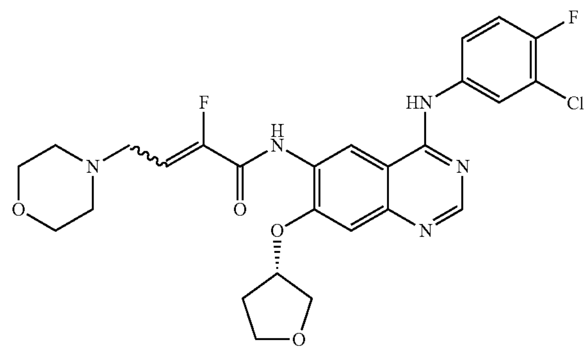 [SMILES: O=C(Nc1cc2c(Nc3ccc(F)c(Cl)c3)ncnc2cc1O[C@H]1CCOC1)C(F)=CCN1CCOCC1] | (S)-N-(4-((3-chloro-4-fluorophenyl)amino)-7-((tetrahydrofuran-3-yl)oxy)quinazolin-6-yl)-2-fluoro-4-morpholinobut-2-enamide<br>TLC Rf: 0.52, 0.56 (DCM:MeOH = 10:1)<br>LC/MS: Peak 1 $T_R$ = 5.90 min, $[M + H]^+$ = 546.1706<br>Peak 2 $T_R$ = 6.03 min, $[M + H]^+$ = 546.1704 |
| 11 | 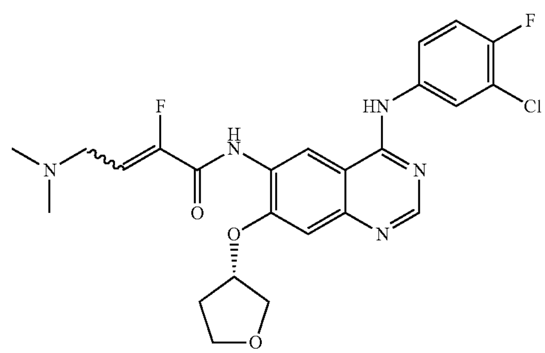 | (S)-N-(4-((3-chloro-4-fluorophenyl)amino)-7-((tetrahydrofuran-3-yl)oxy)quinazolin-6-yl)-4-(dimethylamino)-2-fluorobut-2-enamide<br>TLC Rf: 0.53, 0.58 (DCM:MeOH = 10:1)<br>LC/MS: Peak 1 $T_R$ = 5.65 min, $[M + H]^+$ = 504.1605<br>Peak 2 $T_R$ = 5.72 min, $[M + H]^+$ = 504.1603 |
| 12 | 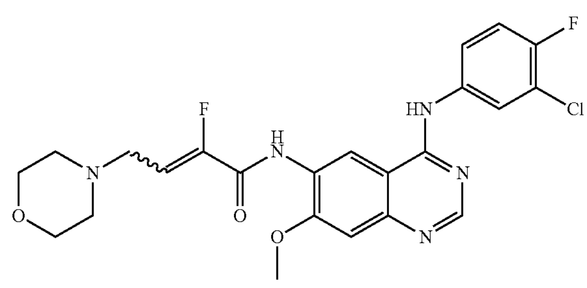 | N-(4-((3-chloro-4-fluorophenyl)amino)-7-methoxyquinazolin-6-yl)-2-fluoro-4-morpholinobut-2-enamide<br>TLC Rf: 0.52, 0.60 (DCM:MeOH = 10:1)<br>LC/MS: Peak 1 $T_R$ = 5.69 min, $[M + H]^+$ = 490.1451<br>Peak 2 $T_R$ = 5.76 min, $[M + H]^+$ = 490.1447 |
| 13 | 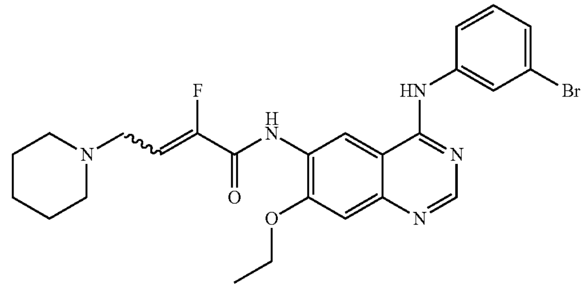 [SMILES: CCOc1cc2ncnc(Nc3cccc(Br)c3)c2cc1NC(=O)C(F)=CCN1CCCCC1] | N-(4-((3-bromophenyl)amino)-7-ethoxy-quinazolin-6-yl)-2-fluoro-4-(piperidin-1-yl)but-2-enamide<br>TLC Rf: 0.52, 0.62 (DCM:MeOH = 10:1)<br>LCMS: Peak 1 $T_R$ = 5.99 min, $[M + 2H]^+$ = 530.1394<br>Peak 2 $T_R$ = 6.16 min, $[M + 2H]^+$ = 530.1383 |

-continued

| Example | Structure | Name and identification data |
|---------|-----------|------------------------------|
| 14 | 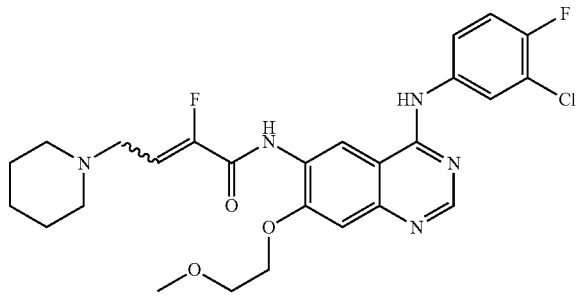 [SMILES: COCCOc1cc2ncnc(Nc3ccc(F)c(Cl)c3)c2cc1NC(=O)C(F)=CCN1CCCCC1] | N-(4-((3-chloro-4-fluorophenyl)amino)-7-(2-methoxyethoxy)quinazolin-6-yl)-2-fluoro-4-(piperidin-1-yl)but-2-enamide<br>TLC Rf: 0.52, 0.53 (DCM:MeOH = 10:1)<br>LC/MS: Peak 1 $T_R$ = 5.89 min, [M + H]$^+$ = 532.1927<br>Peak 2 $T_R$ = 5.99 min, [M + H]$^+$ = 532.1919 |
| 15 | 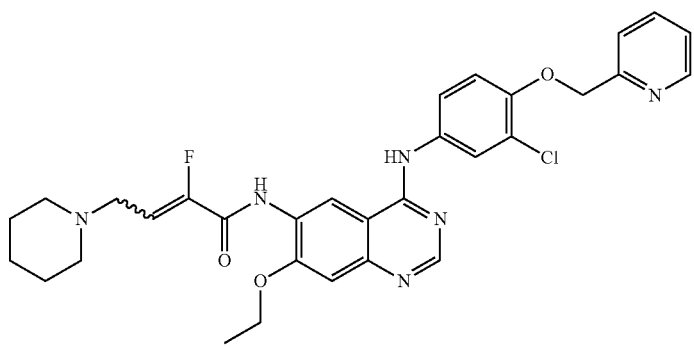 [SMILES: CCOc1cc2ncnc(Nc3ccc(OCc4ccccn4)c(Cl)c3)c2cc1NC(=O)C(F)=CCN1CCCCC1] | N-(4-((3-chloro-4-(pyridin-2-ylmethoxy)pheny)amino)-7-ethoxyquinazolin-6-yl)-2-fluoro-4-(piperidin-1-yl)but-2-enamide<br>TLC Rf: 0.52, 0.53 (DCM:MeOH = 10:1)<br>LC/MS: Peak 1 $T_R$ = 5.90 min, [M + H]$^+$ = 591.2256<br>Peak 2 $T_R$ = 6.00 min, [M + H]$^+$ = 591.2280 |
| 16 | 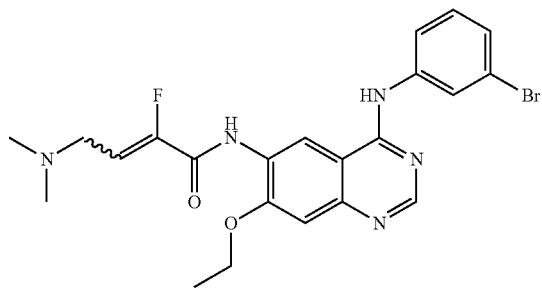 [SMILES: CCOc1cc2ncnc(Nc3cccc(Br)c3)c2cc1NC(=O)C(F)=CCN(C)C] | N-(4-((3-bromophenyl)amino)-7-ethoxyquinazolin-6-yl)-4-(dimethylamino)-2-fluorobut-2-enamide<br>MS (ESI$^+$): 488, 490 [M + H]$^+$ |
| 17 | 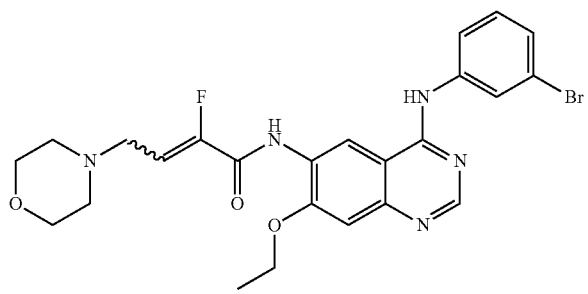 [SMILES: CCOc1cc2ncnc(Nc3cccc(Br)c3)c2cc1NC(=O)C(F)=CCN1CCOCC1] | N-(4-((3-bromophenyl)amino)-7-ethoxyquinazolin-6-yl)-2-fluoro-4-morpholinobut-2-enamide<br>MS (ESI$^+$): 530, 532 [M + H]$^+$ |
| 18 | 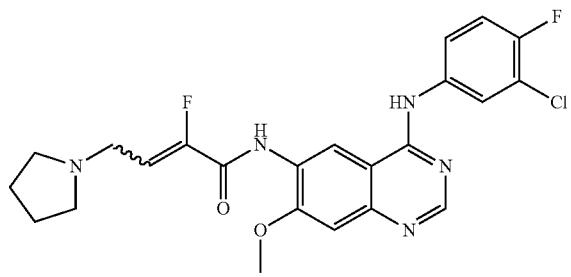 [SMILES: COc1cc2ncnc(Nc3ccc(F)c(Cl)c3)c2cc1NC(=O)C(F)=CCN1CCCC1] | N-(4-((3-chloro-4-fluorophenyl)amino)-7-methoxyquinazolin-6-yl)-2-fluoro-4-(pyrrolidin-1-yl)but-2-enamide<br>MS (ESI$^+$): 474 [M + H]$^+$ |

Examples 19 to 22

Using the SFC equipment in example 8, separate the compounds that were obtained in examples 9 to 12 (the mixture of cis and trans isomers) and give the following compounds.

| Example | Structure | Name and identification data |
|---|---|---|
| 19-1 | 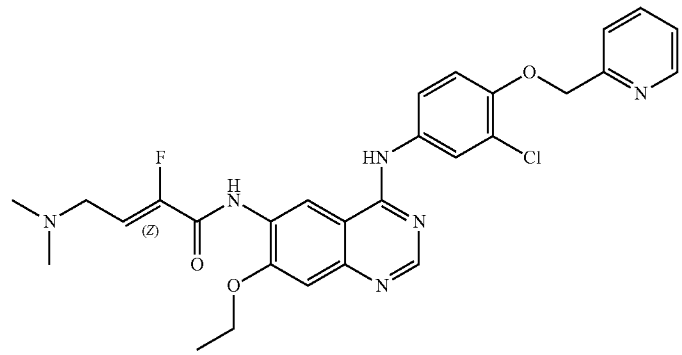 [SMILES: CCOc1cc2ncnc(Nc3ccc(OCc4ccccn4)c(Cl)c3)c2cc1NC(=O)/C(F)=C/CN(C)C] | (Z)-N-(4-((3-chloro-4-(pyridin-2-ylmethoxy)phenyl)amino)-7-ethoxyquinazolin-6-yl)-4-(dimethylamino)-2-fluorobut-2-enamide<br>$^1$H NMR (400 MHz, CDCl$_3$) δ 9.00 (s, 1H), 8.98 (d, J = 5.6 Hz, 1H), 8.63 (s, 1H), 8.59 (d, J = 4.4 Hz, 1H), 7.88 (d, J = 2.8 Hz, 1H), 7.79-7.78 (m, 1H), 7.75 (d, J$_1$ = 7.6 Hz, J$_2$ = 1.6 Hz, 1H), 7.67 (d, J = 8.0 Hz, 1H), 7.52 (dd, J$_1$ = 8.8 Hz, J$_2$ = 2.8 Hz, 1H), 7.25 (s, 1H), 7.01 (d, J = 8.8 Hz, 1H), 6.39 (dt, J$_1$ = 36.4 Hz, J$_2$ = 7.2 Hz, 1H), 5.30 (s, 2H), 4.30 (q, J = 6.8 Hz, 2H), 3.26 (dd, J$_1$ = 7.2 Hz, J$_2$ = 2.4 Hz, 2H), 2.32 (s, 6H), 1.57 (t, J = 7.2 Hz, 4H).<br>LCMS: HRMS (ESI): m/z calcd for (C$_{28}$H$_{28}$ClFN$_6$O$_3$ + H)$^+$: 551.1973; found: 551.1957. |
| 19-2 | 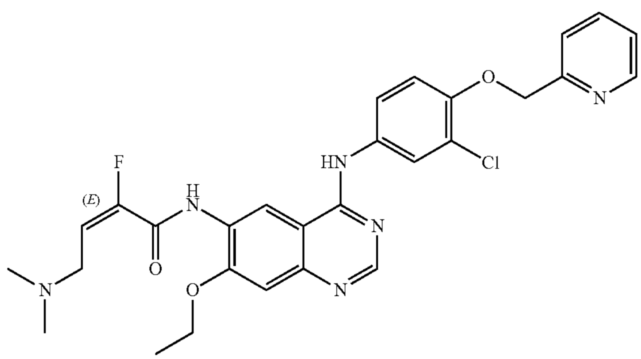 [SMILES: CCOc1cc2ncnc(Nc3ccc(OCc4ccccn4)c(Cl)c3)c2cc1NC(=O)/C(F)=C\CN(C)C] | (E)-N-(4-((3-chloro-4-(pyridin-2-ylmethoxy)phenyl)amino)-7-ethoxyquinazolin-6-yl)-4-(dimethylamino)-2-fluorobut-2-enamide<br>HNMR: $^1$H NMR (400 MHz, CDCl$_3$) δ 9.19 (d, J = 4.8 Hz, 1H), 8.98 (s, 1H), 8.65 (s, 1H), 8.60 (dd, J$_1$ = 5.6 Hz, J$_2$ = 0.8 Hz, 1H), 7.86 (d, J = 2.8 Hz, 1H), 7.78-7.74 (m, 1H), 7.7-7.66 (m, 1H), 7.55-7.52 (m, 1H), 7.48-7.47 (m, 1H), 7.03 (d, J = 9.2 Hz, 1H), 6.25-6.19 (m, 1H), 5.35 (m, 1H), 5.30 (s, 2H), 4.31 (q, J = 7.2 Hz, 2H), 3.96-3.92 (m, 2H), 2.59-2.55 (s, 6H), 1.57 (t, J = 6.8 Hz, 3H).<br>LCMS: HRMS (ESI): m/z calcd for (C$_{28}$H$_{28}$ClFN$_6$O$_3$ + H)$^+$: 551.1973; found: 551.1959. |
| 20-1 | 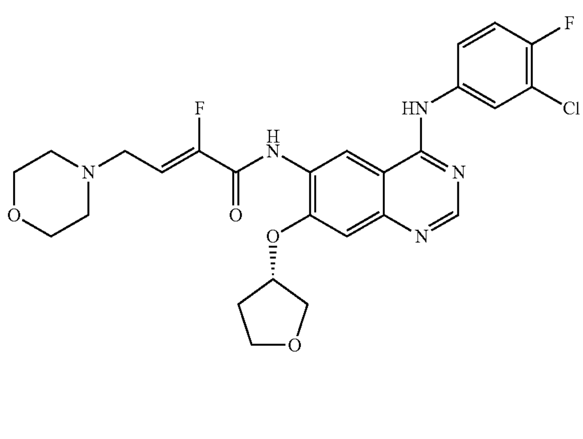 [SMILES: O=C(Nc1cc2c(Nc3ccc(F)c(Cl)c3)ncnc2cc1O[C@H]1CCOC1)/C(F)=C/CN1CCOCC1] | (S,Z)-N-(4-((3-chloro-4-fluorophenyl)amino)-7-((tetrahydrofuran-3-yl)oxy)quinazolin-6-yl)-2-fluoro-4-morpholinobut-2-enamide<br>$^1$H NMR (400 MHz, CDCl$_3$) δ 9.03 (s, 1H), 8.91 (d, J = 4.4 Hz, 1H), 8.67 (s, 1H), 7.97 (dd, J$_1$ = 6.4 Hz, J$_2$ = 2.4 Hz, 1H), 7.75 (s, 1H), 7.59-7.55 (m, 1H), 7.22(s, 1H), 7.17 (t, J = 8.8 Hz, 1H), 6.40 (dt, J$_1$ = 36.4 Hz, J$_2$ = 6.4 Hz, 1H), 5.21 (s, 2H), 4.14-4.05 (m, 4H), 4.00-3.94 (m, 1H), 3.76-3.74 (m, 4H), 3.31 (dd, J$_1$ = 7.2 Hz, J$_2$ = 2.4 Hz, 2H), 2.55-2.53 (m, 4H).<br>LCMS: HRMS (ESI): m/z calcd for (C$_{28}$H$_{28}$ClFN$_6$O$_3$ + H)$^+$: 551.1973; found: 551.1959. |

| Example | Structure | Name and identification data |
|---|---|---|
| 20-2 | 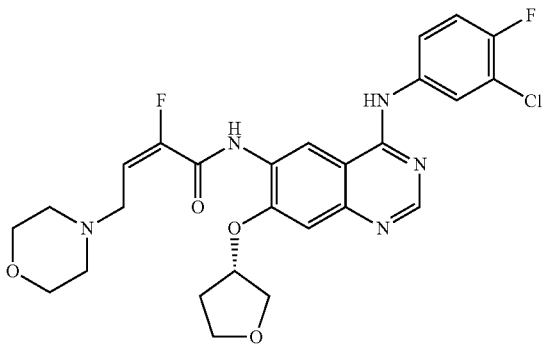 [SMILES: O=C(Nc1cc2c(Nc3ccc(F)c(Cl)c3)ncnc2cc1O[C@H]1CCOC1)/C(F)=C\CN1CCOCC1] | (S,E)-N-(4-((3-chloro-4-fluorophenyl)amino)-7-((tetrahydrofuran-3-yl)oxy)quinazolin-6-yl)-2-fluoro-4-morpholinobut-2-enamide<br>HNMR: $^1$H NMR (400 MHz, CDCl$_3$) δ 9.02 (s, 1H), 8.98 (d, J = 6.0 Hz, 1H), 8.67 (s, 1H), 7.96 (dd, J$_1$ = 6.4 Hz, J$_2$ = 2.8 Hz, 1H), 7.59-7.55 (m, 2H), 7.22 (s, 1H), 7.19 (d, J = 8.8 Hz, 1H), 6.08 (dt, J$_1$ = 23.6 Hz, J$_2$ = 6.4 Hz, 1H), 5.20 (s, 2H), 4.10-4.04 (m, 4H), 4.00-3.96 (m, 1H), 3.76-3.74 (m, 4H), 3.71 (dd, J$_1$ = 6.8 Hz, J$_2$ = 2.4 Hz, 2H), 2.58-2.55 (m, 4H).<br>LCMS: HRMS (ESI): m/z calcd for (C$_{26}$H$_{26}$ClF$_2$N$_5$O$_4$ + H)$^+$: 546.1719; found: 546.1706. |
| 21-1 | 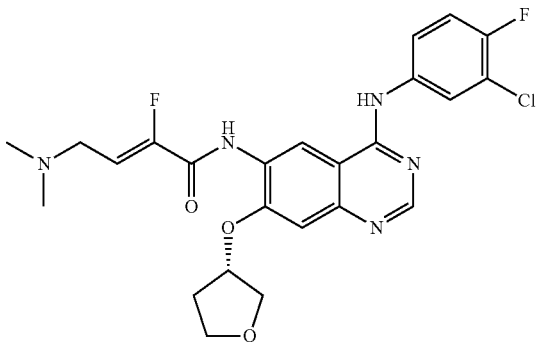 [SMILES: CN(C)C/C=C(\F)C(=O)Nc1cc2c(Nc3ccc(F)c(Cl)c3)ncnc2cc1O[C@H]1CCOC1] | (S,Z)-N-(4-((3-chloro-4-fluorophenyl)amino)-7-((tetrahydrofuran-3-yl)oxy)quinazolin-6-yl)-4-(dimethylamino)-2-fluorobut-2-enamide<br>$^1$H NMR (400 MHz, CDCl$_3$) δ 9.05 (s, 1H), 8.91 (d, J = 6.8 Hz, 1H), 8.67 (s, 1H), 7.98 (dd, J$_1$ = 6.8 Hz, J$_2$ = 2.8 Hz, 1H), 7.73 (s, 1H), 7.59-7.55 (m, 1H), 7.22 (s, 1H), 7.18 (t, J = 8.8 Hz, 1H), 6.40 (dt, J$_1$ = 36.4 Hz, J$_2$ = 7.2 Hz, 1H), 5.22-5.19 (m, 1H), 4.12-4.07 (m, 4H), 4.00-3.94 (m, 1H), 3.26 (dd, J$_1$ = 7.6 Hz, J$_2$ = 2.8 Hz, 2H), 2.33 (s, 6H).<br>LCMS: HRMS (ESI): m/z calcd for (C$_{24}$H$_{24}$ClF$_2$N$_5$O$_3$ + H)$^+$: 504.1614; found: 504.1605. |
| 21-2 | 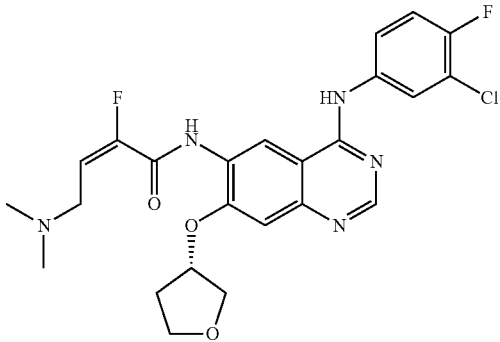 [SMILES: CN(C)C/C=C(/F)C(=O)Nc1cc2c(Nc3ccc(F)c(Cl)c3)ncnc2cc1O[C@H]1CCOC1] | (S,E)-N-(4-((3-chloro-4-fluorophenyl)amino)-7-((tetrahydrofuran-3-yl)oxy)quinazolin-6-yl)-4-(dimethylamino)-2-fluorobut-2-enamide<br>$^1$H NMR (400 MHz, CDCl$_3$) δ 9.26 (brs, 1H), 9.00 (s, 1H), 8.67 (s, 1H), 7.95 (dd, J$_1$ = 6.4 Hz, J$_2$ = 2.8 Hz, 1H), 7.62 (s, 1H), 7.59-7.54 (m, 1H), 7.22 (s, 1H), 7.18 (t, J = 8.8 Hz, 1H), 6.09 (dt, J$_1$ = 24.8 Hz, J$_2$ = 6.8 Hz, 1H), 5.20-5.16 (m, 2H), 4.10-4.04 (m, 4H), 3.98-3.95 (m, 1H), 3.60 (dd, J$_1$ = 7.2 Hz, J$_2$ = 2.8 Hz, 2H), 2.34 (s, 6H).<br>LCMS: HRMS (ESI): m/z calcd for (C$_{24}$H$_{24}$ClF$_2$N$_5$O$_3$ + H)$^+$: 504.1614; found: 504.1603. |
| 22-1 | 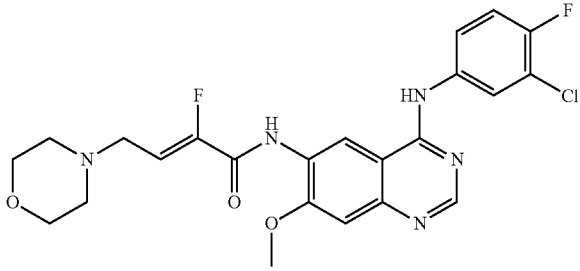 | (Z)-N-(4-((3-chloro-4-fluorophenyl)amino)-7-methoxyquinazolin-6-yl)-2-fluoro-4-morpholinobut-2-enamide<br>$^1$H NMR (400 MHz, CDCl$_3$) δ 9.01 (s, 1H), 8.91 (d, J = 4.8 Hz, 1H), 8.67 (s, 1H), 7.95 (dd, J$_1$ = 6.4 Hz, J$_2$ = 2.4 Hz, 1H), 7.75 (s, 1H), 7.57-7.54 (m, 1H), 7.29 (s, 1H), 7.15 (t, J = 8.8 Hz, 1H), 6.38 (dt, J$_1$ = 36.0 Hz, J$_2$ = 7.2 Hz, 1H), 4.08 (s, 3H), 3.75 (t, J = 4.4 Hz, 4H), 3.31 (dd, J$_1$ = 7.2 Hz, J$_2$ = 2.4 Hz, 2H), 2.54 (t, J = 4.4 Hz, 4H).<br>LCMS: HRMS (ESI): m/z calcd for (C$_{23}$H$_{22}$ClF$_2$N$_5$O$_3$ + H)$^+$: 490.1457; found: 490.1447. |

| Example | Structure | Name and identification data |
|---|---|---|
| 22-2 | 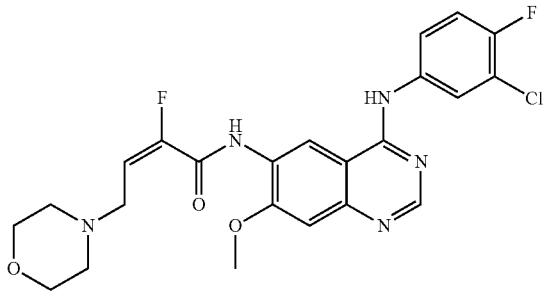 [SMILES: COc1cc2ncnc(Nc3ccc(F)c(Cl)c3)c2cc1NC(=O)/C(F)=C\CN1CCOCC1] | (E)-N-(4-((3-chloro-4-fluorophenyl)amino)-7-methoxyquinazolin-6-yl)-2-fluoro-4-morpholinobut-2-enamide<br>$^1$H NMR (400 MHz, CDCl$_3$) δ 9.05 (d, J = 5.2 Hz, 1H), 9.00 (s, 1H), 8.68 (s, 1H), 7.95 (dd, J$_1$ = 6.4 Hz, J$_2$ = 2.8 Hz, 1H), 7.58-7.54 (m, 2H), 7.30 (s, 1H), 7.17 (t, J = 8.4 Hz, 1H), 6.07 (dt, J$_1$ = 23.6 Hz, J$_2$ = 6.8 Hz, 1H), 4.08 (s, 3H), 3.75 (t, J = 4.8 Hz, 4H), 3.70 (dd, J$_1$ = 6.8 Hz, J$_2$ = 2.4 Hz, 2H), 2.57 (t, J = 4.8 Hz, 4H).<br>LCMS: HRMS (ESI): m/z calcd for (C$_{23}$H$_{22}$ClF$_2$N$_5$O$_3$ + H)$^+$: 490.1457; found: 490.1451. |

Example 23~88

According to the same method as example 5 or 6, the following compounds were prepared with different starting materials.

| Example | Structure | Name and Identification data |
|---|---|---|
| 23 | 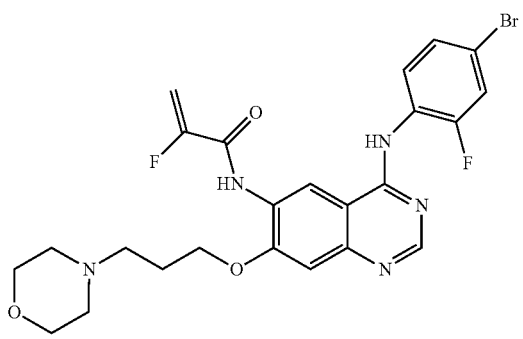 [SMILES: C=C(F)C(=O)Nc1cc2c(Nc3ccc(Br)cc3F)ncnc2cc1OCCCN1CCOCC1] | N-[4-(4-Bromo-2-fluoro-phenylamino)-7-(3-morpholin-4-yl-propoxy)-quinazolin-6-yl]-2-fluoro-acrylamide<br>$^1$H NMR (300 MHz, d-DMSO) δ: 1.96 (m, 2H), 2.38 (m, 4H), 2.45 (t, 2H, J = 5.1 Hz), 3.58 (m, 4H), 4.26 (t, 2H, J = 4.5 Hz), 5.52 (dd, 1H, J$_1$ = 2.7 Hz, J$_2$ = 11.7 Hz), 5.76 (dd, 1H, J$_1$ = 2.7 Hz, J$_2$ = 36.3 Hz), 7.31 (s, 1H), 7.48 (m, 1H), 7.48 (m, 1H), 7.66 (m, 1H), 8.42 (s, 1H), 8.70 (s, 1H), 9.70 (s, 1H), 9.80 (s, 1H). |
| 24 | 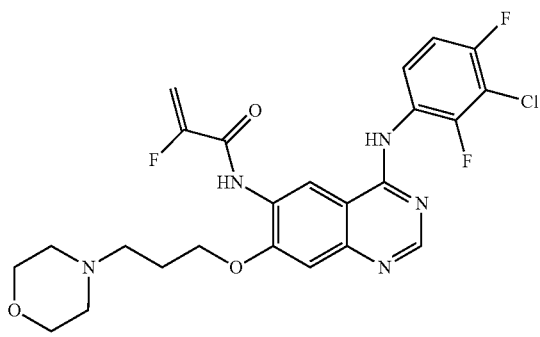 | N-[4-(3-chloro-2,4-difluoro-phenylamino)-7-(3-morpholin-4-yl-propoxy)-quinazolin-6-yl]-2-fluoro-acrylamide<br>$^1$H NMR (300 MHz, d-DMSO) δ: 1.96 (m, 2H), 2.38 (m, 4H), 2.46 (t, 2H, J = 5.1 Hz), 3.58 (m, 4H), 4.26 (t, 2H, J = 4.5 Hz), 5.52 (dd, 1H, J$_1$ = 2.7 Hz, J$_2$ = 11.7 Hz), 5.76 (dd, 1H, J$_1$ = 2.7 Hz, J$_2$ = 36.3 Hz), 7.32 (s, 1H), 7.39 (m, 1H), 7.53 (m, 1H), 8.44 (s, 1H), 8.71 (s, 1H), 9.68 (s, 1H), 9.91 (s, 1H). |
| 25 | 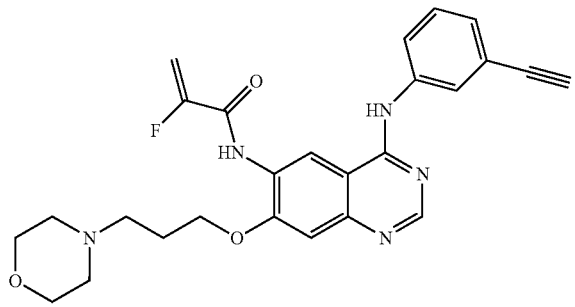 [SMILES: C#Cc1cccc(Nc2ncnc3cc(OCCCN4CCOCC4)c(NC(=O)C(=C)F)cc23)c1] | N-[4-(3-ethynyl-phenylamino)-7-(3-morpholin-4-yl-propoxy)-quinazolin-6-yl]-2-fluoro-acrylamide<br>$^1$H NMR (300 MHz, d-DMSO) δ: 1.96 (m, 2H), 2.38 (m, 4H), 2.47 (t, 2H, J = 6.9 Hz), 3.58 (m, 4H, J = 4.5 Hz), 4.19 (s, 1H), 4.24 (t, 2H, J = 5.7 Hz), 5.51 (dd, 1H, J$_1$ = 3.6 Hz, J$_2$ = 15.9 Hz), 5.76 (dd, 1H, J$_1$ = 3.9 Hz, J$_2$ = 48 Hz), 7.20 (d, 1H, J = 7.8 Hz), 7.31 (s, 1H), 7.39 (t, 1H, J = 7.8 Hz), 7.89 (d, 1H, J = 8.4 Hz), 8.03 (s, 1H), 8.57 (s, 1H), 8.72 (s, 1H), 9.77 (m, 2H). |

| Example | Structure | Name and Identification data |
|---|---|---|
| 26 | 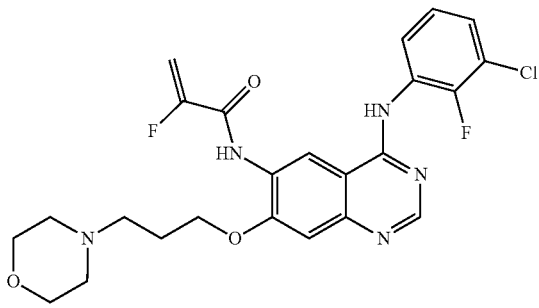 [SMILES: C=C(F)C(=O)Nc1cc2c(Nc3cccc(Cl)c3F)ncnc2cc1OCCCN1CCOCC1] | N-[4-(3-chloro-2-fluoro-phenylamino)-7-(3-morpholin-4-yl-propoxy)-quinazolin-6-yl]-2-fluoro-acrylamide<br>$^1$H NMR (300 MHz, d-DMSO) δ: 1.97 (m, 2H), 2.38 (m, 4H), 2.46 (t, 2H, J = 6.9 Hz), 3.58 (t, 4H, J = 4.5 Hz), 4.26 (t, 2H, J = 6.0 Hz), 5.51 (dd, 1H, $J_1$ = 3.9 Hz, $J_2$ = 15.6 Hz), 5.76 (dd, 1H, $J_1$ = 3.9 Hz, $J_2$ = 48.3 Hz), 7.27 (m, 2H), 7.48 (m, 1H), 8.45 (s, 1H), 8.71 (s, 1H), 9.69 (s, 1H), 9.90 (s, 1H). |
| 27 | 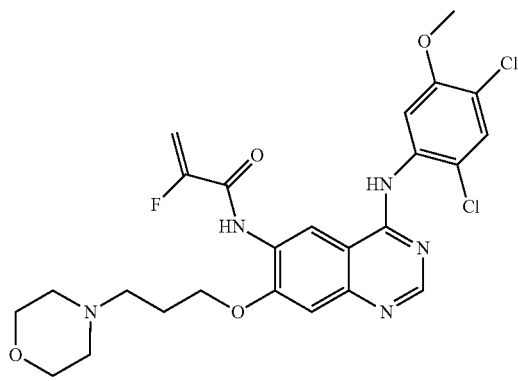 [SMILES: C=C(F)C(=O)Nc1cc2c(Nc3cc(OC)c(Cl)cc3Cl)ncnc2cc1OCCCN1CCOCC1] | N-[4-(2,4-dichloro-5-methoxy-phenylamino)-7-(3-morpholin-4-yl-propoxy)-quinazolin-6-yl]-2-fluoro-acrylamide<br>$^1$H NMR (300 MHz, CD$_3$OD) δ: 1.99 (m, 2H), 2.38 (m, 4H), 2.48 (t, 2H, J = 6.9 Hz), 3.58 (m, 4H), 3.91 (s, 3H), 4.52 (t, 2H, J = 6.0 Hz), 5.66 (dd, 1H, $J_1$ = 2.4 Hz, $J_2$ = 33.3 Hz), 5.76 (dd, 1H, $J_1$ = 2.7 Hz, $J_2$ = 35.4 Hz), 7.34 (s, 1H), 7.44 (s, 1H), 7.64 (s, 1H), 8.71 (s, 1H), 9.10 (s, 1H). |
| 28 | 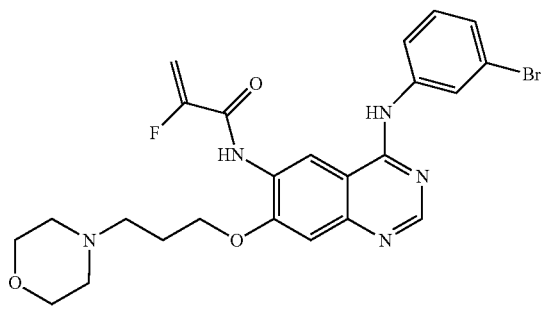 [SMILES: C=C(F)C(=O)Nc1cc2c(Nc3cccc(Br)c3)ncnc2cc1OCCCN1CCOCC1] | N-[4-(3-bromo-phenylamino)-7-(3-morpholin-4-yl-propoxy)-quinazolin-6-yl]-2-fluoro-acrylamide<br>$^1$H NMR (300 MHz, CD$_3$OD) 1.95 (m, 2H), 2.35 (m, 4H), 2.44 (t, 2H, J = 5.4 Hz), 3.56 (t, 4H, J = 3.3 Hz), 4.23 (t, 2H, J = 4.2 Hz), 5.49 (dd, 1H, $J_1$ = 2.4 Hz, $J_2$ = 12 Hz), 5.74 (dd, 1H, $J_1$ = 2.7 Hz, $J_2$ = 36 Hz), 7.30 (m, 3H), 7.86 (d, 1H, J = 6.3 Hz), 8.17 (s, 1H), 8.57 (s, 1H), 8.71 (s, 1H). |
| 29 | 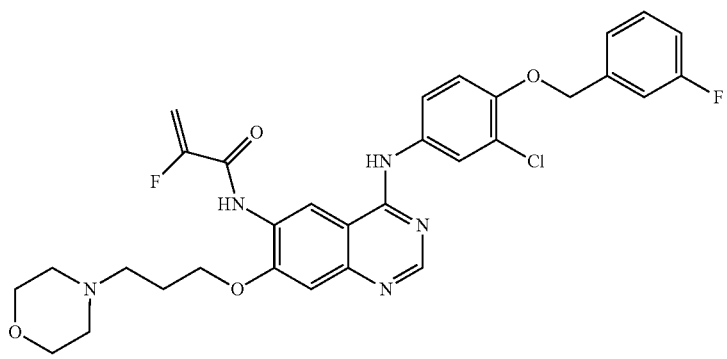 [SMILES: C=C(F)C(=O)Nc1cc2c(Nc3ccc(OCc4cccc(F)c4)c(Cl)c3)ncnc2cc1OCCCN1CCOCC1] | N-[4-[3-chloro-4-(3-fluoro-benzyloxy)-phenylamino]-7-(3-morpholin-4-yl-propoxy)-quinazolin-6-yl]-2-fluoro-acrylamide<br>$^1$H NMR (300 MHz, d-DMSO) δ: 0.84 (m, 2H), 1.97 (m, 4H), 2.43 (t, 2H, J = 5.4 Hz), 3.59 (m, 4H), 4.24 (t, 2H, J = 4.2 Hz), 5.24 (s, 2H), 5.49 (dd, 1H, $J_1$ = 2.4 Hz, $J_2$ = 12 Hz), 5.75 (dd, 1H, $J_1$ = 2.7 Hz, $J_2$ = 36 Hz), 7.29 (m, 4H), 7.46 (m, 1H), 7.70 (d, 1H, J = 7.8 Hz), 7.99 (s, 1H), 8.52 (s, 1H), 8.68 (s, 1H), 9.71 (s, 1H), 9.78 (s, 1H). |

-continued

| Example | Structure | Name and Identification data |
|---|---|---|
| 30 | 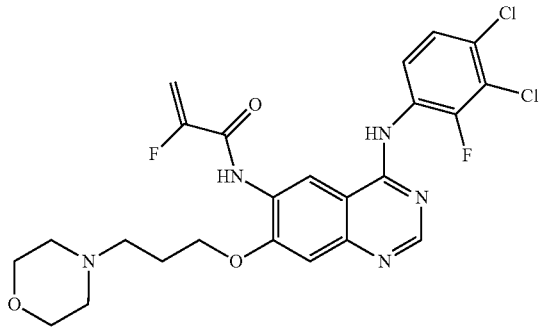 [SMILES: C=C(F)C(=O)Nc1cc2c(Nc3ccc(Cl)c(Cl)c3F)ncnc2cc1OCCCN1CCOCC1] | N-[4-(3,4-dichloro-2-fluoro-phenylamino)-7-(3-morpholin-4-yl-propoxy)-quinazolin-6-yl]-2-fluoro-acrylamide<br>$^1$H NMR (300 MHz, d-DMSO) δ: 2.01 (m, 2H), 2.50 (m, 4H), 2.60 (t, 2H, J = 5.4 Hz), 3.62 (m, 4H), 4.27 (t, 2H, J = 4.2 Hz), 5.36 (dd, 1H, J$_1$ = 2.4 Hz, J$_2$ = 12 Hz), 5.52 (dd, 1H, J$_1$ = 2.7 Hz, J$_2$ = 36 Hz), 7.32 (m, 1H), 7.55 (m, 1H), 8.45 (s, 1H), 8.71 (s, 1H), 9.70 (s, 1H), 10.37 (s, 1H). |
| 31 | 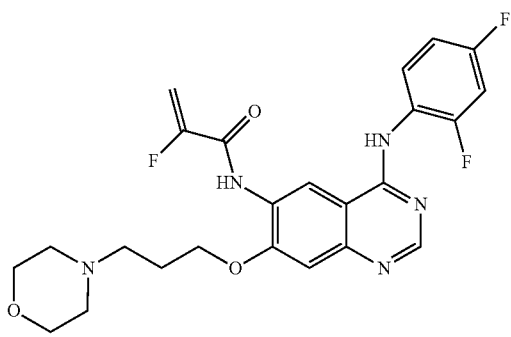 [SMILES: C=C(F)C(=O)Nc1cc2c(Nc3ccc(F)cc3F)ncnc2cc1OCCCN1CCOCC1] | N-[4-(2,4-difluoro-phenylamino)-7-(3-morpholin-4-yl-propoxy)-quinazolin-6-yl]-2-fluoro-acrylamide<br>$^1$H NMR (300 MHz, d-DMSO) δ: 1.96 (m, 2H), 2.38 (m, 4H), 2.47 (t, 2H, J = 5.4 Hz), 3.58 (t, 2H, J = 2.7 Hz), 4.25 (t, 2H, J = 4.2 Hz), 5.51 (dd, 1H, J$_1$ = 2.4 Hz, J$_2$ = 12 Hz), 5.76 (dd, 1H, J$_1$ = 2.7 Hz, J$_2$ = 36 Hz), 7.14 (m, 1H), 7.33 (m, 1H), 7.52 (m, 1H), 8.40 (s, 1H), 8.68 (s, 1H), 9.72 (d, 1H, J = 12.3 Hz). |
| 32 | 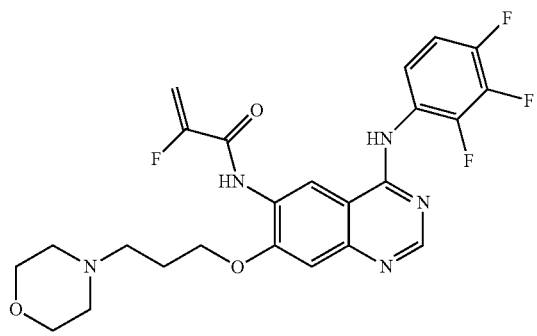 [SMILES: C=C(F)C(=O)Nc1cc2c(Nc3ccc(F)c(F)c3F)ncnc2cc1OCCCN1CCOCC1] | N-[7-(3-morpholin-4-yl-propoxy)-4-(2,3,4-trifluoro-phenylamino)-quinazolin-6-yl]-2-fluoro-acrylamide<br>$^1$H NMR (300 MHz, d-DMSO) δ: 1.98 (m, 2H), 2.37 (m, 4H), 2.47 (t, 2H, J = 5.4 Hz), 3.57 (m, 4H), 4.26 (t, 2H, J = 4.2 Hz), 5.52 (dd, 1H, J$_1$ = 2.7 Hz, J$_2$ = 12 Hz), 5.76 (dd, 1H, J$_1$ = 2.7 Hz, J$_2$ = 36 Hz), 7.37 (m, 2H), 8.44 (s, 1H), 8.71 (m, 1H), 9.69 (s, 1H), 9.93 (s, 1H). |
| 33 | 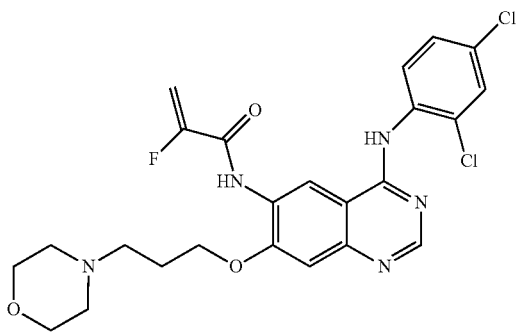 [SMILES: C=C(F)C(=O)Nc1cc2c(Nc3ccc(Cl)cc3Cl)ncnc2cc1OCCCN1CCOCC1] | N-[4-(2,4-dichloro-phenylamino)-7-(3-morpholin-4-yl-propoxy)-quinazolin-6-yl]-2-fluoro-acrylamide<br>MS (ESI$^+$): 520 [M + H]$^+$ |

| Example | Structure | Name and Identification data |
|---|---|---|
| 34 | 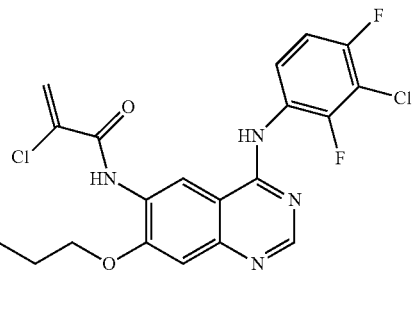 | N-[4-(3-chloro-2,4-difluoro-phenylamino)-7-(3-morpholin-4-yl-propoxy)-quinazolin-6-yl]-2-chloro-acrylamide<br>$^1$H NMR (300 MHz, CD$_3$OD) δ: 2.29 (m, 2H), 2.97 (m, 4H), 3.06 (t, 2H, J = 6.9 Hz), 3.83 (t, 4H, J = 4.5 Hz), 4.39 (t, 2H, J = 6 Hz), 5.77 (s, 1H), 6.08 (d, 1H, J = 1.8 Hz), 6.39 (s, 1H), 6.71 (d, 1H, J = 1.2 Hz), 7.24 (m, 2H), 7.53 (m, 1H), 8.40 (s, 1H), 8.93 (s, 1H). |
| 35 | 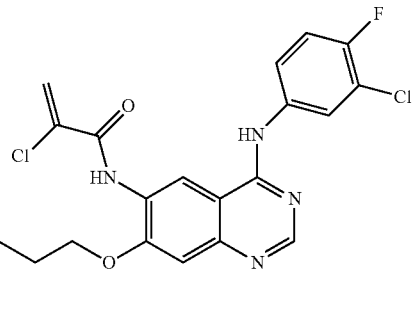 | N-[4-(3-chloro-4-fluoro-phenylamino)-7-(3-morpholin-4-yl-propoxy)-quinazolin-6-yl]-2-chloro-acrylamide<br>$^1$H NMR (300 MHz, CD$_3$OD) δ: 2.02 (m, 2H), 2.80 (m, 4H), 2.91 (t, 2H, J = 6.9 Hz), 3.66 (t, 4H, J = 5.7 Hz), 4.37 (t, 2H, J = 5.7 Hz), 5.74 (s, 1H), 6.09 (d, 1H, J = 1.8 Hz), 6.27 (s, 1H), 6.72 (d, 1H, J = 1.8 Hz), 7.24 (m, 2H), 7.27 (m, 2H), 7.67 (m, 1H), 8.01 (m, 1H), 8.50 (s, 1H), 8.91 (s, 1H). |
| 36 | 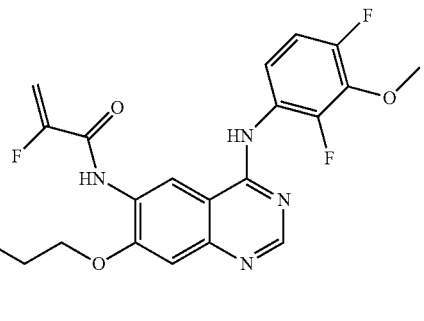 | N-[4-(2,4-difluoro-3-methoxy-phenylamino)-7-(3-morpholin-4-yl-propoxy)-quinazolin-6-yl]-2-fluoro-acrylamide<br>$^1$H NMR (300 MHz, d-DMSO) δ: 1.94 (m, 2H), 2.38 (m, 4H), 2.48 (t, 2H, J = 5.4 Hz), 3.55 (m, 4H), 4.09 (s, 3H), 4.23 (t, 2H, J = 6 Hz), 5.49 (dd, 1H, J$_1$ = 3.6 Hz, J$_2$ = 15.9 Hz), 5.76 (dd, 1H, J$_1$ = 3.6 Hz, J$_2$ = 48.3 Hz), 7.17 (d, 1H, J = 9 Hz), 7.28 (s, 1H), 8.39 (s, 1H), 8.66 (m, 1H), 8.73 (d, 1H, J = 16.2 Hz). |
| 37 | 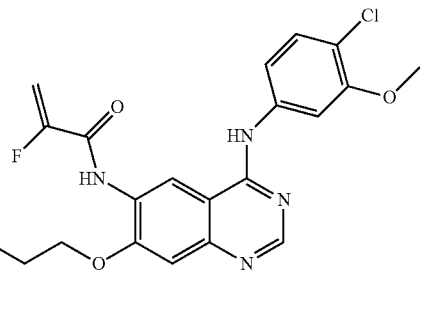 | N-[4-(4-chloro-3-methoxy-phenylamino)-7-(3-morpholin-4-yl-propoxy)-quinazolin-6-yl]-2-fluoro-acrylamide<br>$^1$H NMR (300 MHz, d-DMSO) δ: 1.97 (m, 2H), 2.31 (m, 4H), 2.46 (t, 2H, J = 5.4 Hz), 3.56 (m, 4H), 3.87 (s, 3H), 4.25 (t, 2H, J = 5.2 Hz), 5.51 (dd, 1H, J$_1$ = 2.7 Hz, J$_2$ = 11.7 Hz), 5.76 (dd, 1H, J$_1$ = 2.7 Hz, J$_2$ = 36 Hz), 7.31 (s, 1H), 7.39 (d, 1H, J = 6.3 Hz), 7.62 (m, 1H), 7.70 (m, 1H), 8.58 (s, 1H), 8.72 (s, 1H), 9.77 (d, 1H, J = 13.8 Hz). |

-continued

| Example | Structure | Name and Identification data |
|---|---|---|
| 38 | 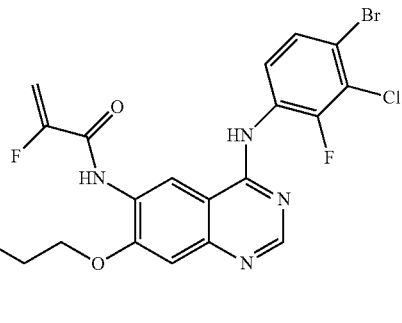 | N-[4-(4-bromo-3-chloro-2-fluoro-phenylamino)-7-(3-morpholin-4-yl-propoxy)-quinazolin-6-yl]-2-fluoro-acrylamide<br>$^1$H NMR (300 MHz, d-DMSO) δ: 1.97 (m, 2H), 2.50 (m, 4H), 2.59 (t, 2H, J = 6.9 Hz), 3.74 (m, 4H), 4.31 (t, 2H, J = 6.3 Hz), 5.34 (dd, 1H, J$_1$ = 2.7 Hz, J$_2$ = 11.7 Hz), 5.9 (dd, 1H, J$_1$ = 2.7 Hz, J$_2$ = 36 Hz), 7.26 (m, 1H), 7.43 (d, 1H, J = 8.7 Hz), 7.76 (s, 1H), 8.25 (m, 1H), 8.67 (s, 1H), 8.95 (s, 1H), 9.05 (s, 1H). |
| 39 | 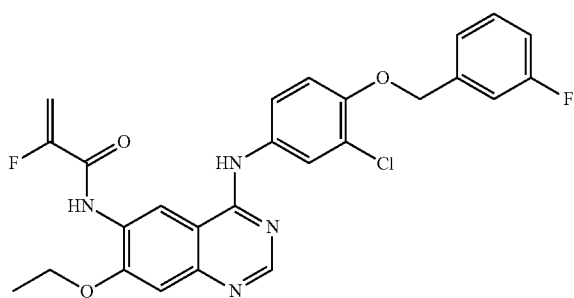 [SMILES: C=C(F)C(=O)Nc1cc2c(Nc3ccc(OCc4cccc(F)c4)c(Cl)c3)ncnc2cc1OCC] | N-{4-[3-chloro-4-(3-fluoro-benzyloxy)-phenylamino]-7-ethoxy-quinazolin-6-yl}-2-fluoro-acrylamide<br>$^1$H NMR (500 MHz, DMSO) δ 9.74 (s, 1H), 9.71 (s, 1H), 8.71 (s, 1H), 8.52 (s, 1H), 8.00 (d, J = 2.5 Hz, 1H), 7.72-7.69 (m, 1H), 7.50-7.45 (m, 1H), 7.34-7.28 (m, 3H), 7.25 (d, J = 9.0 Hz, 1H), 7.20-7.17 (m, 1H), 5.77 (dd, J = 48.1, 3.7 Hz, 1H), 5.51 (dd, J = 15.7, 3.7 Hz, 1H), 5.25 (s, 2H), 4.27 (q, J = 6.9 Hz, 2H), 1.42 (t, J = 6.9 Hz, 3H). |
| 40 | 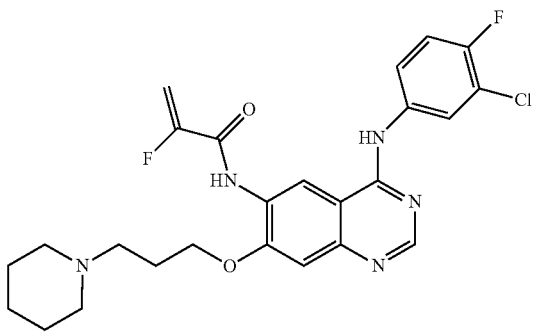 [SMILES: C=C(F)C(=O)Nc1cc2c(Nc3ccc(F)c(Cl)c3)ncnc2cc1OCCCN1CCCCC1] | N-[4-(3-chloro-4-fluoro-phenylamino)-7-(3-piperidin-1-yl-propoxy)-quinazolin-6-yl]-2-fluoro-acrylamide<br>$^1$H NMR (300 MHz, DMSO) δ 9.94 (s, 1H), 9.87 (s, 1H), 8.70s, 1H), 8.59 (s, 1H), 8.19 (q, J = 3 Hz, 1H), 7.84-7.80 (m, 1H), 7.47-7.39 (m, 1H), 7.35 (s, 1H), 5.87 (q, J = 25 Hz, 1H), 5.55 (q, J = 10 Hz, 1H), 4.30 (t, J = 5 Hz, 2H), 2.93-2.89 (m, 2H), 2.23 (s, 2H), 2.02-1.97 (m, 2H), 1.79-1.72 (m, 6H), 1.53-1.43 (m, 2H). |
| 41 | 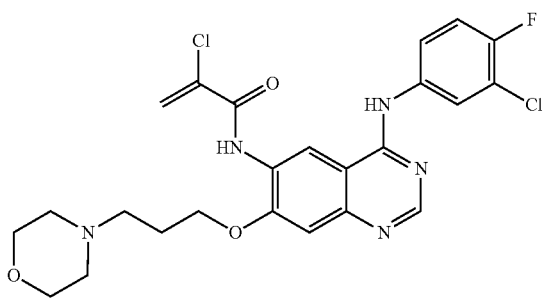 [SMILES: C=C(Cl)C(=O)Nc1cc2c(Nc3ccc(F)c(Cl)c3)ncnc2cc1OCCCN1CCOCC1] | N-[4-(3-chloro-4-fluoro-phenylamino)-7-(3-morpholin-4-yl-propoxy)-quinazolin-6-yl]-2-chloro-acrylamide<br>$^1$H NMR (500 MHz, DMSO) δ 9.86 (s, 1H), 9.75 (s, 1H), 8.80 (s, 1H), 8.57 (s, 1H), 8.16-8.14 (m, 1H), 7.83-7.79 (m, 1H), 7.43 (t, J = 9.1 Hz, 1H), 7.32 (s, 1H), 6.59 (d, J = 2.0 Hz, 1H), 6.19 (d, J = 2.1 Hz, 1H), 4.27 (t, J = 5.7 Hz, 2H), 3.59 (s, 5H), 2.39 (s, 4H), 1.99-1.94 (m, 2H), 1.23 (s, 1H). |
| 42 | 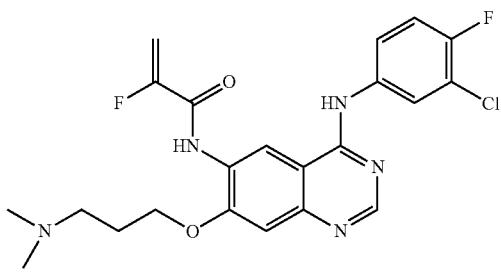 [SMILES: C=C(F)C(=O)Nc1cc2c(Nc3ccc(F)c(Cl)c3)ncnc2cc1OCCCN(C)C] | N-[4-(3-chloro-4-fluoro-phenylamino)-7-(3-dimethylamino-propoxy)-quinazolin-6-yl]-2-fluoro-acrylamide<br>$^1$H NMR (300 MHz, DMSO) δ 9.86 (s, 1H), 8.72s, 1H), 8.58 (s, 1H), 8.18 (d, J = 2.0 Hz, 1H), 7.81 (m, 1H), 7.46 (t, J = 3 Hz, 1H), 7.32 (s, 1H), 5.84 (q, J = 18 Hz, 1H), 5.53 (q, J = 2 Hz, 1H), 4.27 (t, J = 2 Hz, 2H), 281 (s, 2H), 2.45 (s, 6H), 2.06-1.99 (m, 2H). |

-continued

| Example | Structure | Name and Identification data |
|---|---|---|
| 43 | 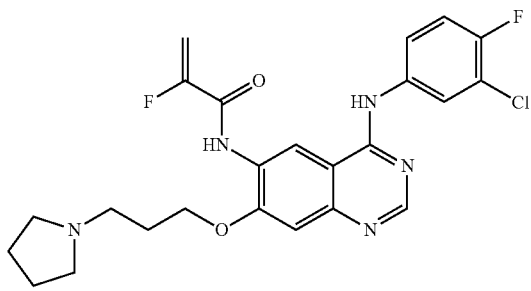 [SMILES: C=C(F)C(=O)Nc1cc2c(Nc3ccc(F)c(Cl)c3)ncnc2cc1OCCCN1CCCC1] | N-[4-(3-chloro-4-fluoro-phenylamino)-7-(3-pyrrolidin-1-yl-propoxy)-quinazolin-6-yl]-2-fluoro-acrylamide<br>1H NMR (300 MHz, CDCl3) δ 9.02 (s, 1H), 8.95 (s, 1H), 8.84 (d, J = 5 Hz, 1H), 8.63 (d, 1H), 7.95-7.91 (m, 1H), 7.55-7.52 (m, 1H), 7.17-7.11 (m, 1H), 5.90 (q, J = 45 Hz, 1H), 5.39-5.32 (m, 1H), 4.34 (t, J = 5 Hz, 2H), 2.84 (s, 1H), 2.59-2.50 (m, 2H), 2.39-2.35 (t, 1H), 2.22 (t, 2H), 2.05-1.98 (m, 2H), 1.66-1.61 (m, 4H) |
| 44 | 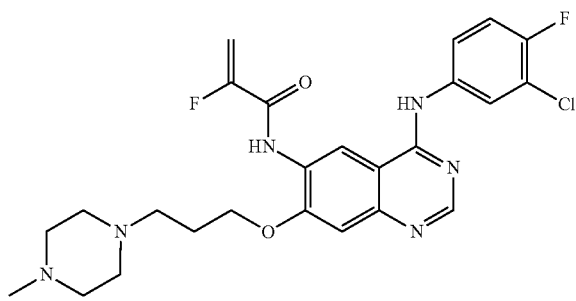 [SMILES: C=C(F)C(=O)Nc1cc2c(Nc3ccc(F)c(Cl)c3)ncnc2cc1OCCCN1CCN(C)CC1] | N-{4-(3-chloro-4-fluoro-phenylamino)-7-[3-(4-methyl-piperazin-1-yl)-propoxy]-quinazolin-6-yl}-2-fluoro-acrylamide<br>1H NMR (300 MHz, CDCl3) δ 9.01 (s, 1H), 8.97 (d, J = 5 Hz, 1H), 8.66 (s, 1H), 7.96 (q, J = 7 Hz 1H), 7.71 (s, 1H), 7.57-7.53 (m, 1H), 7.29 (s, 1H), 7.18 (t, J = 10, 1H), 5.88 (q, J = 12 Hz, 1H), 5.37 (q, J = 10 Hz, 1H), 4.30 (t, J = 7 Hz, 2H), 2.84 (s, 1H), 2.74 (s, 1H), 2.66-2.61 (m, 4H), 2.44 (s, 3H), 2.23-2.20 (m, 1H), 2.16-2.11 (m, 2H), 2.01-2.00 (m, 2H). |
| 45 | 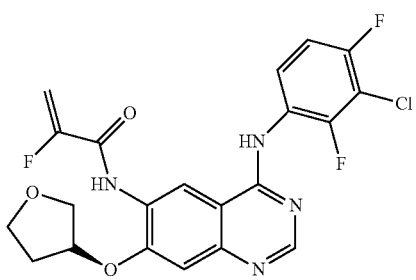 | (R)-N-[4-(3-chloro-2,4-difluoro-phenylamino)-7-(tetrahydrofuran-3-ylmethoxy)-quinazolin-6-yl]-2-fluoro-acrylamide<br>1H NMR (300 MHz, CD3Cl) δ: 2.25 (m, 1H), 2.43 (m, 1H), 4.04 (m, 4H), 5.20 (m, 1H), 5.35 (dd, 1H, J1 = 2.7 Hz, J2 = 11.4 Hz), 5.88 (dd, 1H, J1 = 2.7 Hz, J2 = 35.7 Hz), 7.04 (m, 1H), 7.65 (s, 1H), 8.13 (m, 1H), 8.65 (m, 1H), 8.91 (d, 1H, J = 3.6 Hz), 9.10 (s, 1H). |
| 46 | 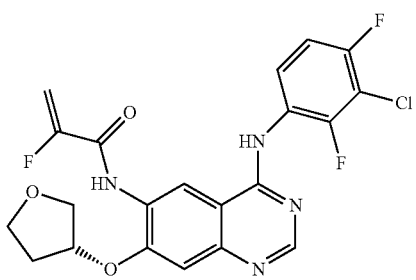 | (S)-N-[4-(3-chloro-2,4-difluoro-phenylamino)-7-(tetrahydrofuran-3-ylmethoxy)-quinazolin-6-yl]-2-fluoro-acrylamide<br>1H NMR (300 MHz, CD3OD) δ: 2.23 (m, 1H), 2.43 (m, 1H), 3.93 (m, 4H), 5.31 (m, 1H), 5.40 (dd, 1H, J1 = 2.7 Hz, J2 = 11.4 Hz), 5.82 (dd, 1H, J1 = 2.7 Hz, J2 = 35.7 Hz), 7.17 (m, 1H), 7.54 (m, 1H), 8.38 (m, 1H), 8.91 (s, 1H, J = 3.6 Hz). |
| 47 | 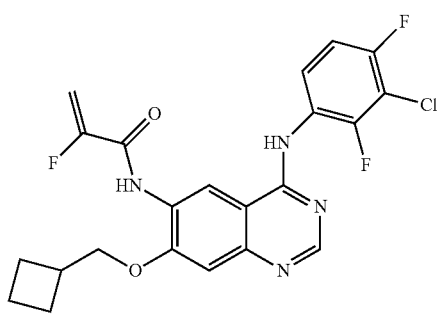 [SMILES: C=C(F)C(=O)Nc1cc2c(Nc3ccc(F)c(Cl)c3F)ncnc2cc1OCC1CCC1] | N-[4-(3-chloro-2,4-difluoro-phenylamino)-7-cyclobutylmethoxy-quinazolin-6-yl]-2-fluoro-acrylamide<br>¹H NMR (300 MHz, CD3Cl) δ: 1.99 (m, 4H), 2.22 (m, 2H), 2.93 (m, 1H), 4.19 (d, 2H, J = 4.8 Hz), 5.33 (dd, 1H, J1 = 2.7 Hz, J2 = 11.1 Hz), 5.88 (dd, 1H, J1 = 2.7 Hz, J2 = 35.7 Hz), 7.02 (m, 1H), 7.41 (s, 1H), 7.67 (s, 1H), 8.11 (m, 1H), 8.63 (s, 1H), 9.04 (m, 2H). |

| Example | Structure | Name and Identification data |
|---|---|---|
| 48 | 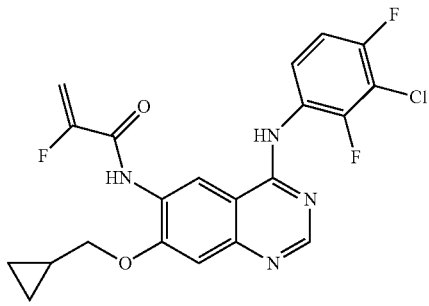 [SMILES: C=C(F)C(=O)Nc1cc2c(Nc3ccc(F)c(Cl)c3F)ncnc2cc1OCC1CC1] | N-[4-(3-chloro-2,4-difluoro-phenylamino)-7-cyclopropylmethoxy-quinazolin-6-yl]-2-fluoro-acrylamide<br>1H NMR (300 MHz, CD3Cl) δ: 0.45 (d, 2H, J = 2.1 Hz), 0.74 (d, 2H, J = 5.4 Hz), 1.25 (m, 1H), 4.07 (d, 2H, J = 5.1 Hz), 5.34 (dd, 1H, J1 = 2.7 Hz, J2 = 11.1 Hz), 5.88 (dd, 1H, J1 = 2.7 Hz, J2 = 35.7 Hz), 7.01 (m, 1H), 7.24 (s, 1H), 7.70 (s, 1H), 8.09 (m, 1H), 8.62 (s, 1H), 9.06 (m, 2H). |
| 49 | 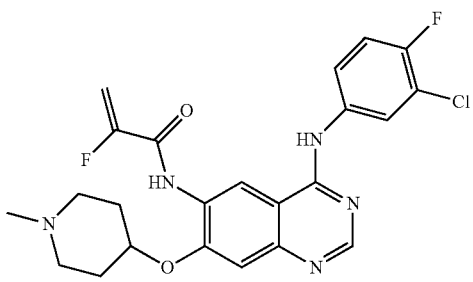 [SMILES: C=C(F)C(=O)Nc1cc2c(Nc3ccc(F)c(Cl)c3)ncnc2cc1OC1CCN(C)CC1] | N-[4-(3-chloro-4-fluoro-phenylamino)-7-(1-methyl-piperidin-4-yloxy)-quinazolin-6-yl]-2-fluoro-acrylamide<br>$^1$H NMR (300 MHz, d-DMSO) δ: 1.96 (m, 2H), 2.09 (m, 2H), 2.42 (s, 3H), 2.85 (m, 4H), 4.9 (m, 1H), 5.53 (d, 1H, J = 11.7 Hz), 5.83 (d, 1H, J = 36.3 Hz), 7.41 (m, 2H), 7.85 (s, 1H), 8.19 (m, 1H), 8.57 (s, 1H), 8.77 (s, 1H), 9.97 (s, 2H). |
| 50 | 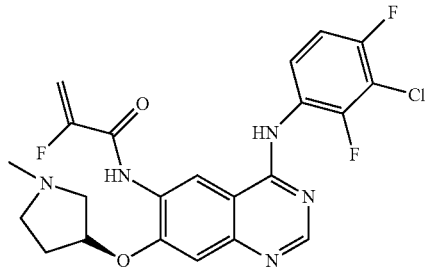 | (R)-N-[4-(3-chloro-2,4-difluoro-phenylamino)-7-(1-methyl-pyrrolidin-3-yloxy)-quinazolin-6-yl]-2-fluoro-acrylamide<br>$^1$H NMR (300 MHz, d-DMSO) δ: 1.92 (m, 2H), 2.32 (s, 3H), 2.84 (m, 4H), 5.16 (m, 1H), 5.52 (dd, 1H, J1 = 3.6 Hz, J2 = 15 Hz), 5.79 (dd, 1H, J1 = 3.6 Hz, J2 = 46.8 Hz), 7.47 (m, 2H), 8.44 (s, 1H), 8.77 (s, 1H), 9.73 (s, 1H), 9.96 (s, 1H). |
| 51 | 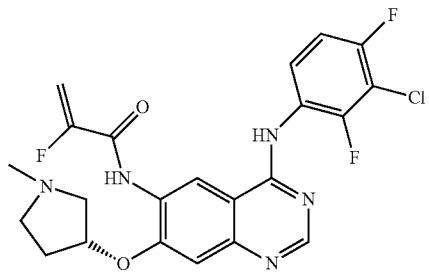 | (S)-N-[4-(3-chloro-2,4-difluoro-phenylamino)-7-(1-methyl-pyrrolidin-3-yloxy)-quinazolin-6-yl]-2-fluoro-acrylamide<br>$^1$H NMR (300 MHz, d-DMSO) δ: 2.15 (m, 2H), 2.52 (s, 3H), 2.84 (m, 2H), 3.16 (m, 2H), 5.22 (m, 1H), 5.4 (dd, 1H, J1 = 3.6 Hz, J2 = 15 Hz), 5.82 (dd, 1H, J1 = 3.6 Hz, J2 = 46.8 Hz), 7.19 (m, 2H), 7.52 (m, 1H), 8.34 (s, 1H), 8.91 (s, 1H). |
| 52 | 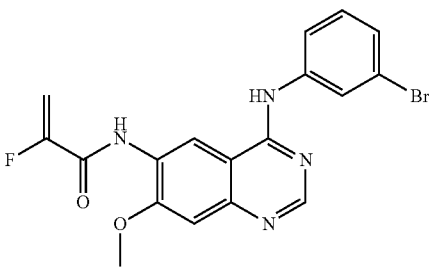 [SMILES: C=C(F)C(=O)Nc1cc2c(Nc3cccc(Br)c3)ncnc2cc1OC] | N-[4-(3-bromo-phenylamino)-7-methoxy-quinazolin-6-yl]-2-fluoro-acrylamide<br>$^1$H NMR (500 MHz, DMSO) δ 9.88 (s, 1H), 9.82 (s, 1H), 8.73 (s, 1H), 8.61 (s, 1H), 8.19 (s, 1H), 7.89 (d, J = 8.0 Hz, 1H), 7.36-7.33 (m, 2H), 7.30-7.28 (m, 1H), 5.78 (dd, J = 48.0, 3.5 Hz, 1H), 5.51 (dd, J = 15.5, 3.5 Hz, 1H), 4.00 (s, 3H).<br>HRMS (EI): [M + H]+ = 417.0343. |

| Example | Structure | Name and Identification data |
|---|---|---|
| 53 | 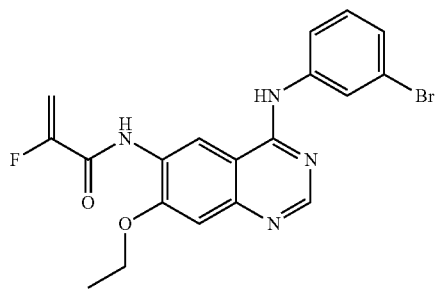 [SMILES: C=C(F)C(=O)Nc1cc2c(Nc3cccc(Br)c3)ncnc2cc1OCC] | N-[4-(3-bromo-phenylamino)-7-ethoxy-quinazolin-6-yl]-2-fluoro-acrylamide<br>$^1$H NMR (500 MHz, DMSO) δ 9.82 (s, 1H), 9.76 (s, 1H), 8.76 (s, 1H), 8.59 (s, 1H), 8.19 (s, 1H), 7.88 (d, J = 8.0 Hz, 1H), 7.32 (m, 3H), 5.78 (dd, J = 48.0, 2.5 Hz, 1H), 5.52 (dd, J = 16.0, 3.0 Hz, 1H), 4.27 (q, 2H), 1.42 (t, 3H).<br>HRMS (EI): [M + H]+ = 431.0499. |
| 54 | 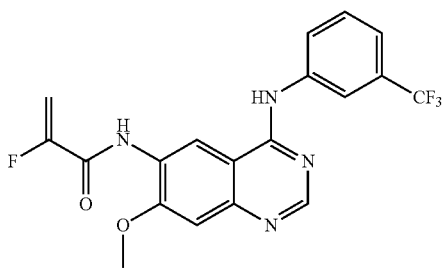 [SMILES: C=C(F)C(=O)Nc1cc2c(Nc3cccc(C(F)(F)F)c3)ncnc2cc1OC] | N-[7-methoxy-4-(3-trifluoromethyl-phenylamino)-quinazolin-6-yl]-2-fluoro-acrylamide<br>$^1$H NMR (500 MHz, DMSO) δ 9.96 (s, 1H), 9.87 (s, 1H), 8.76 (s, 1H), 8.62 (s, 1H), 8.28 (s, 1H), 8.24 (d, J = 8.5 Hz, 1H), 7.45-7.36 (m, 3H), 5.78 (dd, J = 47.5, 3.5 Hz, 1H), 5.51 (dd, J = 15.5, 4.0 Hz, 1H), 4.01 (s, 3H).<br>HRMS (EI): [M + H]+ = 407.1087. |
| 55 | 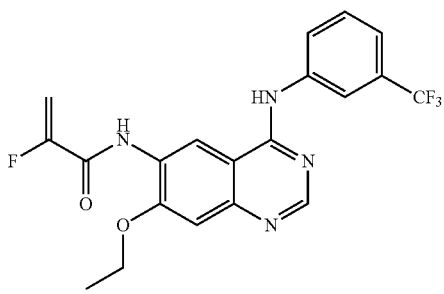 [SMILES: C=C(F)C(=O)Nc1cc2c(Nc3cccc(C(F)(F)F)c3)ncnc2cc1OCC] | N-[7-ethoxy-4-(3-trifluoromethyl-phenylamino)-quinazolin-6-yl]-2-fluoro-acrylamide<br>$^1$H NMR (500 MHz, DMSO) δ 10.00 (s, 1H), 9.80 (s, 1H), 8.84 (s, 1H), 8.65 (s, 1H), 8.33 (s, 1H), 8.28 (d, J = 8.0 Hz, 1H), 7.68-7.65 (m, 1H), 7.50-7.48 (d, 1H), 7.37 (s, 1H), 5.83 (dd, J = 48.0, 3.5 Hz, 1H), 5.56 (dd, J = 15.5, 3.5 Hz, 1H), 4.33 (q, 2H), 1.48 (t, 3H).<br>HRMS (EI): [M + H]+ = 421.1294. |
| 56 | 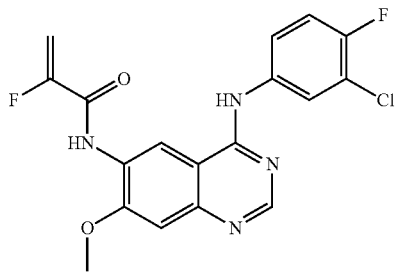 [SMILES: C=C(F)C(=O)Nc1cc2c(Nc3ccc(F)c(Cl)c3)ncnc2cc1OC] | N-[4-(3-chloro-4-fluoro-phenylamino)-7-methoxy-quinazolin-6-yl]-2-fluoro-acrylamide<br>$^1$H NMR (500 MHz, DMSO) δ 9.85 (s, 2H), 8.71 (s, 1H), 8.59 (s, 1H), 8.17-8.15 (m, 1H), 7.83-7.80 (m, 1H), 7.44 (t, J = 9.1 Hz, 1H), 7.34 (s, 1H), 5.78 (dd, J = 48.0, 3.8 Hz, 1H), 5.51 (dd, J = 15.7, 3.7 Hz, 1H), 4.01 (s, 3H). |
| 57 | 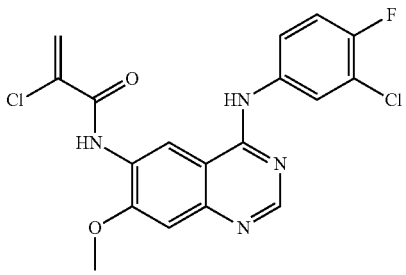 | N-[4-(3-chloro-4-fluoro-phenylamino)-7-methoxy-quinazolin-6-yl]-2-chloro-acrylamide<br>$^1$H NMR (500 MHz, DMSO) δ 9.85 (s, 1H), 9.81 (s, 1H), 8.76 (s, 1H), 8.58 (s, 1H), 8.17-8.15 (m, 1H), 7.83-7.80 (m, 1H), 7.44 (t, J = 9.1 Hz, 1H), 7.34 (s, 1H), 6.59 (d, J = 2.3 Hz, 1H), 6.18 (d, J = 2.4 Hz, 1H), 4.02 (s, 3H).<br>HRMS (EI): [M + H]$^+$ = 437.0994. |

| Example | Structure | Name and Identification data |
|---|---|---|
| 58 | 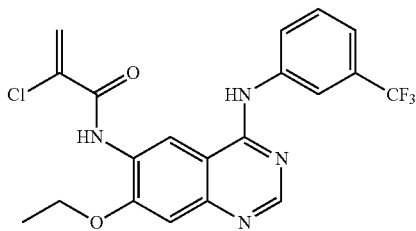 [SMILES: C=C(Cl)C(=O)Nc1cc2c(Nc3cccc(C(F)(F)F)c3)ncnc2cc1OCC] | N-[7-ethoxy-4-(3-trifluoromethyl-phenylamino)-quinazolin-6-yl]-2-chloro-acrylamide<br>$^1$H NMR (500 MHz, DMSO) δ 9.98 (s, 1H), 9.75 (s, 1H), 8.86 (s, 1H), 8.60 (s, 1H), 8.27 (s, 1H), 8.22 (d, J = 8.5 Hz, 1H), 7.62 (t, J = 7.8 Hz, 1H), 7.44 (d, J = 7.3 Hz, 1H), 7.34 (s, 1H), 6.60 (s, 1H), 6.19 (s, 1H), 4.30 (q, J = 6.0 Hz, 2H), 1.44 (t, J = 6.4 Hz, 3H). |
| 59 | 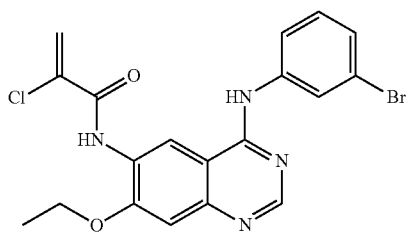 [SMILES: C=C(Cl)C(=O)Nc1cc2c(Nc3cccc(Br)c3)ncnc2cc1OCC] | N-[4-(3-bromo-phenylamino)-7-ethoxy-quinazolin-6-yl]-2-chloro-acrylamide<br>$^1$H NMR (500 MHz, DMSO) δ 9.84 (s, 1H), 9.74 (s, 1H), 8.84 (s, 1H), 8.58 (s, 1H), 8.17 (t, J = 1.9 Hz, 1H), 7.89-7.86 (m, 1H), 7.36-7.32 (m, 2H), 7.29-7.27 (m, 1H), 6.60 (d, J = 2.3 Hz, 1H), 6.19 (d, J = 2.3 Hz, 1H), 4.29 (q, J = 6.9 Hz, 2H), 1.44 (t, J = 6.9 Hz, 3H). |
| 60 | 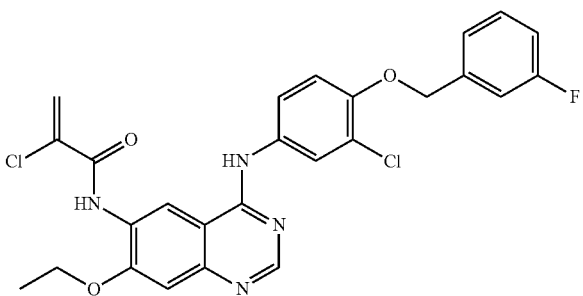 [SMILES: C=C(Cl)C(=O)Nc1cc2c(Nc3ccc(OCc4cccc(F)c4)c(Cl)c3)ncnc2cc1OCC] | N-{4-[3-chloro-4-(3-fluoro-benzyloxy)-phenylamino]-7-ethoxy-quinazolin-6-yl}-2-chloro-acrylamide<br>$^1$H NMR (500 MHz, DMSO) δ 9.79 (s, 1H), 9.78 (s, 1H), 8.85 (s, 1H), 8.57 (s, 1H), 8.04 (d, J = 2.5 Hz, 1H), 7.76 (dd, J = 9.0, 2.5 Hz, 1H), 7.53 (dd, J = 14.1, 8.1 Hz, 1H), 7.38 (t, J = 9.1 Hz, 2H), 7.35 (s, 1H), 7.31 (d, J = 9.0 Hz, 1H), 7.27-7.22 (m, 1H), 6.65 (d, J = 2.2 Hz, 1H), 6.24 (d, J = 2.3 Hz, 1H), 5.31 (s, 2H), 4.34 (q, J = 6.9 Hz, 2H), 1.49 (t, J = 6.9 Hz, 3H).<br>HRMS (EI): [M + H]$^+$ = 527.1049. |
| 61 | 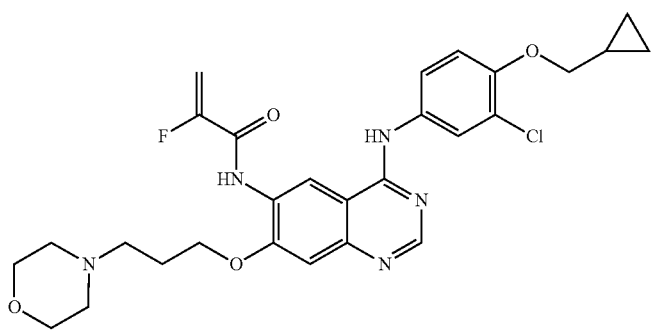 [SMILES: C=C(F)C(=O)Nc1cc2c(Nc3ccc(OCC4CC4)c(Cl)c3)ncnc2cc1OCCCN1CCOCC1] | N-[4-(3-chloro-4-cyclopropylbenzyloxy-phenylamino)-7-(3-morpholin-4-yl-propoxy)-quinazolin-6-yl]-2-fluoro-acrylamide<br>$^1$H NMR (500 MHz, DMSO) δ 9.74 (s, 1H), 9.68 (s, 1H), 8.69 (s, 1H), 8.52 (s, 1H), 7.97 (d, J = 2.3 Hz, 1H), 7.69 (dd, J = 8.9, 2.3 Hz, 1H), 7.28 (s, 1H), 7.14 (d, J = 9.0 Hz, 1H), 5.76 (dd, J = 48.1, 3.5 Hz, 1H), 5.51 (dd, J = 15.6, 3.6 Hz, 1H), 4.23 (t, J = 5.7 Hz, 2H), 3.92 (d, J = 6.8 Hz, 2H), 3.58 (t, J = 3.8 Hz, 41-), 2.46 (t, J = 7.0 Hz, 2H), 2.37 (s, 4H), 1.99-1.90 (m, 2H), 1.30-1.22 (m, 1H), 0.61-0.58 (m, 2H), 0.37-0.36 (m, 2H).<br>$^{13}$C NMR (126 MHz, DMSO) δ 158.34, 157.45, 156.15, 155.42, 155.16, 150.63, 150.45, 133.43, 126.05, 124.27, 122.54, 121.28, 119.13, 114.55, 109.10, 108.09, 100.55 (d, J = 14.6 Hz), 73.82, 67.35, 66.67, 55.11, 53.83, 25.98, 10.58, 3.56.<br>HRMS (EI): [M + H]$^+$ = 556.2121. |
| 62 | 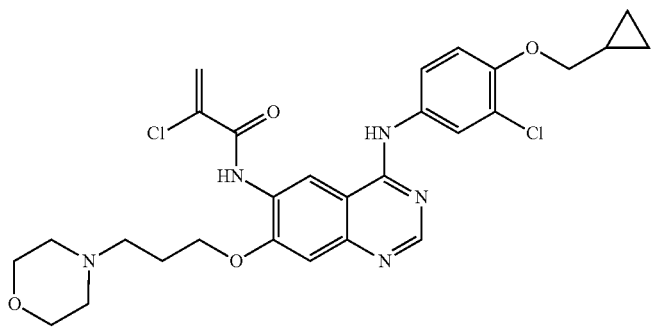 [SMILES: C=C(Cl)C(=O)Nc1cc2c(Nc3ccc(OCC4CC4)c(Cl)c3)ncnc2cc1OCCCN1CCOCC1] | N-[4-(3-chloro-4-cyclopropylbenzyloxy-phenylamino)-7-(3-morpholin-4-yl-propoxy)-quinazolin-6-yl]-2-chloro-acrylamide<br>$^1$H NMR (500 MHz, DMSO) 3 9.72 (s, 1H), 9.70 (s, 1H), 8.77 (s, 1H), 8.51 (s, 1H), 7.96 (d, J = 2.6 Hz, 1H), 7.69 (dd, J = 9.0, 2.6 Hz, 1H), 7.28 (s, 1H), 7.14 (d, J = 9.0 Hz, 1H), 6.59 (d, J = 2.3 Hz, 1H), 6.18 (d, J = 2.3 Hz, 1H), 4.25 (t, J = 6.0 Hz, 2H), 3.92 (d, J = 6.9 Hz, 2H), 3.58 (t, J = 4.5 Hz, 4H), 2.50-2.46 (m, 2H), 2.38 (s, 4H), 2.00-1.93 (m, 2H), 1.30-1.24 (m, 1H), 0.62-0.57 (m, 2H), 0.38-0.34 (m, 2H). |

| Example | Structure | Name and Identification data |
|---|---|---|
| 63 | 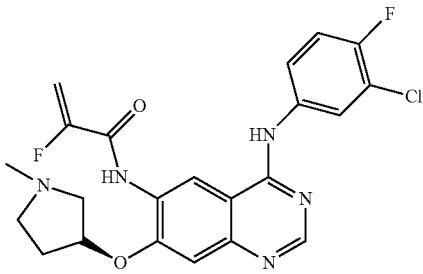 | (R)-N-[4-(3-chloro-4-fluoro-phenylamino)-7-(1-methyl-pyrrolidin-3-yloxy)-quinazolin-6-yl]-2-fluoro-acrylamide<br>$^1$H NMR (500 MHz, DMSO) δ 9.86 (s, 1H), 9.79 (s, 1H), 8.76 (s, 1H), 8.57 (s, 1H), 8.16 (dd, $J_1$ = 7.5 Hz, $J_2$ = 2.5 Hz, 1H), 7.81 (ddd, $J_1$ = 9.0 Hz, $J_2$ = 4.0 Hz, $J_3$ = 2.5 Hz, 1H), 7.43 (t, J = 9.0 Hz, 1H), 7.26 (s, 1H), 5.78 (dd, $J_1$ = 48.0 Hz, $J_2$ = 3.5 Hz, 1H), 5.52 (dd, $J_1$ = 16.0 Hz, $J_1$ = 4.0 Hz, 1H), 5.17 (m, 1H), 2.96-2.93 (m, 1H), 2.84 (m, 2H), 2.44-2.39 (m, 2H), 2.36 (s, 3H), 1.95-1.91 (m, 1H).<br>HRMS (ESI): m/zcalcd for $(C_{22}H_{20}ClF_2N_5O_2 + H)^+$: 460.1352; found: 546.1704. |
| 64 | 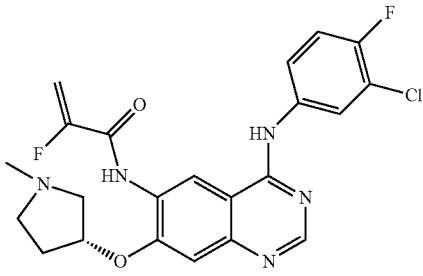 [SMILES: C=C(F)C(=O)Nc1cc2c(Nc3ccc(F)c(Cl)c3)ncnc2cc1O[C@@H]1CCN(C)C1] | (S)-N-[4-(3-chloro-4-fluoro-phenylamino)-7-(1-methyl-pyrrolidin-3-yloxy)-quinazolin-6-yl]-2-fluoro-acrylamide<br>$^1$H NMR (500 MHz, DMSO) δ 9.84 (s, 1H), 9.76 (s, 1H), 8.76 (s, 1H), 8.56 (s, 1H), 8.15 (dd, $J_1$ = 7.0 Hz, $J_2$ = 3.0 Hz, 1H), 7.82-7.79 (m, 1H), 7.43 (t, J = 9.0 Hz, 1H), 7.24 (s, 1H), 5.77 (dd, $J_1$ = 48.0 Hz, $J_2$ = 3.5 Hz, 1H), 5.52 (dd, $J_1$ = 15.5 Hz, $J_2$ = 3.5 Hz, 1H), 5.13 (s, 1H), 2.87-2.83 (m, 1H), 2.75-2.71 (m, 2H), 2.41-2.37 (m, 2H), 2.29 (s, 3H), 1.90-1.86 (m, 1H).<br>HRMS (ESI): m/zcalcd for $(C_{22}H_{20}ClF_2N_5O_2 + H)^+$: 460.1352; found: 460.1355. |
| 65 | 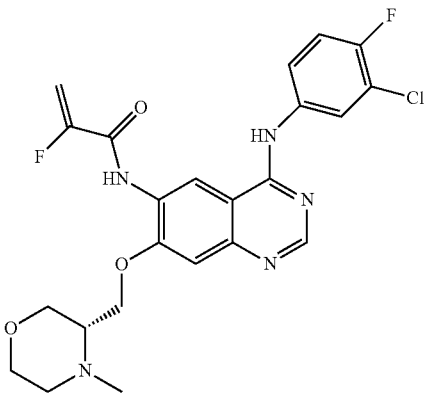 [SMILES: C=C(F)C(=O)Nc1cc2c(Nc3ccc(F)c(Cl)c3)ncnc2cc1OC[C@H]1COCCN1C] | (R)-N-[4-(3-chloro-4-fluoro-phenylamino)-7-(4-methyl-morpholin-3-ylmethoxy)-quinazolin-6-yl]-2-fluoro-acrylamide<br>$^1$H NMR (500 MHz, DMSO) δ 9.85 (s, 1H), 9.83 (s, 1H), 8.72 (s, OH), 8.59 (s, 1H), 8.17 (dd, $J_1$ = 6.5 Hz, $J_2$ = 2.5 Hz, 1H), 7.82-7.80 (m, 1H), 7.44 (t, J = 9.0 Hz, 1H), 7.40 (s, Hi), 5.81 (d, J = 3.5 Hz, 1H), 5.71 (d, J = 3.5 Hz, 1H), 5.52 (dd, $J_1$ = 15.5 Hz, $J_2$ = 3.5 Hz, 1H), 4.35 (dd, $J_1$ = 10.5 Hz, $J_2$ = 4.0 Hz, 1H), 4.17-4.16 (m, 1H), 3.90 (d, J = 9.0 Hz, 1H), 3.73 (d, J = 11.5 Hz, 1H), 3.52 (d, J = 10.0 Hz, 1H), 3.42-3.38 (m, 3H), 2.75-2.73 (m, 1H), 2.33 (s, 3H).<br>HRMS (ESI): m/z calcd for $(C_{23}H_{22}ClF_2N_5O_3 + H)^+$: 490.1457; found: 490.1451. |
| 66 | 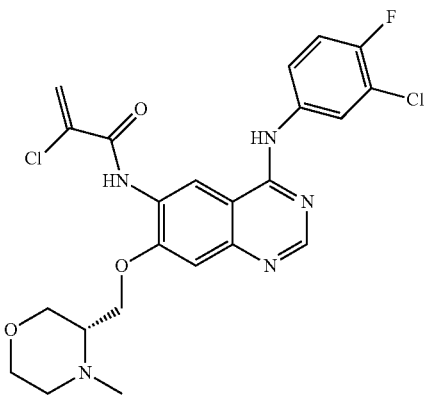 [SMILES: C=C(Cl)C(=O)Nc1cc2c(Nc3ccc(F)c(Cl)c3)ncnc2cc1OC[C@H]1COCCN1C] | (R)-N-[4-(3-chloro-4-fluoro-phenylamino)-7-(4-methyl-morpholin-3-ylmethoxy)-quinazolin-6-yl]2-chloro-acrylamide<br>$^1$H NMR (500 MHz, DMSO) δ 9.93 (s, 1H), 9.82 (s, 1H), 8.86 (s, 1H), 8.64 (s, 1H), 8.21 (dd, $J_1$ = 6.5 Hz, $J_2$ = 2.0 Hz, 1H), 7.88-7.85 (m, 1H), 7.49 (t, J = 9.0 Hz, 1H), 7.45 (s, 1H), 6.64 (d, J = 2.0 Hz, 1H), 6.25 (d, J = 2.0 Hz, 1H), 4.41 (dd, $J_1$ = 10.0 Hz, $J_2$ = 4.0 Hz, 1H), 4.25-4.22 (m, 1H), 3.96 (dd, $J_1$ = 11.0 Hz, $J_2$ = 2.5 Hz, 1H), 3.78 (d, J = 11.0 Hz, 1H), 3.57 (t, J = 9.0 Hz, 1H), 3.49 (t, J = 10.5 Hz, 1H), 2.76 (d, J = 12.0 Hz, 1H), 2.38 (s, 3H), 2.32 (t, J = 9.5 Hz, 1H).<br>HRMS (ESI): m/zcalcd for $(C_{23}H_{22}Cl_2FN_5O_3 + H)^+$: 506.1162; found: 506.1162. |

-continued

| Example | Structure | Name and Identification data |
|---|---|---|
| 67 | 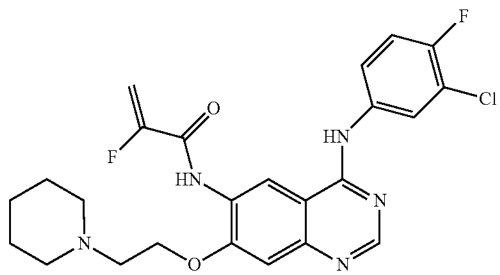 [SMILES: C=C(F)C(=O)Nc1cc2c(Nc3ccc(F)c(Cl)c3)ncnc2cc1OCCN1CCCCC1] | N-[4-(3-chloro-4-fluoro-phenylamino)-7-(2-piperidin-1-yl-ethoxy)-quinazolin-6-yl]-2-fluoro-acrylamide<br>HRMS (ESI): m/z calcd for $(C_{24}H_{24}ClF_2N_5O_2 + H)^+$: 488.1665; found: 488.1665. |
| 68 | 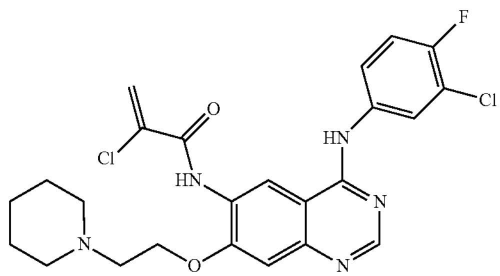 [SMILES: C=C(Cl)C(=O)Nc1cc2c(Nc3ccc(F)c(Cl)c3)ncnc2cc1OCCN1CCCCC1] | N-[4-(3-chloro-4-fluoro-phenylamino)-7-(2-piperidin-1-yl-ethoxy)-quinazolin-6-yl]-2-chloro-acrylamide<br>HRMS (ESI): m/z calcd for $(C_{24}H_{24}Cl_2FN_5O_2 + H)^+$: 504.1369; found: 504.1361. |
| 69 | 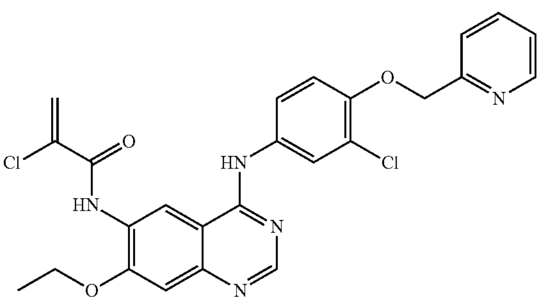 [SMILES: C=C(Cl)C(=O)Nc1cc2c(Nc3ccc(OCc4ccccn4)c(Cl)c3)ncnc2cc1OCC] | 2-chloro-N-{4-[3-chloro-4-(pyridin-2-ylmethoxy)-phenylamino]-7-ethoxy-quinazolin-6-yl}-acrylamide<br>HRMS (ESI): m/z calcd for $(C_{25}H_{21}Cl_2N_5O_3 + H)^+$: 510.1100; found: 510.1091. |
| 70 | 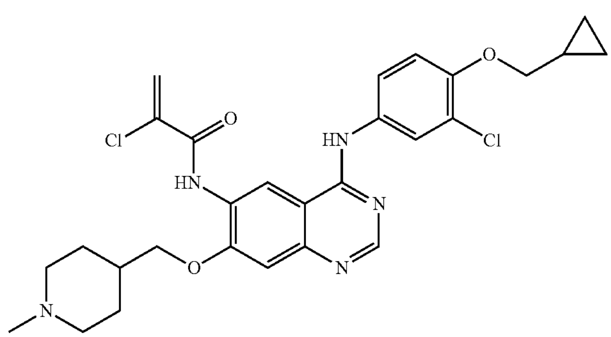 [SMILES: C=C(Cl)C(=O)Nc1cc2c(Nc3ccc(OCC4CC4)c(Cl)c3)ncnc2cc1OCC1CCN(C)CC1] | 2-chloro-N-[4-(3-chloro-4-cyclopropylmethoxy-phenylamino)-7-(1-methyl-piperidin-4-ylmethoxy)-quinazolin-6-yl]-acrylamide<br>HRMS (ESI): m/z calcd for $(C_{28}H_{32}Cl_2N_5O_3 + H)^+$: 556.1882; found: 556.1875. |
| 71 | 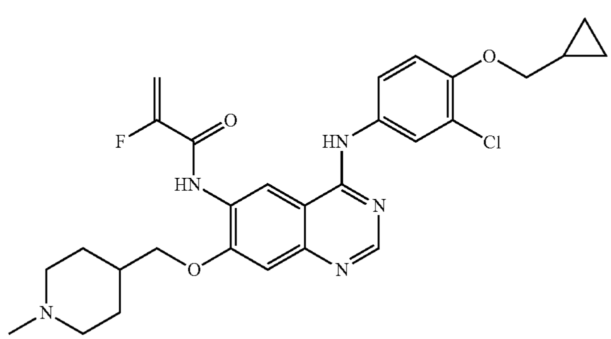 [SMILES: C=C(F)C(=O)Nc1cc2c(Nc3ccc(OCC4CC4)c(Cl)c3)ncnc2cc1OCC1CCN(C)CC1] | N-[4-(3-chloro-4-cyclopropylmethoxy-phenylamino)-7-(1-methyl-piperidin-4-ylmethoxy)-quinazolin-6-yl]-2-fluoro-acrylamide<br>HRMS (ESI): m/z calcd for $(C_{28}H_{31}ClFN_5O_3 + H)^+$: 540.2178; found: 540.2174. |

-continued

| Example | Structure | Name and Identification data |
|---|---|---|
| 72 | 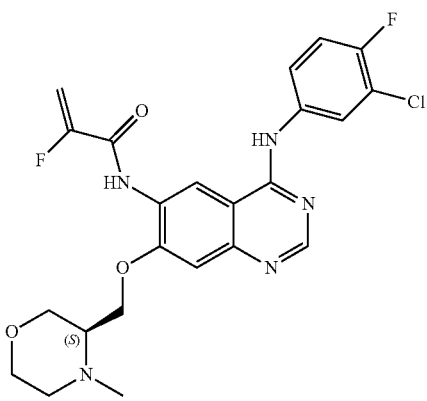 | (S)-N-[4-((3-chloro-4-fluoro-phenyl)amino)-7-((4-methyl-morpholin-3-yl)methoxy)-quinazolin-6-yl]-2-fluoro-acrylamide<br>MS (ESI$^+$): 490 [M + H]$^+$ |
| 73 | 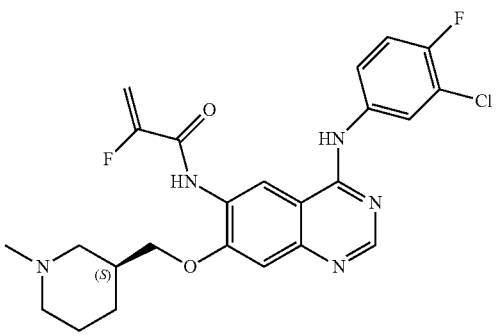 | (S)-N-[4-(3-chloro-4-fluoro-phenylamino)-7-(1-methyl-piperidin-3-ylmethoxy)-quinazolin-6-yl]-2-fluoro-acrylamide<br>MS (ESI$^+$): 488 [M + H]$^+$ |
| 74 | 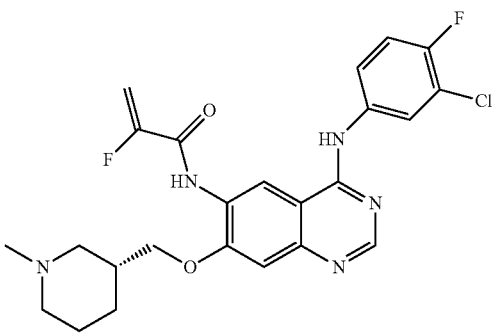 | (R)-N-[4-(3-chloro-4-fluoro-phenylamino)-7-(1-methyl-piperidin-3-ylmethoxy)-quinazolin-6-yl]-2-fluoro-acrylamide<br>MS (ESI$^+$): 488 [M + H]$^+$ |
| 75 | 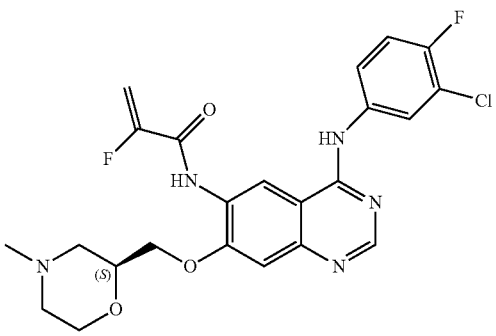 | (S)-N-[4-(3-chloro-4-fluoro-phenylamino)-7-(4-methyl-morpholin-2-ylmethoxy)-quinazolin-6-yl]-2-fluoro-acrylamide<br>MS (ESI$^+$): 490 [M + H]$^+$ |

| Example | Structure | Name and Identification data |
|---|---|---|
| 76 | 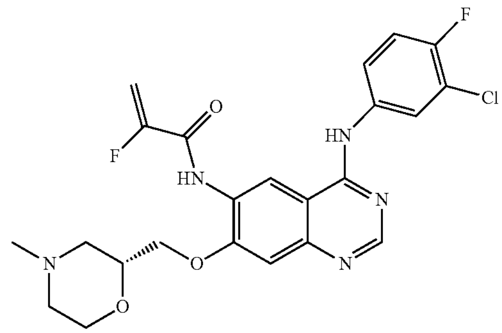 [SMILES: C=C(F)C(=O)Nc1cc2c(Nc3ccc(F)c(Cl)c3)ncnc2cc1OC[C@H]1CN(C)CCO1] | (R)-N-[4-(3-chloro-4-fluoro-phenylamino)-7-(4-methyl-morpholin-2-ylmethoxy)-quinazolin-6-yl]-2-fluoro-acrylamide<br>MS (ESI$^+$): 490 [M + H]$^+$ |
| 77 | 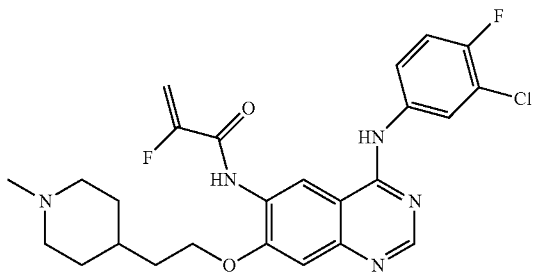 [SMILES: C=C(F)C(=O)Nc1cc2c(Nc3ccc(F)c(Cl)c3)ncnc2cc1OCCC1CCN(C)CC1] | N-{4-(3-chloro-4-fluoro-phenylamino)-7-[2-(1-methyl-piperidin-4-yl)-ethoxy]-quinazolin-6-yl}-2-fluoro-acrylamide<br>MS (ESI$^+$): 502 [M + H]$^+$ |
| 78 | 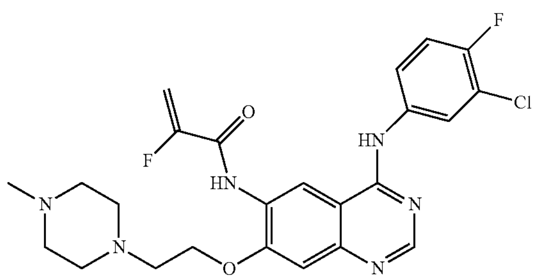 [SMILES: C=C(F)C(=O)Nc1cc2c(Nc3ccc(F)c(Cl)c3)ncnc2cc1OCCN1CCN(C)CC1] | N-{4-(3-chloro-4-fluoro-phenylamino)-7-[2-(4-methyl-piperazin-1-yl)-ethoxy]-quinazolin-6-yl}-2-fluoro-acrylamide<br>MS (ESI$^+$): 503 [M + H]$^+$ |
| 79 | 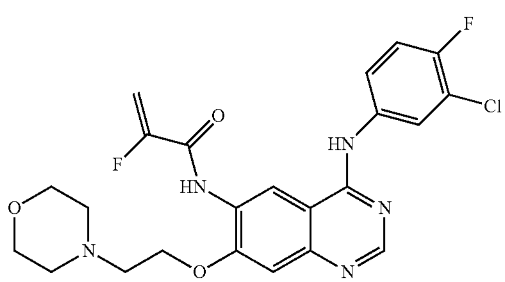 [SMILES: C=C(F)C(=O)Nc1cc2c(Nc3ccc(F)c(Cl)c3)ncnc2cc1OCCN1CCOCC1] | N-[4-(3-chloro-4-fluoro-phenylamino)-7-(2-morpholin-4-yl-ethoxy)-quinazolin-6-yl]-2-fluoro-acrylamide<br>MS (ESI$^+$): 490 [M + H]$^+$ |
| 80 | 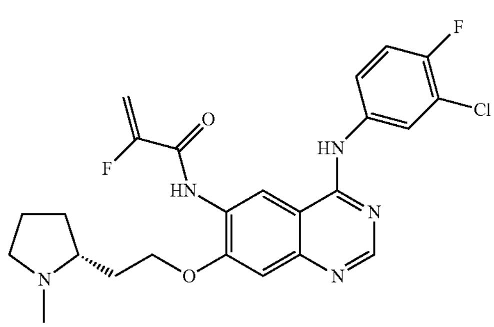 [SMILES: C=C(F)C(=O)Nc1cc2c(Nc3ccc(F)c(Cl)c3)ncnc2cc1OCC[C@H]1CCCN1C] | (R)-N-{4-(3-chloro-4-fluoro-phenylamino)-7-[2-(1-methyl-pyrrolidin-2-yl)-ethoxy]-quinazolin-6-yl}-2-fluoro-acrylamide<br>MS (ESI$^+$): 488 [M + H]$^+$ |

-continued

| Example | Structure | Name and Identification data |
|---|---|---|
| 81 | 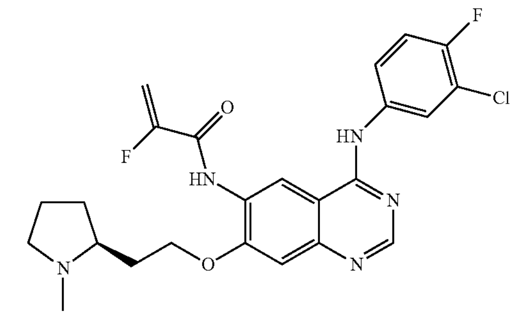 [SMILES: C=C(F)C(=O)Nc1cc2c(Nc3ccc(F)c(Cl)c3)ncnc2cc1OCC[C@@H]1CCCN1C] | (S)-N-{4-(3-chloro-4-fluoro-phenylamino)-7-[2-(1-methyl-pyrrolidin-2-yl)-ethoxy]-quinazolin-6-yl}-2-fluoro-acrylamide<br>MS (ESI+): 488 [M + H]+ |
| 82 | 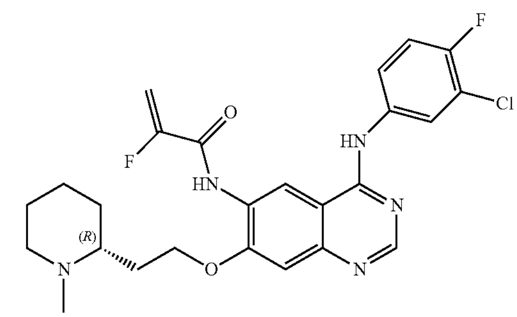 | (R)-N-{4-(3-chloro-4-fluoro-phenylamino)-7-[2-(1-methyl-piperidin-2-yl)-ethoxy]-quinazolin-6-yl}-2-fluoro-acrylamide<br>MS (ESI+): 502 [M + H]+ |
| 83 | 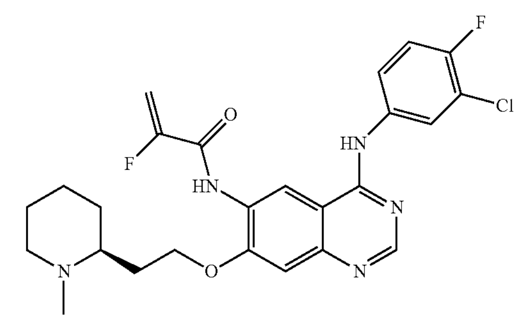 [SMILES: C=C(F)C(=O)Nc1cc2c(Nc3ccc(F)c(Cl)c3)ncnc2cc1OCC[C@@H]1CCCCN1C] | (S)-N-{4-(3-chloro-4-fluoro-phenylamino)-7-[2-(1-methyl-piperidin-2-yl)-ethoxy]-quinazolin-6-yl}-2-fluoro-acrylamide<br>MS (ESI+): 502 [M + H]+ |
| 84 | 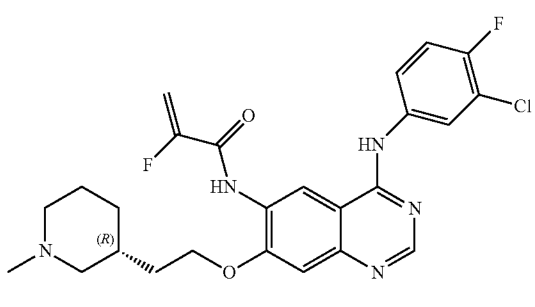 | (R)-N-{4-(3-chloro-4-fluoro-phenylamino)-7-[2-(1-methyl-piperidin-3-yl)-ethoxy]-quinazolin-6-yl}-2-fluoro-acrylamide<br>MS (ESI+): 502 [M + H]+ |
| 85 | 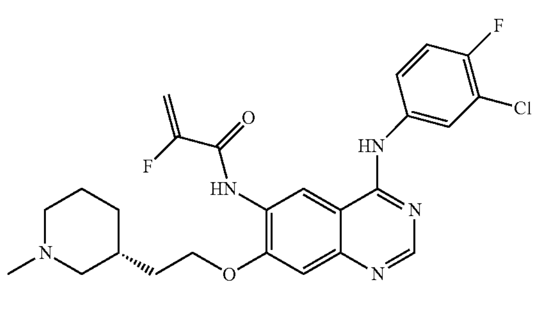 [SMILES: C=C(F)C(=O)Nc1cc2c(Nc3ccc(F)c(Cl)c3)ncnc2cc1OCC[C@H]1CCCN(C)C1] | (S)-N-{4-(3-chloro-4-fluoro-phenylamino)-7-[2-(1-methyl-piperidin-3-yl)-ethoxy]-uinazolin-6-yl}-2-fluoro-acrylamide<br>MS (ESI+): 502 [M + H]+ |

| Example | Structure | Name and Identification data |
|---|---|---|
| 86 | 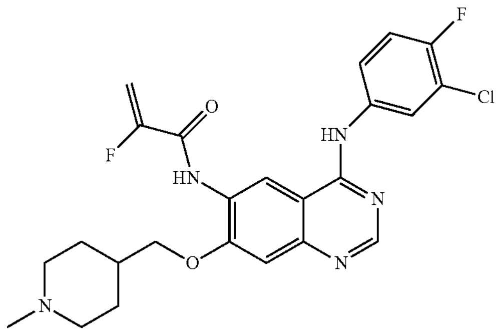 [SMILES: C=C(F)C(=O)Nc1cc2c(Nc3ccc(F)c(Cl)c3)ncnc2cc1OCC1CCN(C)CC1] | N-[4-(3-chloro-4-fluoro-phenylamino)-7-(1-methyl-piperidin-4-ylmethoxy)-quinazolin-6-yl]-2-fluoro-acrylamide<br>MS (ESI$^+$): 488 [M + H]$^+$ |
| 87 | 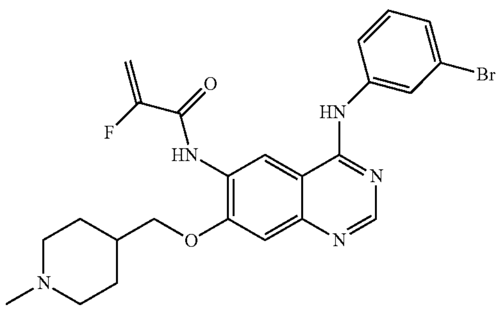 [SMILES: C=C(F)C(=O)Nc1cc2c(Nc3cccc(Br)c3)ncnc2cc1OCC1CCN(C)CC1] | N-[4-(3-bromo-phenylamino)-7-(1-methyl-piperidin-4-ylmethoxy)-quinazolin-6-yl]-2-fluoro-acrylamide<br>MS (ESI$^+$): 514, 516 [M + H]$^+$ |
| 88 | 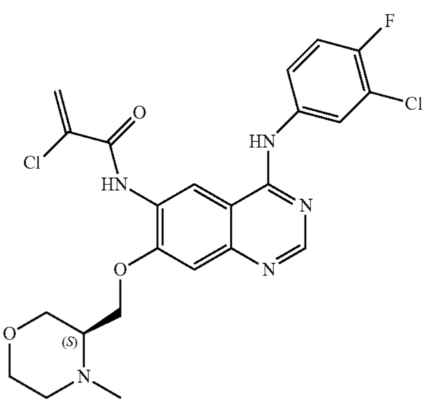 | (S)-N-[4-(3-chloro-4-fluoro-phenylamino)-7-(4-methyl-morpholin-3-ylmethoxy)-quinazolin-6-yl]-2-chloro-acrylamide<br>HRMS (ESI): m/z calcd for $(C_{23}H_{22}Cl_2FN_5O_3 + H)^+$: 506.1162; found: 506.1162. |

Formulation Example

Example 1

Capsules

| Prescription | |
|---|---|
| Example 1 compound | 100.0 g |
| Starch | 80.0 g |
| Lactose | 60.0 g |
| Microcrystalline cellulose | 35.0 g |
| Solution of 10% polyvinylpyrrolidone in ethanol | proper quantities |
| Magnesium stearate | 0.5 g |
| A total system | 1000 grains |

The active ingredient and various excipients was sieved through a 80 mesh screen, weighed according to the prescription, with solution of 10% polyvinylpyrrolidone in ethanol as binder, suitable particles were made with 16 mesh sieve, dried at 65° C., screened with 14 mesh sieve. mixed uniformly with magnesium stearate, measured particle concentration, calculated and encapsulated.

Example 2

Tablets (Powder Compression Process)

| Prescription | |
|---|---|
| Compound in Example 1 | 50 g |
| Microcrystalline cellulose | 30 g |
| Lactose anhydrous | 45 g |
| Polyvinylpyrrolidone | 3 g |
| Micro powder silica gel | 0.2 g |
| Magnesium stearate | 0.5 g |
| A total system | 1000 grains |

The active compound, microcrystalline cellulose, anhydrous lactose, polyvinylpyrrolidone, colloidal silica were mixed in mixer well uniformly, then magnesium stearate was added and mixed completely, then pressed.

Example 3

Tablets (Wet Granulating)

| Prescription | |
|---|---|
| Compound of Example 1 | 50 g |
| Lactose | 120 g |
| Microcrystalline cellulose | 40 g |
| 8% Starch slurry | q.s. |
| Carboxymethyl starch sodium | 10 g |
| Magnesium stearate | 1 g |
| A total system | 1000 grains |

The active compound, microcrystalline cellulose, lactose, and sodium carboxymethyl starch were sieved through a 80 mesh screen, mixed, and made into the softwood with 8% starch slurry, then milled granulated with 16 mesh screen, dried and granulated, then magnesium stearate was added and mixed uniformly, measured particle concentration, tablet weight was calculated, and press.

Example 4

Injection 1

| Prescription | |
|---|---|
| Each ampule containing Compound 2-1 in Example 2 | 40 mg |
| 0.01N hydrochloric acid | q.s. |
| Redistilled water | added to 10.0 ml |

Preparation: Dissolve the active compound in just the right amount of 0.01 N hydrochloric acid, adjusted with sodium chloride to iso-osmia, sterilized, filtrated, loaded in 10 ml ampoule.

Example 5

Injection 2

| Prescription | |
|---|---|
| Mesylate of compound in Example 1 | 5 g |
| Mannitol | 175 g |
| water for injection | q.s |

Preparation: Dissolve the pharmaceutical salt of active compound and mannitol in just the right amount of water for injection, filtered with microporous membrane. The powder for injection was made after the partial shipments and freeze drying process.

Results Example 1

The Inhibitory of the Compounds Against EGFR, HER2, HER4

Enzyme activity assay was test by the Mobility shift assay method (Expert Opin Drug Discov. 2008, 3(6): 607-621). A 10 mM stock solution of the test compound in DMSO were made after weighing. According to the required concentration, proper quantity of the 10 mM stock solution was dissolved in water to get a work solution with a concentration 5 times the final concentration. And various kinases, EGFR, HER2, HER4 were dissolved into a reaction buffer with a concentration 1.25 times the required concentration (62.5 mM HEPES, pH7.5, 0.001875% Brij-35, 12.5 mM MgCl2, 2.5 mM DTT), and get a enzyme work solution with a concentration 2.5 times the final concentration. At the same time, ATP and FAM tag peptide substrates will be dissolved in the reaction buffer with a concentration of 1.25× to get a substrate and ATP working solution with a concentration 2.5 times the required concentration. Then 5 μl the work solution of compound is added to 384 wells test plate, 5 μl 250 mM EDTA is added to a blank control, the same volume of work solution without drug is added to the negative control (Max). 10 μl Enzyme work solution is added at the same time. After mix gently and hatch for 10 minutes at room temperature, 10 μl substrate and ATP work solution are added to each well. The test plates are placed at 28 degrees for 60 mins. Then 25 μl suspending liquid is added into each reaction well (100 mM HEPES, pH7.5, 0.015% Brij-35, 0.2% Coating Reagent#3, 50 mM EDTA) to quench the enzyme reaction. Finally, the plate is put on Caliper EZ reader to collect conversion rate of the substrate in each well (The phosphorylation ratio of the substrate caused by the kinases). Based on the data described above, the kinase inhibitory of the compound can be calculated as follows: % inh=(Max−conversion)/(Max−Min)×100, wherein % inh is percent inhibition, Max is the conversion ratio of the substrate in negative control well, min is the conversion ratio of the substrate in blank control well, conversion is the conversion rate of substrate in each well with various concentration of the test compound. The % inh value of each concentration of the test compound would be analyzed in Xlift to obtain the corresponding $IC_{50}$ value, the curve fitting formula is: $Y=Bottom+(Top-Bottom)/(1+10\wedge((Log\ IC50-X)*Hillslope))$ The results are as follows:

| Compound No | Kinase inhibitory activity $IC_{50}$ (nM) | | |
|---|---|---|---|
| | EGFR | HER2 | HER4 |
| 1 | 1.7 | 168 | 21 |
| 2-1 | 1.3 | 75 | 23 |
| 2-2 | 4.5 | 369 | 63 |
| 3-1 | 2.5 | ND | ND |
| 4-1 | ND | 62 | ND |
| 4-2 | 9.5 | 64 | 206 |

Results Examples 2

The Inhibitory of the Compounds Against EGFR Tyrosine Kinase

The activity of inhibitory against the kinase of the test compound is expressed by $IC_{50}$. The assays are performed by Homogeneous time-resolved fluorescence (HTRF) method which is as follows: a series of synthesized analogues with gradient concentration are incubated for 5 minutes in enzymatic solution with specific concentration (for EGFR) at room temperature. Then proper amount of substrate and ATP are added into the reaction mixture to start the enzyme reaction. The assays of the specific concentration of compound is measured by Flexstation III of Molecular device company after the stop buffer and detecting liquid are added to the enzyme reaction system and hatch at room temperature for 1 hour. And the activity of inhibitory against the kinase of the test compound with different concentration will be calculated, then according to the 4-parameter equation, fit the inhibitory activity of the test compound with different concentration to get the $IC_{50}$. EGFR is purchased from Sigma Aldrich. The HTRF KinEASE-TK is purchased from Cisbio Bioassays. ATP is purchased from Sigma Aldrich.

The $IC_{50}$ data of the test compounds in the invention are as follows:

| Example No | $IC_{50}$ (nM) EGFR |
|---|---|
| 5 | 0.39 |
| 6 | 0.54 |
| 8-1 | 0.67 |
| 8-2 | 0.29 |
| 19-1 | 0.57 |
| 19-2 | 0.89 |
| 20-1 | 1.00 |
| 20-2 | 0.26 |
| 21-1 | 0.16 |
| 21-2 | 0.31 |
| 22-1 | 0.53 |
| 22-2 | 0.30 |
| 23 | 1.6 |
| 24 | 0.19 |
| 25 | 0.19 |
| 26 | 0.35 |
| 28 | 0.32 |
| 29 | 3.3 |
| 30 | 0.22 |
| 31 | 1.4 |
| 32 | 0.72 |
| 34 | 0.65 |
| 35 | 0.97 |
| 37 | 4.7 |
| 38 | 0.35 |
| 40 | 1.0 |
| 41 | 0.37 |
| 42 | 0.55 |
| 43 | 1.3 |
| 44 | 0.29 |
| 45 | 0.17 |
| 46 | 0.31 |
| 47 | 1.88 |
| 48 | 0.65 |
| 50 | 5.5 |
| 51 | 4.9 |
| 52 | 0.22 |
| 53 | 0.36 |
| 54 | 1.1 |
| 55 | 0.97 |
| 56 | 0.22 |
| 57 | 0.13 |
| 58 | 1.0 |
| 59 | 0.63 |
| 61 | 4.5 |
| 64 | 4.5 |

Results Example 3

Proliferation Inhibitory Activity Against the A431, H1975 Cell

This example is to determine the proliferation inhibitory activity against wide type of high expression cell lines A431 of EGFR and mutant cell lines NCI-H1975$^{L858RT790M}$, the proliferation inhibitory activity in cell-based level of compound is expressed by $IC_{50}$. The test method is as follows: both cell lines are purchased from American type culture collection (ATCC). The cells are seeded in a white and opaque 384-well culture plate with a proper concentration (A431: 20000 cells/ml medium; H1975: 15000 cells/ml medium), cultured at 37° C. with 5% $CO_2$ for 24 hrs, a series of medicine with gradient concentration is added, generally 10 concentrations, cultured for another 48 hours under the previous conditions. The assays of the proliferation inhibitory activity against the A431 and H1975 cell of the test compounds are performed by the CellTiter-Glo Luminescent Cell Viability Assay and calculate the proliferation inhibitory activity of compound with different concentrations. CellTiter-Glo Luminescent Cell Viability Assay is purchased from Promega. Fit the data of proliferation inhibitory activity against A431 and H1975 of compounds with different concentrations with 4-parameter equation. The $IC_{50}$ data of the test compounds in this invention are as follows:

| Example No | $IC_{50}$ (A431) (μM) | $IC_{50}$ (H1975) (μM) |
|---|---|---|
| 2-1 | 0.55 | 0.41 |
| 5 | 3.2 | 2.5 |
| 6 | 0.50 | 1.2 |
| 8-1 | 0.68 | 1.0 |
| 8-2 | 2.1 | 0.76 |
| 19-1 | 0.98 | 0.64 |
| 19-2 | 0.98 | 1.1 |
| 20-1 | 12 | 4.3 |
| 20-2 | >100 | 2.3 |
| 21-1 | 98 | 1.2 |
| 21-2 | 3.1 | 1.5 |
| 22-1 | 8.1 | 3.7 |
| 22-2 | 2.9 | 2.4 |
| 23 | 1.3 | 3.0 |
| 24 | 1.3 | 2.2 |
| 25 | 1.2 | 1.9 |
| 26 | 4.5 | 5.4 |
| 27 | — | 2.7 |
| 28 | 29 | 1.4 |
| 29 | 5.9 | 1.9 |
| 30 | 0.52 | 1.5 |
| 31 | 6.5 | 6.0 |
| 32 | 4.2 | 5.6 |
| 34 | >100 | 5.2 |
| 35 | >100 | 8.5 |
| 37 | >100 | 1.9 |
| 38 | 0.18 | 1.1 |
| 40 | 1.3 | 3.4 |
| 42 | 0.53 | 2.4 |
| 43 | 1.68 | 3.4 |
| 44 | 0.53 | 3.7 |
| 45 | 45 | 9.3 |
| 46 | >100 | 7.7 |
| 47 | 14 | 1.5 |
| 48 | 13 | 1.8 |
| 49 | 8.6 | 5.6 |
| 50 | 15 | 2.4 |
| 51 | 20 | 7.3 |
| 52 | 1.6 | 0.47 |
| 53 | 36 | 1.0 |
| 54 | 3.8 | 13 |
| 55 | 22 | 13 |
| 56 | 2.8 | 0.51 |
| 57 | 7.5 | 1.3 |
| 58 | 27 | 8.3 |
| 59 | 10 | 11 |
| 61 | 0.8 | 1.0 |
| 64 | 3.6 | 2.7 |

Conclusion:
The compounds in this invention have significant proliferation inhibitory activity against A431 and H1975.

Results Example 4

Antitumor Efficacy on the H1975 Nude Mice Model

1. Abstract
The antitumor effect of compound 2-1(hydrochloride) in example 2, compound in example 5, compound in example 6 on NCI-H1975 nude mice were evaluated. The three compounds significantly inhibit the growth of NCI-H1975 NSCLC, and are well tolerated in mice.

2. Experimental Objective

To evaluate the anti-tumor effects of compounds on NCI-H1975 nude mice.

3. Test Medicine And Preparation Method:

Drug name: compound 2-1(hydrochloride) in example 2, compound in example 5, compound in example 6

Preparation method: dissolve the test compound in 20% PEG400+3% Tween80 to obtain a required concentration; dissolve the control group in 0.5% CMC+0.4% Tween80 to obtain a required concentration.

4. Experimental Animals and Materials

BALB/c nude mice (Shanghai xipuer-bikai experimental animals company), weight 16-18 g, female. BD matrigel, NCI-H1975 cell (ATCC)

5. Experimental Procedure

Cells in logarithmic phase were collected. The ratio of medium to matrigel was 1:1. The concentration of cell was adjust to $3 \times 10^7$/ml and put into a ice box, then inoculated in each nude mice subcutaneously with 0.2 ml. Then carry out intragastric administration once a day for 5 days and stop administration for 2 days. Administrate for 9 days in total. Dosages are as follows:

| Group | Number of animals (n) | Dosage (mg/kg) | Solvent | Drug-delivery way | Dosage regimen |
|---|---|---|---|---|---|
| Control | 5 | (N/A) | 0.5% CMC + 0.4% Tween80 | PO | QD |
| Compound 2-1 in example 2 | 5 | 60 | 20% PEG400 + 3% Tween80 | PO | QD |
| Compound in example 5 | 5 | 60 | 20% PEG400 + 3% Tween80 | PO | QD |
| Compound in example 6 | 5 | 60 | 20% PEG400 + 3% Tween80 | PO | QD |

The size and weight were measured. The length and width of tumors were measured individually with microcalipers. Tumor volume (V) and relative tumor volume (RTV) was calculated as formula. Day 12, all the nude mouse were killed and the tumors were taken out and pictured. The individual as follows: RTV=$V_t/V_0$, where $V_t$ is and $V_0$ is. and the calculation formula is T/C (%)=mean RTV of the treated group/mean RTV of the control group×100%.

(1) Tumor volume (Tumor Volume, TV), calculation formula: V=1/2XaXb, wherein a and b presents length and width respectively.

(2) Relative Tumor Volume (RTV), calculation formula: RTV=$V_t/V_0$.

Wherein TV0 is the volume on the day of initial treatment, TVt is the volume on each day of measurement.

(3) The relative tumor increment rate T/C (%), calculation formula:

$$T/C(\%) = \frac{T_{RTV}}{C_{RTV}} \times 100$$

TRTV: treated group RTV; CRTV: negative control group RTV.

Therapeutic effect of compound was expressed in terms of T/C %.

Experimental Results:

| Day | Control group (mm³) | Compound 2-1 in example 2 (mm³) | Compound in example 5 (mm³) | Compound in example 6 s (mm³) |
|---|---|---|---|---|
| 0 | 193 ± 26 | 190 ± 17 | 177 ± 17 | 179 ± 13 |
| 2 | 265 ± 23 | 153 ± 11 | 160 ± 11 | 154 ± 35 |
| 4 | 509 ± 40 | 121 ± 27 | 164 ± 27 | 113 ± 26 |
| 7 | 866 ± 73 | 130 ± 20 | 147 ± 20 | 66 ± 16 |
| 9 | 1413 ± 172 | 134 ± 27 | 151 ± 27 | 58 ± 11 |
| 11 | 1848 ± 343 | 164 ± 33 | 131 ± 33 | 57 ± 11 |

After 9 days, tumor volume of each group was as following:

In this assay, compounds 2-1 in example 2, compound in example 5 and compound in example 6 show strong inhibitory on NCI-H1975 in nude mice at 60 mpk.

What is claimed is:

1. A compound selected from the group consisting of:
   a quinazoline derivative, a pharmaceutically acceptable salt thereof,
   a racemate of the quinazoline derivative or a pharmaceutically acceptable salt thereof,
   a solvate of the quinazoline derivative or a pharmaceutically acceptable salt thereof, and
   a prodrug of the quinazoline derivative or a pharmaceutically acceptable salt thereof,
   wherein the quinazoline derivative is selected from the group consisting of:
   N-(4-((3-chloro-4-fluorophenyl)amino)-7-methoxyquinazolin-6-yl)-4-(dimethylamino)-2-fluorobut-2-enamide (compound 1);
   (Z)-N-(4-((3-chloro-4-fluorophenyl)amino)-7-methoxyquinazolin-6-yl)-4-(dimethylamino)-2-fluorobut-2-enamide (compound 2-1);
   (E)-N-(4-((3-chloro-4-fluorophenyl)amino)-7-methoxyquinazolin-6-yl)-4-(dimethylamino)-2-fluorobut-2-enamide (compound 2-2);
   N-(4-((3-chloro-4-fluorophenyl)amino)-7-(2-methoxy)ethoxyquinazolin-6-yl)-4-(dimethylamino)-2-fluorobut-2-enamide (compound 3-1);
   N-(4-((3-chloro-4-fluorophenyl)amino)-7-ethoxyquinazolin-6-yl)-4-(dimethylamino)-2-fluorobut-2-enamide (compound 3-2);
   N-(4-((3-chloro-4-fluorophenyl)amino)-7-(2-methoxyethoxy)quinazolin-6-yl)-2-fluoro-4-morpholinobut-2-enamide (compound 3-3);
   N-(4-((3-chloro-4-fluorophenyl)amino)-7-((3R)-tetrahydrofuran-3-yloxy)quinazolin-6-yl)-4-(dimethylamino)-2-fluorobut-2-enamide (compound 3-4);
   N-(4-((3-chloro-4-fluorophenyl)amino)-7-((tetrahydro-2H-pyran-4-yl)methoxy)quinazolin-6-yl)-4-(dimethylamino)-2-fluorobut-2-enamide (compound 3-5);
   N-(4-((3-chloro-4-fluorophenyl)amino)-7-methoxyquinazolin-6-yl)-4-(diethylamino)-2-fluorobut-2-enamide (compound 3-6);
   N-(4-((3-chloro-4-fluorophenyl)amino)-7-(2-methoxyethoxy)quinazolin-6-yl)-2-fluoro-4-(4-methylpiperazin-1-yl)but-2-enamide (compound 3-7);
   N-(4-((3-chloro-4-fluorophenyl)amino)-7-methoxyquinazolin-6-yl)-2-fluoro-4-((2-methoxyethyl)(methyl)amino)but-2-enamide (compound 3-8);
   N-(4-((3-chloro-4-fluorophenyl)amino)-7-methoxyquinazolin-6-yl)-2-fluoro-4-(4-methylpiperazin-1-yl)but-2-enamide (compound 3-9);
   N-(4-((3-chloro-4-fluorophenyl)amino)-7-methoxyquinazolin-6-yl)-2-fluoro-4-(methyl)(tetrahydrofuran-3-yl)amino)but-2-enamide (compound 3-10);

N-(4-((3-chloro-4-fluorophenyl)amino)-7-methoxyquinazolin-6-yl)-4-(2-(dimethylamino)ethoxy)-2-fluorobut-2-enamide (compound 3-11);

N-(4-((3-chloro-4-fluorophenyl)amino)-7-methoxyquinazolin-6-yl)-2-fluoro-3-(1-methylpyrrolidine-2(S)-yl)acrylamide (compound 3-12);

N-(4-((3-chloro-4-(pyridin-2-ylmethoxy)phenyl)amino)-7-methoxyquinazolin-6-yl)-4-(dimethylamino)-2-fluorobut-2-enamide (compound 3-13);

N-(4-(4-((3-fluorobenzyloxy)-3-chlorophenyl)amino)-7-methoxyquinazolin-6-yl)-4-(dimethylamino)-2-fluorobut-2-enamide (compound 3-14);

N-(4-(1-(3-fluorobenzyl)-1H-indazol-5-ylamino)-7-methoxyquinazolin-6-yl)-4-(dimethylamino)-2-fluorobut-2-enamide (compound 3-15);

4-(dimethylamino)-N-(4-(((3-ethynylphenyl)amino)-7-methoxyquinazolin-6-yl)-2-fluorobut-2-enamide (compound 3-16);

N-(4-((2,4-dichloro-5-methoxyphenyl)amino)-7-methoxyquinazolin-6-yl)-4-(dimethylamino)-2-fluorobut-2-enamide (compound 3-17);

N-(4-((5-chlorobenzo[d][1,3]dioxol-4-yl)amino)-7-methoxyquinazolin-6-yl)-4-(dimethylamino)-2-fluorobut-2-enamide (compound 3-18);

N-(4-((4-chloro-3-(trifluoromethyl)phenyl)amino)-7-methoxyquinazolin-6-yl)-4-(dimethylamino)-2-fluorobut-2-enamide (compound 3-19);

N-(4-((3-bromophenyl)amino)-7-methoxyquinazolin-6-yl)-4-(dimethylamino)-2-fluorobut-2-enamide (compound 3-20);

N-(4-((3-chloro-2-fluorophenyl)amino)-7-methoxyquinazolin-6-yl)-4-(dimethylamino)-2-fluorobut-2-enamide (compound 3-21);

N-(4-((4-bromo-2-fluorophenyl)amino)-7-methoxyquinazolin-6-yl)-4-(dimethylamino)-2-fluorobut-2-enamide (compound 3-22);

N-(4-((3-chloro-2,4-difluorophenyl)amino)-7-methoxyquinazolin-6-yl)-4-(dimethylamino)-2-fluorobut-2-enamide (compound 3-23);

N-(4-((3,4-dichloro-2-fluorophenyl)amino)-7-methoxyquinazolin-6-yl)-4-(dimethylamino)-2-fluorobut-2-enamide (compound 3-24);

N-(4-((4-bromo-3-chloro-2-fluorophenyl)amino)-7-methoxyquinazolin-6-yl)-4-(dimethylamino)-2-fluorobut-2-enamide (compound 3-25);

(Z)-N-(4-(3-chloro-4-(pyridin-2-ylmethoxy)phenyl)amino)-7-methoxyquinazolin-6-yl)-4-(dimethylamino)-2-fluorobut-2-enamide (compound 4-1);

(E)-N-(4-((3-chloro-4-(pyridin-2-ylmethoxy)phenyl)amino)-7-methoxyquinazolin-6-yl)-4-(dimethylamino)-2-fluorobut-2-enamide (compound 4-2);

N-(4-((3-chloro-4-fluorophenyl)amino)-7-(3-morpholinopropoxy)quinazolin-6-yl)-2-fluoroacrylamide (compound 5);

N-(4-((3-chloro-2,4-difluorophenyl)amino)-7-((1-methylpiperidin-4-yl)methoxy)quinazolin-6-yl)-2-fluoroacrylamide (compound 6);

N-(4-((3-chloro-4-fluorophenyl)amino)-7-methoxyquinazolin-6-yl)-2-fluoro-4-(piperidin-1-yl)but-2-enamide (compound 7);

(Z)-N-(4-((3-chloro-4-fluorophenyl)amino)-7-methoxyquinazolin-6-yl)-2-fluoro-4-(piperidin-1-yl)but-2-enamide (compound 8-1);

(E)-N-(4-((3-chloro-4-fluorophenyl)amino)-7-methoxyquinazolin-6-yl)-2-fluoro-4-(piperidin-1-yl)but-2-enamide (compound 8-2);

N-(4-((3-chloro-4-(pyridin-2-ylmethoxyl)phenyl)amino)-7-ethoxyquinazolin-6-yl)-4-(dimethylamino)-2-fluorobut-2-enamide (compound 9);

(S)-N-(4-((3-chloro-4-fluorophenyl)amino)-7-(tetrahydrofuran-3-yl)oxy)quinazolin-6-yl)-2-fluoro-4-morpholinobut-2-enamide (compound 10);

(S)-N-(4-((3-chloro-4-fluorophenyl)amino)-7-((tetrahydrofuran-3-yl)oxy)quinazolin-6-yl)-4-(dimethylamino)-2-fluorobut-2-enamide (compound 11);

N-(4-((3-chloro-4-fluorophenyl)amino)-7-methoxyquinazolin-6-yl)-2-fluoro-4-morpholinobut-2-enamide (compound 12);

N-(4-((3-bromophenyl)amino)-7-ethoxyquinazolin-6-yl)-2-fluoro-4-(piperidin-1-yl)but-2-enamide (compound 13);

N-(4-((3-chloro-4-fluorophenyl)amino)-7-(2-methoxyethoxy)quinazolin-6-yl)-2-fluoro-4-(piperidin-1-yl)but-2-enamide (compound 14);

N-(4-((3-chloro-4-(pyridin-2-ylmethoxy)phenyl)amino)-7-ethoxyquinazolin-6-yl)-2-fluoro-4-(piperidin-1-yl)but-2-enamide (compound 15);

N-(4-((3-bromophenyl)amino)-7-ethoxyquinazolin-6-yl)-4-(dimethylamino)-2-fluorobut-2-enamide (compound 16);

N-(4-((3-bromophenyl)amino)-7-ethoxyquinazolin-6-yl)-2-fluoro-4-morpholinobut-2-enamide (compound 17);

N-(4-((3-chloro-4-fluorophenyl)amino)-7-methoxyquinazolin-6-yl)-2-fluoro-4-(pyrrolidin-1-yl)but-2-enamide (compound 18);

(Z)-N-(4-((3-chloro-4-(pyridin-2-ylmethoxy)phenyl)amino)-7-ethoxyquinazolin-6-yl)-4-(dimethylamino)-2-fluorobut-2-enamide (compound 19-1);

(E)-N-(4-((3-chloro-4-(pyridin-2-ylmethoxy)phenyl)amino)-7-ethoxyquinazolin-6-yl)-4-(dimethylamino)-2-fluorobut-2-enamide (compound 19-2);

(S,Z)-N-(4-((3-chloro-4-fluorophenyl)amino)-7-((tetrahydrofuran-3-yl)oxy)quinazolin-6-yl)-2-fluoro-4-morpholinobut-2-enamide (compound 20-1);

(S,E)-N-(4-((3-chloro-4-fluorophenyl)amino)-7-((tetrahydrofuran-3-yl)oxy)quinazolin-6-yl)-2-fluoro-4-morpholinobut-2-enamide (compound 20-2);

(S,Z)-N-(4-((3-chloro-4-fluorophenyl)amino)-7-((tetrahydrofuran-3-yl)oxy)quinazolin-6-yl)-4-(dimethylamino)-2-fluorobut-2-enamide (compound 21-1);

(S,E)-N-(4-((3-chloro-4-fluorophenyl)amino)-7-((tetrahydrofuran-3-yl)oxy)quinazolin-6-yl)-4-(dimethylamino)-2-fluorobut-2-enamide (compound 21-2);

(Z)-N-(4-((3-chloro-4-fluorophenyl)amino)-7-methoxyquinazolin-6-yl)-2-fluoro-4-morpholinobut-2-enamide (compound 22-1);

(E)-N-(4-((3-chloro-4-fluorophenyl)amino)-7-methoxyquinazolin-6-yl)-2-fluoro-4-morpholinobut-2-enamide (compound 22-2);

N-[4-(4-bromo-2-fluorophenylamino)-7-(3-morpholinopropoxy)quinazolin-6-yl]-2-fluoroacrylamide (compound 23);

N-[4-((3-chloro-2,4-difluorophenyl)amino)-7-(3-morpholinopropoxy)quinazolin-6-yl]-2-fluoroacrylamide (compound 24);

N-[4-(3-ethynylphenylamino)-7-(3-morpholinopropoxy)quinazolin-6-yl]-2-fluoroacrylamide (compound 25);

N-[4-((3-chloro-2-fluorophenyl)amino)-7-(3-morpholinopropoxy)quinazolin-6-yl]-2-fluoroacrylamide (compound 26);

N-[4-((2,4-dichloro-5-methoxyphenyl)amino)-7-(3-morpholinopropoxy)quinazolin-6-yl]-2-fluoroacrylamide (compound 27);

N-[4-((3-bromophenyl)amino)-7-(3-morpholinopropoxy)quinazolin-6-yl]-2-fluoroacrylamide (compound 28);

N-[4-((3-chloro-4-((3-fluorobenzyl)oxy)phenyl)amino)-7-(3-morpholinopropoxy)quinazolin-6-yl]-2-fluoroacrylamide (compound 29);

N-[4-((3,4-dichloro-2-fluorophenyl)amino)-7-(3-morpholinopropoxy)quinazolin-6-yl]-2-fluoroacrylamide (compound 30);

N-[4-((2,4-difluorophenyl)amino)-7-(3-morpholinopropoxy)quinazolin-6-yl]-2-fluoroacrylamide (compound 31);

2-fluoro-N-(7-(3-morpholinopropoxy)-4-((2,3,4-trifluorophenyl)amino)quinazolin-6-yl]acrylamide (compound 32);

N-[4-((2,4-dichlorophenyl)amino)-7-(3-morpholinopropoxy)quinazolin-6-yl]-2-fluoroacrylamide (compound 33);

2-chloro-N-(4-((3-chloro-2,4-difluorophenyl)amino)-7-(3-morpholinopropoxy)quinazolin-6-yl)acrylamide (compound 34);

2-chloro-N-(4-((3-chloro-4-fluorophenyl)amino)-7-(3-morpholinopropoxy)quinazolin-6-yl)acrylamide (compound 35);

N-(4-((2,4-difluoro-3-methoxyphenyl)amino)-7-(3-morpholinopropoxy)quinazolin-6-yl)-2-fluoroacrylamide (compound 36);

N-(4-((4-chloro-3-methoxyphenyl)amino)-7-(3-morpholinopropoxy)quinazolin-6-yl)-2-fluoroacrylamide (compound 37);

N-(4-((4-bromo-3-chloro-2-fluorophenyl)amino)-7-(3-morpholinopropoxy)quinazolin-6-yl)-2-fluoroacrylamide (compound 38);

N-(4-((3-chloro-4-((3-fluorobenzyl)oxy)phenyl)amino)-7-ethoxyquinazolin-6-yl)-2-fluoroacrylamide (compound 39);

N-(4-((3-chloro-4-fluorophenyl)amino)-7-(3-(piperidine-1-yl)propoxy)quinazolin-6-yl)-2-fluoroacrylamide (compound 40);

2-chloro-N-(4-((3-chloro-4-fluorophenyl)amino)-7-(3-morpholinopropoxy)quinazolin-6-yl)acrylamide (compound 41);

N-(4-((3-chloro-4-fluorophenyl)amino)-7-(3-(dimethylamino)propoxy)quinazolin-6-yl)-2-fluoroacrylamide (compound 42);

N-(4-((3-chloro-4-fluorophenyl)amino)-7-(3-(pyrrolidin-1-yl)propoxy)quinazolin-6-yl)-2-fluoroacrylamide (compound 43);

N-(4-((3-chloro-4-fluorophenyl)amino)-7-(3-(4-methylpiperazin-1-yl)propoxy)quinazolin-6-yl)-2-fluoroacrylamide (compound 44);

(R)-N-(4-((3-chloro-2,4-difluorophenyl)amino)-7-((tetrahydrofuran-3-yl)methoxy)quinazolin-6-yl)-2-fluoroacrylamide (compound 45);

(R)-N-(4-((3-chloro-2,4-difluorophenyl)amino)-7-((tetrahydrofuran-3-yl)methoxy)quinazolin-6-yl)-2-fluoroacrylamide (compound 46);

N-(4-((3-chloro-2,4-difluorophenyl)amino)-7-(cyclobutylmethoxy)quinazolin-6-yl)-2-fluoroacrylamide (compound 47);

N-(4-((3-chloro-2,4-difluorophenyl)amino)-7-(cyclopropylmethoxy)quinazolin-6-yl)-2-fluoroacrylamide (compound 48);

N-(4-((3-chloro-4-fluorophenyl)amino)-7-((1-methylpiperidin-4-yl)oxy)quinazolin-6-yl)-2-fluoroacrylamide (compound 49);

(R)-N-(4-((3-chloro-2,4-difluorophenyl)amino)-7-((1-methylpyrrolidin-3-yl)oxy)quinazolin-6-yl)-2-fluoroacrylamide (compound 50);

(S)-N-(4-((3-chloro-2,4-difluorophenyl)amino)-7-((1-methylpyrrolidin-3-yl)oxy)quinazolin-6-yl)-2-fluoroacrylamide (compound 51);

N-(4-((3-bromophenyl)amino)-7-methoxyquinazolin-6-yl)-2-fluoroacrylamide (compound 52);

N-(4-((3-bromophenyl)amino)-7-ethoxyquinazolin-6-yl)-2-fluoroacrylamide (compound 53);

2-fluoro-N-(7-methoxy-4-((3-(trifluoromethyl)phenyl)amino)quinazolin-6-yl)acrylamide (compound 54);

N-(7-ethoxy-4-((3-(trifluoromethyl)phenyl)amino)quinazolin-6-yl)-2-fluoroacrylamide (compound 55);

N-(4-((3-chloro-4-fluorophenyl)amino)-7-methoxyquinazolin-6-yl)-2-fluoroacrylamide (compound 56);

2-chloro-N-(4-((3-chloro-4-fluorophenyl)amino)-7-methoxyquinazolin-6-yl)acrylamide (compound 57);

2-chloro-N-(7-ethoxy-4-((3-(trifluoromethyl)phenyl)amino)quinazolin-6-yl)acrylamide (compound 58);

N-(4-((3-bromophenyl)amino)-7-ethoxyquinazolin-6-yl)-2-chloroacrylamide (compound 59);

2-chloro-N-(4-((3-chloro-4-((3-fluorobenzyl)oxy)phenyl)amino)-7-ethoxyquinazolin-6-yl)acrylamide (compound 60);

N-(4-((3-chloro-4-(cyclopropylbenzyloxy)phenyl)amino)-7-(3-morpholinopropoxy)quinazolin-6-yl)-2-fluoroacrylamide (compound 61);

2-chloro-N-(4-((3-chloro-4-(cyclopropylbenzyloxy)phenyl)amino)-7-(3-morpholinopropoxy)quinazolin-6-yl)acrylamide (compound 62);

(R)-N-(4-((3-chloro-4-fluorophenyl)amino)-7-((1-methylpyrrolidin-3-yl)oxy)quinazolin-6-yl)-2-fluoroacrylamide (compound 63);

(S)-N-(4-((3-chloro-4-fluorophenyl)amino)-7-((1-methylpyrrolidin-3-yl)oxy)quinazolin-6-yl)-2-fluoroacrylamide (compound 64);

(R)-N-(4-((3-chloro-4-fluorophenyl)amino)-7-((4-methylmorpholin-3-yl)methoxy)quinazolin-6-yl)-2-fluoroacrylamide (compound 65);

(R)-2-chloro-N-(4-((3-chloro-4-fluorophenyl)amino)-7-((4-methylmorpholin-3-yl)methoxy)quinazolin-6-yl)acrylamide (compound 66);

N-(4-((3-chloro-4-fluorophenyl)amino)-7-(2-(piperidin-1-yl)ethoxy)quinazolin-6-yl)-2-fluoroacrylamide (compound 67);

2-chloro-N-(4-((3-chloro-4-fluorophenyl)amino)-7-(2-(piperidin-1-yl)ethoxy)quinazolin-6-yl)acrylamide (compound 68);

2-chloro-N-(4-((3-chloro-4-(pyridin-2-ylmethoxy)phenyl)amino)-7-ethoxyquinazolin-6-yl)acrylamide (compound 69);

2-chloro-N-(4-((3-chloro-4-(cyclopropylmethoxy)phenyl)amino)-7-((1-methylpiperidin-4-yl)methoxy)quinazolin-6-yl)acrylamide (compound 70);

N-(4-((3-chloro-4-(cyclopropylmethoxy)phenyl)amino)-7-((1-methylpiperidin-4-yl)methoxy)quinazolin-6-yl)-2-fluoroacrylamide (compound 71);

(S)-N-(4-((3-chloro-4-fluorophenyl)amino)-7-((4-methylmorpholin-3-yl)methoxy)quinazolin-6-yl)-2-fluoroacrylamide (compound 72);

(S)-N-(4-((3-chloro-4-fluorophenyl)amino)-7-((1-methylpiperidin-3-yl)methoxy)quinazolin-6-yl)-2-fluoroacrylamide (compound 73);

(R)-N-(4-((3-chloro-4-fluorophenyl)amino)-7-((1-methylpiperidin-3-yl)methoxy)quinazolin-6-yl)-2-fluoroacrylamide (compound 74);

(S)-N-(4-((3-chloro-4-fluorophenyl)amino)-7-((4-methylmorpholin-2-yl)methoxy)quinazolin-6-yl)-2-fluoroacrylamide (compound 75);

(R)-N-(4-((3-chloro-4-fluorophenyl)amino)-7-((4-methylmorpholin-2-yl)methoxy)quinazolin-6-yl)-2-fluoroacrylamide (compound 76);

N-(4-((3-chloro-4-fluorophenyl)amino)-7-(2-(1-methylpiperidin-4-yl)ethoxy)quinazolin-6-yl)-2-fluoroacrylamide (compound 77);

N-(4-((3-chloro-4-fluorophenyl)amino)-7-(2-(4-methylpiperazin-1-yl)ethoxy)quinazolin-6-yl)-2-fluoroacrylamide (compound 78);

N-(4-((3-chloro-4-fluorophenyl)amino)-7-(2-morpholinoethoxy)quinazolin-6-yl)-2-fluoroacrylamide (compound 79);

(R)-N-(4-((3-chloro-4-fluorophenyl)amino)-7-(2-(1-methylpyrrolidin-2-yl)ethoxy)quinazolin-6-yl)-2-fluoroacrylamide (compound 80);

(S)-N-(4-((3-chloro-4-fluorophenyl)amino)-7-(2-(1-methylpyrrolidin-2-yl)ethoxy)quinazolin-6-yl)-2-fluoroacrylamide (compound 81);

(R)-N-(4-((3-chloro-4-fluorophenyl)amino)-7-(2-(1-methylpiperidin-2-yl)ethoxy)quinazolin-6-yl)-2-fluoroacrylamide (compound 82);

(S)-N-(4-((3-chloro-4-fluorophenyl)amino)-7-(2-(1-methylpiperidin-2-yl)ethoxy)quinazolin-6-yl)-2-fluoroacrylamide (compound 83);

(R)-N-(4-((3-chloro-4-fluorophenyl)amino)-7-(2-(1-methylpiperidin-3-yl)ethoxy)quinazolin-6-yl)-2-fluoroacrylamide (compound 84);

(S)-N-(4-((3-chloro-4-fluorophenyl)amino)-7-(2-(1-methylpiperidin-3-yl)ethoxy)quinazolin-6-yl)-2-fluoroacrylamide (compound 85);

N-(4-((3-chloro-4-fluorophenyl)amino)-7-((1-methylpiperidin-4-yl)methoxy)quinazolin-6-yl)-2-fluoroacrylamide (compound 86);

N-(4-((3-bromophenyl)amino)-7-((1-methylpiperidin-4-yl)methoxy)quinazolin-6-yl)-2-fluoroacrylamide (compound 87); and (S)-2-chloro-N-(4-((3-chloro-4-fluorophenyl)amino)-7-(4-methylmorpholin-3-yl)methoxy)quinazolin-6-yl)acrylamide (compound 88).

2. A pharmaceutical composition comprising a compound according to claim 1.

3. A method of treating lung cancer or skin cancer or skin cancer in a patient in need thereof comprising:

administering to the patient a medicament comprising an effective amount of a compound according to claim 1 or a pharmaceutical composition that comprises the compound.

4. A method of treating tumors mediated by EGFR, HER2, or HER4 in a patient in need thereof, comprising:

administering to the patient a medicament comprising an effective amount of a compound according to claim 1 or a pharmaceutical composition that comprises the compound.

\* \* \* \* \*